United States Patent
Iyer et al.

(10) Patent No.: US 10,272,073 B2
(45) Date of Patent: *Apr. 30, 2019

(54) APPARATUS AND METHODS FOR PREVENTING OR TREATING FAILURE OF HEMODIALYSIS VASCULAR ACCESS AND OTHER VASCULAR GRAFTS

(71) Applicant: Vascular Therapies, Inc., Cresskill, NJ (US)

(72) Inventors: Sriram S. Iyer, New York, NY (US); Nicholas N. Kipshidze, New York, NY (US); Victor V. Nikolaychik, Mequon, WI (US)

(73) Assignee: Vascular Therapies, Inc., Cresskill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/509,279

(22) Filed: Oct. 8, 2014

(65) Prior Publication Data

US 2015/0209334 A1    Jul. 30, 2015

Related U.S. Application Data

(60) Division of application No. 11/931,143, filed on Oct. 31, 2007, now Pat. No. 8,858,982, which is a (Continued)

(51) Int. Cl.
*A61F 2/00*  (2006.01)
*A61K 31/44* (2006.01)
(Continued)

(52) U.S. Cl.
CPC .......... *A61K 31/436* (2013.01); *A61K 9/0024* (2013.01); *A61K 31/122* (2013.01);
(Continued)

(58) Field of Classification Search
CPC .................................................... A61K 9/0024
(Continued)

(56) References Cited

U.S. PATENT DOCUMENTS 3,707,485 A    12/1972  Gutsche et al.
4,164,559 A    8/1979   Miyata et al.
(Continued)

FOREIGN PATENT DOCUMENTS

EP    1192957 A2    4/2002
JP    2011506364    3/2011
(Continued)

OTHER PUBLICATIONS

Mertig et al. "Dewetting of thin collagenous precursor film," Appl. Phys. A, 1998, vol. 66, pp. S565-S568.*
(Continued)

*Primary Examiner* — Shengjun Wang
(74) *Attorney, Agent, or Firm* — Husch Blackwell LLP

(57) ABSTRACT

This invention is a prosthetic device generally placed on the outside surface of the vessel or graft which then elutes antiproliferative drugs or agents from a drug-eluting matrix material. Methods of perivascular antiproliferative drug administration also are disclosed.

10 Claims, 14 Drawing Sheets

Related U.S. Application Data continuation of application No. 10/832,048, filed on Apr. 26, 2004, now Pat. No. 7,807,191, which is a continuation of application No. 10/051,708, filed on Jan. 16, 2002, now Pat. No. 6,726,923.

(60) Provisional application No. 60/262,132, filed on Jan. 16, 2001.

(51) Int. Cl.
| | |
|---|---|
| A61K 31/436 | (2006.01) |
| A61K 9/00 | (2006.01) |
| A61K 31/122 | (2006.01) |
| A61K 31/337 | (2006.01) |
| A61K 31/395 | (2006.01) |
| A61K 31/573 | (2006.01) |
| A61K 31/727 | (2006.01) |
| A61L 31/16 | (2006.01) |
| A61M 1/36 | (2006.01) |
| A61M 39/02 | (2006.01) |
| A61L 27/20 | (2006.01) |
| A61L 27/22 | (2006.01) |
| A61L 27/44 | (2006.01) |
| A61L 27/54 | (2006.01) |
| A61M 1/16 | (2006.01) |

(52) U.S. Cl.
CPC .......... *A61K 31/337* (2013.01); *A61K 31/395* (2013.01); *A61K 31/573* (2013.01); *A61K 31/727* (2013.01); *A61L 27/20* (2013.01); *A61L 27/225* (2013.01); *A61L 27/44* (2013.01); *A61L 27/54* (2013.01); *A61L 31/16* (2013.01); *A61M 1/3655* (2013.01); *A61M 39/0247* (2013.01); *A61L 2300/204* (2013.01); *A61L 2300/252* (2013.01); *A61L 2300/416* (2013.01); *A61M 1/16* (2013.01); *A61M 2039/0258* (2013.01); *A61M 2039/0261* (2013.01); *A61M 2202/0468* (2013.01); *A61M 2202/0478* (2013.01)

(58) Field of Classification Search
USPC ................................ 424/423, 426
See application file for complete search history.

(56) References Cited

U.S. PATENT DOCUMENTS

| | | | |
|---|---|---|---|
| 4,391,797 A | 7/1983 | Folkman et al. | |
| 4,409,332 A | 10/1983 | Jefferies et al. | |
| 4,677,120 A | 6/1987 | Parish et al. | |
| 4,840,940 A | 6/1989 | Sottiurai | |
| 4,863,457 A | 9/1989 | Lee | |
| 4,885,311 A | 12/1989 | Parish et al. | |
| 4,889,842 A | 12/1989 | Morris | |
| 4,994,491 A | 2/1991 | Purcell et al. | |
| 5,049,584 A | 9/1991 | Purcell et al. | |
| 5,074,869 A | 12/1991 | Daicoff | |
| 5,100,668 A | 3/1992 | Edelman et al. | |
| 5,124,356 A | 6/1992 | Purcell et al. | |
| 5,138,051 A | 8/1992 | Hughes et al. | |
| 5,157,049 A | 10/1992 | Haugwitz et al. | |
| 5,169,851 A | 12/1992 | Hughes et al. | |
| 5,202,332 A | 4/1993 | Hughes et al. | |
| 5,223,269 A | 6/1993 | Liepins | |
| 5,283,257 A | 2/1994 | Gregory et al. | |
| 5,288,711 A | 2/1994 | Mitchell et al. | |
| 5,455,039 A * | 10/1995 | Edelman ............... | A61K 9/0019 424/422 |
| 5,486,524 A | 1/1996 | Failli et al. | |
| 5,496,804 A | 3/1996 | Reed et al. | |
| 5,516,781 A | 5/1996 | Morris et al. | |
| 5,519,042 A | 5/1996 | Morris et al. | |
| 5,527,532 A | 6/1996 | Edleman et al. | |
| 5,540,928 A | 7/1996 | Edelman et al. | |
| 5,562,726 A | 10/1996 | Chuter et al. | |
| 5,563,146 A * | 10/1996 | Morris ................. | A61K 31/436 424/122 |
| 5,571,800 A | 11/1996 | Morris et al. | |
| 5,593,974 A | 1/1997 | Rosenberg et al. | |
| 5,614,645 A | 3/1997 | Kingston et al. | |
| 5,616,608 A | 4/1997 | Kinsella et al. | |
| 5,621,001 A | 4/1997 | Canetta et al. | |
| 5,641,803 A | 6/1997 | Carretta et al. | |
| 5,646,160 A | 7/1997 | Morris et al. | |
| 5,660,873 A | 8/1997 | Nikolaychik et al. | |
| 5,665,728 A | 9/1997 | Morris et al. | |
| 5,665,761 A | 9/1997 | Canetta et al. | |
| 5,670,537 A | 9/1997 | Canetta et al. | |
| 5,716,981 A | 2/1998 | Hunter et al. | |
| 5,733,925 A | 3/1998 | Kunz et al. | |
| 5,766,584 A * | 6/1998 | Edelman ............... | A61L 27/507 424/425 |
| 5,780,653 A | 7/1998 | Tao et al. | |
| 5,795,286 A | 8/1998 | Fishcell et al. | |
| 5,811,447 A | 9/1998 | Kunz et al. | |
| 5,821,363 A | 10/1998 | Wicnienski et al. | |
| 5,824,049 A | 10/1998 | Ragheb et al. | |
| 5,837,728 A | 11/1998 | Purcell | |
| 5,886,026 A | 3/1999 | Hunter et al. | |
| 5,965,739 A | 10/1999 | Kelly et al. | |
| 5,981,568 A | 11/1999 | Kunz et al. | |
| 5,994,341 A | 11/1999 | Hunter et al. | |
| 6,002,023 A | 12/1999 | Kingston et al. | |
| 6,015,815 A | 1/2000 | Mollison | |
| 6,074,659 A | 6/2000 | Kunz et al. | |
| 6,090,996 A | 7/2000 | Li | |
| 6,091,980 A | 7/2000 | Squire et al. | |
| 6,117,166 A | 9/2000 | Winston et al. | |
| 6,136,961 A | 10/2000 | Dordick et al. | |
| 6,162,247 A | 12/2000 | Weadock et al. | |
| 6,171,609 B1 | 1/2001 | Kunz | |
| 6,179,858 B1 | 1/2001 | Squire et al. | |
| 6,206,931 B1 | 3/2001 | Cook et al. | |
| 6,224,794 B1 | 5/2001 | Amsden et al. | |
| 6,268,390 B1 | 7/2001 | Kunz | |
| 6,273,913 B1 | 8/2001 | Wright et al. | |
| 6,306,421 B1 | 10/2001 | Kunz et al. | |
| 6,323,184 B1 | 11/2001 | Zalewski et al. | |
| 6,326,017 B1 | 12/2001 | Mayberg | |
| 6,328,762 B1 | 12/2001 | Anderson et al. | |
| 6,329,386 B1 | 12/2001 | Mollison | |
| 6,333,347 B1 | 12/2001 | Hunter et al. | |
| 6,358,989 B1 | 3/2002 | Kunz et al. | |
| 6,391,333 B1 | 5/2002 | Li et al. | |
| 6,491,938 B2 | 12/2002 | Kunz et al. | |
| 6,515,009 B1 | 2/2003 | Kunz et al. | |
| 6,534,693 B2 * | 3/2003 | Fischell ............ | A61B 17/06166 602/43 |
| 2001/0027340 A1 | 10/2001 | Wright et al. | |
| 2002/0026236 A1 | 2/2002 | Helmus et al. | |

FOREIGN PATENT DOCUMENTS

| | | |
|---|---|---|
| WO | 93/23013 | 11/1993 |
| WO | 9638188 | 12/1996 |
| WO | 0024412 | 5/2000 |
| WO | WO 00/24436 | 5/2000 |
| WO | 02/36054 | 5/2002 |

OTHER PUBLICATIONS

Abizaid, A.A., et al., "Sustained suppression of neointimal proliferation late (1 yr) after implantation of sirolimus-eluting bx-velocity stent," *Circulation*, Suppl II v104:17, abstract 2201 (Oct. 2001).

Akers, D.L., et al., "The effect of carbon coating and porosity on early patency of expanded polytetrafluoroethylene grafts: an experimental study," *J Vasc Surg*, 18(1):10-15 (Jul. 1993) PMID: 8326650 [PubMed-indexed for MEDLINE] Abstract.

(56) References Cited

OTHER PUBLICATIONS

Anain, P., et al., "Balloon angioplasty for arteriovenous graft stenosis," *J Endovasc Ther*, 8(2):173-176 (2001) PMID: 11357977 [PubMed-indexed for MEDL1NE] Abstract.

Angiotech Pharmaceuticals, Inc., Vancouver, BC., CA, "Angiotech signs license and development agreement with C.R. Bard, Inc.," Angiotech website www.angiotech.com (Dec. 22, 1998).

Arnold, et al., "Thrombolytic therapy of synthetic graft occlusions before vascular reconstructive procedures," *Am J. Surg*, 164(3):241-247 (Sep. 1992). PMID: 1415923 [PubMed-indexed for MEDLINE] Abstract.

Arsenault, A.L., et al:, "Taxol (paclitaxel) involution of articular cartilage destruction in collagen induced arthritis: an ultrastructural demonstration of an increased superficial chondroprotective layer," *J Rheumatol*, 27(32):582-588 (Mar. 2000) PMID: 10743793 [PubMed-indexed for MEDLINE] Abstract.

Axel, D.I., et al., "Paclitaxel inhibits arterial smooth muscle cell proliferation and migration in vitro and in vivo using local drug delivery," *Circulation*, 96(2):636-645 (Jul. 1997). (© Am. Heart Assoc.) PMID: 9244267 [PubMed-indexed for MEDLINE] Abstract.

Bailey, S., "Local drug delivery during percutaneous coronary intervention," *Curr Interv Cardiol* Rep, 2(4):349-357 (Nov. 2000) PMID: 11096686 [PubMed-indexed for MEDLINE] Abstract.

Balon, H., et al., "Scintigraphic demonstration of restored Denver peritoneovenous shunt patency using urokinase," *Clin Nucl Med*, 14(4):310-311 (1989) PMID: 2706879 [PubMed-indexed for MEDLINE] No Abstract.

Bandyk, D.F., "Thrombolysis in peripheral arterial graft occlusion," *Can J Surg*, 36(4):372-378 (1993) PMID: 8370020 [PubMed-indexed for MEDLINE] Abstract.

Barth, et al., "Hydrodynamic thrombectomy system versus pulse-spray thrombolysis for thrombosed hemodialysis grafts: a multicenter prospective randomized comparison," *Radiology*, Declaration, 217(3):678-684 (2000) PMID: 11110928 [PubMed-indexed for MEDLINE] Abstract.

Barzel, E., "Use of a simple compression dressing obtain hemostasis after pharmacologic throbolysis of dialysis grafts," *J Vas Interv Radiol*, 10(8):1039-1042 (1999) PMID: 10496705 [PubMed-indexed for MEDLINE] No Abstract.

Beathard, G.A., "Thrombolysis versus surgery for the treatment of thrombosed dialysis access grafts," *J. Am Soc Nephrol*, 6(6):1619-1624 (1995) PMID: 8749689 [PubMed-indexed for MEDLINE].

Beathard, G.A., "Mechanical versus pharmacomechanical thrombolysis for the treatment of thrombosed dialylis access grafts," *Kidney Int*,. 45(5):1401-1406 (May 1994) PMID: 8072252 [PubMed-indexed for MEDLINE] Abstract.

Beathard, et al., "Endovascular management of thrombosed dialysis access grafts," *Am J Kidney Disx..*, 32(1):172-175 (Jul. 1998). PMID: 9669441 [PubMed-indexed for MEDLINE] No Abstract.

Beathard, G.A., "Gianturco self-expanding stent in the treatment of stenosis in dialysis access grafts," *Kidney Int*, 43(4):872-877 (Apr. 1993) PMID: 8479123 [PubMed-indexed for MEDLINE] Abstract.

Becquemin, J.P., et al., "Evaluation of a polyester collagen-coated heparin bonded vascular graft," *J Cardiovasc Surg*, 38(1):7-14 (Feb. 1997) Abstract.

Belkin, M., et al., "Observations on the use of thrombolytic agents for thrombotic occlusion of infrainguinal vein grafts," *J Vasc Surg*, 11(2):289-294 (1990) PMID: 2299748 [Pub-Med-indexed for MEDLINE] Abstract.

Bengtsson, L., et al., "A new and simple technique to achieve a confluent and flow resistant endothelium on vascular ePTFE-grafts using human serum," *Eur J Vasc Surg*, 8(2):182-187 (Mar. 1994) Abstract.

Berceli, S.A., et al., "Evaluation of a novel hirudin-coated polyester graft to physiologic flow conditions: hirudin bioavailability and thrombin uptake," *J Vasc Surg*, 27(6):1117-1127 (Jun. 1998). PMID: 9652474 [PubMed-indexed for MEDLINE] Abstract.

Berger, et al., "Recurrent thrombosis of polytetrafluoroethylene dialysis fistulas after recent surgical thrombectomy: salvage by means of thrombolysis and angioplasty," *J Vasc Interv Radiol*; 5(5):725-730 (Sep.-Oct. 1994) PMID: 8000121 [PubMed-indexed for MEDLINE] Abstract.

Berkowitz, H.D., "Regarding Thrombolysis of occluded infrainguinal vein grafts: predictors of outcome" *J Vasc Surg*, 27(1):192-193 (1998) PMID: 9474103 [PubMed-indexed for MEDLINE] No Abstract.

Bernex, F., et al., "In vitro endothelialization of carbon-coated Dacron vascular grafts," *Int J Artif Organs*, 15(3):172-180 (Mar. 1992) PMID: 1387867 [PubMed-indexed for MEDLINE]. Abstract.

Berridge, D.C., et al., "Thrymbolysis in arterial graft thrombosis," *Eur J Vasc Endovasc Surg*, 9(2):129-132 (1995) PMID: 7627644 [PubMed-indexed for MEDLINE] Abstract.

Besarab, A., et al., "Measuring the adequacy of hemodialysis access," *Curr Opin Hephrol Hypertens*, 5(6):527-531 (1996) PMID: 8979002 [PubMed-indexed for MEDLINE] Abstract.

Bhatnagar, P.K., et al., "The impact of thrombolytic therapy on arterial and graft occlusions: a critical analysis," *J Cardiovasc Surg*, 37(2):105-112 (1996) PMID: 8675513 [PubMed-indexed for MEDLINE] Abstract.

Billmann, P., et al., "Local fibrinolytic therapy in thrombotic complications of peritoneovenous shung," *Z Gastroenterol*, 24(8):426-429 PMID: 3765747 [PubMed-indexed for MEDLINE] Abstract.

Bitar, G., "Balloon versus patch angioplasty as an adjuvant treatment to surgical thrombectomy of hemodialysis grafts," *Am J Surg*, 174(2):140-142 (Aug. 1997) PMID: 9293830 [PubMed-indexed for MEDLINE] Abstract.

Bjarnason, H., et al., "Iliofemoral deep venous thrombosis: safety and efficacy outcome during 5 years of catheter-directed thrombolytic therapy," *J Vasc Interv Radiol*, 8(3):405-418 (1997) PMID: 9152914 [PubMed-indexed for MEDLINE] Abstract.

Bookstein, J.J., "Is comparison of mechanical versus pulse-spray thrombolysis in dogs highly relevant clinically?" *Radiol*, 202(1):31-32 (1997) PMID; 8988187 [PubMed-indexed for MEDLINE] No Abstract.

Bookstein, J.J., et al., "Pulse-spray pharmacomechanical thrombolysis," *Cariovasc Intervent Radiol*, 15(4):228-233 (1992) PMID: 1394359 [PubMed-indexed for MEDLINE] Abstract.

Bookstein, J.J., et al., "Pulsed-spray pharmacomechanical thrombolysis preliminary clinical results," *AJR Am J Roentgenol*, 152(5):1097-1100 (1989) PMID: 2705344 [PubMed-indexed for MEDLINE] Abstract.

Borkowski-Weller, D.M., "Urokinase: restoring circulation without surgery," 53(10):44-50 (1990) PMID: 2218324 [PubMed-indexed for MEDLINE] No Abstract.

Bos, G.W., et al., "Adherence and proliferation of endothelial cells on surface-immobilized albumin-heparin conjugate," *Tissue Eng*, 4(3):267-279 (Fall 1998) PMID: 9836790 [PubMed-indexed for MEDLINE]Abstract.

Brattich, M., Vascular access thrombosis: etiology and prevention, *Anna J*, 26(5):537-540 (Oct. 1999) PMID: 10776083 [PubMed-indexed for MEDLINE] Abstract.

Breathard, G.A., "Thrombolysis versus surgery for the treatment of thrombosed dialysis access grafts," *J Am Soc Nephrol*, 6(6):1916 (1995) PMID: 8749689 [PubMed-indexed for MEDLINE] Abstract.

Breathard, G.A., "Mechanical versus pharmacomechanical thrombolysis for the treatment of thrombosed dialysis access grafts," *Kidney Int*, 45(5):1401-1405 (1994) PMID: 8072252 [PubMed-indexed for MEDLINE] Abstract.

Brethard, G.A., et al., "Mechanical thrombolysis for the treatment of thrombosed hemodialysis access grafts," *Radiology*, 200(3):711-716 (1996) PMID: 8756920 [PubMed-indexed for MEDLINE] Abstract.

Brethard, G.A., "Endovascular management of thrombosed dialysis access grafts," *Am J Kidney Dis*, 32(1):172-175 (1998) PMID: 9669441 [PubMed-indexed for MEDLINE] No Abstract.

Briefel, G.R., et al. "Cerebral embolism after mechanical thrombolysis of a clotted hemodialysis access," *Am J Kidney Dis*, 34(2):341-343 (1999) PMID: 10430984 [PubMed-indexed for MEDLINE] Abstract.

Brotman, D.N., et al., "Hemodialysis graft salvage," *J Am Coll Surg*, 178(5):431-434 (1994) PMID: 8167878 [PubMed-indexed for MEDLINE] Abstract.

Brown, M.C., "An adverse interaction between warfarin and 5-fluorouracil: A case report and review of the literature," *Chemo-*

(56) References Cited

OTHER PUBLICATIONS therapy, 45(5):392-395 (Sep.-Oct. 1999) PMID: 10473927 [PubMed-indexed for MEDLINE] Abstract.
Brunner, M.C., et al. "Ultrarapid urokinase in hemodialysis access occlusion," *J Vasc Interv Radiol*, 2(4):503-506 (1991) PMID: 1797216 [PubMed-indexed for MEDLINE] Abstract.
Brunner, M.C., et al. "Acute arterial occlusion: surgical thrombectomy versus local thrombolysis—preliminary status determination from the interdisciplinary viewpoint," *Vasa*, 15(2)158-161 (1986) PMID: 2941930 [PubMed-indexed for MEDLINE] No Abstract.
Camerini, E., et al., "Loco-regional transcatheter thrombolysis," *Radiol Med*, 79(3):244-246 (1990) PMID: 2336482 [PubMed-indexed for MEDLINE] Abstract.
Cantelmo, N.L., Quist W.C., Lo Gerfo, F.W., "Quantitative analysis of anastomosis intimal hyperplasia in paried Dacron and PTFE grafts," *J Cardiovasc Surg.*, (Torino), 30:910-915 (1989) PMID: 2532216 [PubMed-indexed for MEDLINE] Abstract.
Caputo, R.P., et al., "Extravasation of thrombus into the aortic root: a complication following use of an infusion catheter for intragraft thrombolysis," *Cathet Cardiovasc Diagn*, 37(3):263-266 (1996) PMID: 8974802 [PubMed-indexed for MEDLINE] Abstract.
Cassel, W.S., et al., "An animal model for small-diameter arterial grafts," *J Invest Surg*, 2(2):181-186 (1989) Abstract.
Castaneda, F., et al., "New trhombolytic brush catheter in thrombosed Upolytetrafluoroethylene dialysis grafts: preclinical animal study," *J Vasc Interv RVadiol*, 9(5):793-798 (1998) . PMID: 9756069 [PubMed-indexed for MEDLINE] Abstract.
Chalmers, R.T., et al., "The effect of an intraluminal stent on neointimal hyperplasia at an end-to-side polytebafluoreothylene graft arterial anastomosis," *Am J Surg*, 168(2):85-90 (Aug. 1994) PMID: 7519832 [PubMed-indexed for MEDLINE] Abstract.
Chalmers, R.T., et al., "Late results of a prospective study of direct intra-arterial urokinase infusion for peripheral arterial and bypass graft occlusions," *Cardiovasc Surg*, 3(3)293-297 (1995) PMID: 7655844 [PubMed-indexed for MEDLINE] Abstract.
Chao-Wei, H., et al., "Physiological transport forces govern drug distribution for stent-based delivery," *Circulation*, 104:600-605 (2001) Abstract.
Chen, C., et al., "Phosphoryclcholine coating of ePTFE grafts reduces neointimal hyperplasia in canine model," *Ann Vasc Surg*, 11(1):74-79 (Jan. 1997) PMID: 9061143 [PubMed-indexed for MEDLINE] Abstract.
Chen, C., et al., "Graft rescue for haemodialysis arterio-venous grafts: is it worth doing and which factors predict a good outcome?" *J R Coll Surg Edinb*, 43(4)248-250 (1998) PMID: 9776640 [PubMed-indexed for MEDLINE] Abstract.
Christensen, E.D., et al., "Local intra-arterial thrombolysis with urokinase combined with balloon angioplasty in the lower extremities," *Eur J Surg*, 160(11):593-597 (1994) PMID: 7858043 [PubMed-indexed for MEDLINE] Abstract.
Churchill, D.N., et al., "Probability of thrombosis of vascular access among hemodialysis patients treated with recombinant human erythropoietin," *J Am Soc Nephrol*; 4:1809-1813 (1994) PMID: 8068879 [PubMed-indexed for MEDLINE] Abstract.
Cinat, M.E., et al., "A prospective evaluation of PTFE graft patency and surveillance techniques in hemodialysis access, " *Ann Vasc Surg*, 13(2):191-198 (Mar. 1999) PMID: 10072461 [PubMed-indexed for MEDLINE] Abstract.
Clarke, A.M., et al., "An evaluation of expanded polytetrafluoroethylene (PTFE) loop grafts in the thigh as vascular access for haemodialysis in patients with access problems," *Ann R Coll Surg Engl*, 71(3):204 (1989) PMID: 2589788 [PubMed-indexed for MEDLINE] No Abstract.
Clowes, A.W., et al., "Mechanisms of arterial graft failure. 1. Role of cellular proliferation in early healing of PTFE prostheses," *Am J Pathol*, 118(1):43-54 (Jan. 1985) PMID: 3966536 [PubMed-indexed for MEDLINE] Abstract.
Clowes, A.W., et al., "Mechanisms of arterial graft failure. II. Chronic endothelial and smooth muscle cell proliferation in healing polytetrafluoroethylene prostheses," *J Vasc Surg*, 3(6):877-884 (Jun. 1986) PMID: 3712635 [PubMed-indexed for MEDLINE] Abstract.

Cohen, et al., "Improved treatment of thrombosed hemodialysis access sites with thrombolysis and angioplasty," *Kidney Int.*; 46(5):1375-1380 (Nov. 1994). PMID: 7853796 [PubMed-indexed for MEDLINE] Abstract.
Cohen, G.S., et al., "External beam irradiation as an adjunctive treatment in failing dialysis shunts," *J Vasc Interv Radiol*, 11(3):321-326 (Mar. 2000) PMID: 10735426 [PubMed-indexed for MEDLINE] Abstract.
Cohn, D., et al., "Introducing a selectively biodegradable filament wound arterial prosthesis: a short-term implantation study," *J Biomed Mater Res*, 26(9):1184-1204 (Sep. 1992) PMID: 1429766 [PubMed-indexed for MEDLINE] Abstract.
Coleman, C.C., et al., "Mechanical thrombectomy: results of early experience," *Radiology*, 189(3):803-805 (1993) PMID: 8234707 [PubMed-indexed for MEDLINE] Abstract.
Comerota, A.J., et al., "Results of a prospective, randomized trial of surgery versus thrombolysis for occluded lower extremity bypass grafts," *Am J Surg*, 172(2):105-112 (1996) PMID: 8795509 [PubMed-indexed for MEDLINE] Abstract.
Cook, T.A., et al., "Accelerated peripheral arterial thrombolysis using pulse-spray thrombolysis (PST)," *Eur J Vasc Endovarc Surg*, 9(3):362-363 (1995) PMID: 7620969 [PubMed-indexed for MEDLINE] No Abstract.
Cragg, A.H., et al., "Two urokinase dose regimens in native arterial and graft occlusions: initial results of a prospective, randomized clinical trial," *Radiology*, 178(3):681-686 (1991) PMID: 1994402 [PubMed-indexed for MEDLINE] Abstract.
Creel, C.J., et al., "Arterial paclitaxel distribution and deposition," *Circulation Research*, 86(8):879-884 (Apr. 2000) (© Am. Heart Assoc.) PMID: 10785510 [PubMed-indexed for MEDLINE] Abstract.
Crook, M.F., et al., "Expression of intercellular adhesion molecules in human saphenous veins: effects of inflammatory of cytokines and neointima formation in culture," *Atherosclerosis*, 150(1):33-41 (May 2000) PMID: 10781633 [PubMed-indexed for MEDLINE] Abstract.
Cull, D.L., et al., "The impact of a community-wide vascular access program on the management of graft thromboses in a dialysis population of 495 patients," *Am J Surg*, 178(2):113-116 (1999) PMID: 10487260 [PubMed-indexed for MEDLINE] Abstract.
Culp, K., et al., "Vascular access thrombosis in new hemodialysis patients," *Am J Kidney Dis.*; 26:341-346 (1995) PMID: 7645539 [PubMed-indexed for MEDLINE] Abstract.
Curl, G.R., et al., "Beneficial effect of aspirin in maintaining the patency of small-caliber prosthetic grafts after thrombolysis with urokinase or tissue-type plasminogen activator," *Circulation*, 74(2 Pt 2):I21-4 (1986) PMID: 3091289 [PubMed-indexed for MEDLINE] Abstract.
Cynamon, J., et al., "Hemodialysis graft declotting: description of the "lyse and wait" technique," *J Casc Interv Radiol*, 8(5):825-829 (1997) PMID: 9314374 [PubMed-indexed for MEDLINE] No Abstract.
Dacey, L.J., et al., "Cost-effectiveness of intra-arterial thrombolytic therapy," *Arch Surg*, 123(10):1218-1223 (1988) PMID: 3140762 [PubMed-indexed for MEDLINE] Abstract.
Darcy, M.D., et al., "Percutaneous revision of an acutely thrombosed transjugular intrahepatic portosystemic shunt," *J Vasc Interv Radiol*, 3(1):77-80 (1992) PMID: 1540716 [PubMed-indexed for MEDLINE] No Abstract.
Davis, et al., "Thrombosed dialysis grafts: efficacy of intrathrombic deposition of concentrated urokinase, clot maceration, and angioplasty," *AJR Am J Roentgenol*, 149(1):177-181 (Jul. 1987). PMID: 2954441 [PubMed-indexed for MEDLINE] Abstract.
Dehio, C. et al., "Interaction of Bartonella henselae with endothelial cells results in bacterial aggregation on the cell surface and the subsequent engulfment and internalisation of the bacterial aggregate by a unique structure, in the invasome," *J Cell Sci*, 110(Pt 18):2141-2154 (Sep. 1997) PMID: 9378764 [PubMed-indexed for MEDLINE] Abstract.
Dekker, A., et al., "Improved adhesion and proliferation of human endothelial cells on polyethylene precoated with monoclonal antibodies directed against cell membrane antigens and extracellular matrix proteins," *Thromb Haemost*, 66(6):715-724 (Dec. 1991) PMID: 1796417 [PubMed-indexed for MEDLINE] Abstract.
De la Fuente, L.M., at al., "Initial results of the Quanam drug-eluting stent (QuaDS-QP-2). Registry (BARDDS) in human sub-

(56) References Cited

OTHER PUBLICATIONS jects," *Catheter Cardiovasc Interv*, 53(4):480-488 (Aug. 2001) PMID: 11514998 [PubMed-indexed for MEDLINE] Abstract.
De Maioribus, C.A., "A reevaluation of intraarterial thrombolytic therapy for acute lower extremity ischemia," *J Vasc Surg*, 17(5):888-895 (1993) PMID: 8487357 [PubMed-indexed for MEDLINE] Abstract.
De Scheerder, I., et al., "Treatment of in-stent restenosis using paclitaxel eluting stents: a single centre pilot trial," *Circulation*, Suppl II; v104:17, abstract 3503 (Oct. 2001).
Deutsch, M., et al., "Clinical autologous in vitro endothelialization of infrainguinal ePTFE grafts in 100 patients: a 9-year experience," *Surgery*, 126(5):847-855 (Nov. 1999) PMID: 10568184 [PubMed-indexed for MEDLINE] Abstract.
Diskin, C.J., et al., "The importance of timing of surgery for hemodialysis vascular access thrombectomy," *Nephron*, 75(2):233-237 (1997) . PMID: 90415498 [PubMed-indexed for MEDLINE] Abstract.
Docci, D., et al., "Successful declotting of arteriovenous grafts with local infusion of urokinase in hemodialyzed patients," *Artif Organs*, 10(6):494-496 (1986) PMID: 3800707 [PubMed-indexed for MEDLINE] Abstract.
Doi, K., et al., "Significance of porosity and compliance of microporous, polyurethane-based microarterial vessel on neoarterial wall regeneration," *J Biomed Mater Res*, 37(4):573-584 (Dec. 19997) PMID: 9407307 [PubMed-indexed for MEDLINE] Abstract.
Doi, K., et al., "Enhanced vascularization in a microporous polyurethane graft impregnated with basic fibroblast growth factor and heparin," *J Biomed Mater Res*, 34(3):361-370 (Mar. 1997) PMID: 9086406 [PubMed-indexed for MEDLINE] Abstract.
Dolmatch, B.L., et al., "Synthetic dialysis shunts: thrombolysis with the Cragg thrombolytic brush catheter," *Radiology*, 213(1):180-184 (1999) PMID: 10540659 [PubMed-indexed for MEDLINE] Abstract.
Dolmatch, B.L., et al., "Treatment of anastomotic bypass graft stenosis with directional atherectomy: short-term and intermediate-term results," *J Vasc Interv Radiol*, 6(1):105-113 (1995) PMID: 7703574 [PubMed-indexed for MEDLINE] Abstract.
Dolmatch, B.L., et al., "Will iatrogenic pulmonary embolization be our pulmonary embarrassment?" *Radiology*, 191(3):615-617 (1994) PMID: 8184035 [PubMed-indexed for MEDLINE] No Abstract.
Dorros, G., et al., "Urokinase infusion of chronically occluded femoropopliteal Gortex bypass grafts vial popliteal approach," *Cathet Cardiovasc Diagn*, 24(3):197-203 (1991) PMID: 1764742 [PubMed-indexed for MEDLINE] Abstract.
Doughtery, et al., "Endovascular versus surgical treatment of thrombosed hemodialysis grafts: A prospective, randomized study," *J Vasc Surg*, Declaration: 30(6):1016-1023 (1999) PMID: 10587385 [PubMed-indexed for MEDLINE] Abstract.
Dracbman, D.E., et al., "Neointimal thickening after stent delivery of paclitaxel: change in composition and arrest of growth over six months," *J Am Coll Cardiol*, 35(7):2325-2332 (Dec. 2000) PMID: 11127480 [PubMed-indexed for MEDLLINE] Abstract.
Durham, J.D., et al., "Regional infusion of urokinase into occluded lower-extremity bypass grafts: Long-term clinical results," *Radiology*, 172(1):83-87 (1989) PMID: 2740523 [PubMed-indexed for MEDLINE] Abstract.
Duszak, R., et al., "Pitfalls that may contribute to "lyse and wait" declotting failures," *J Vasc Interv Radiol*, 9(4):660; discussion 661(1998) PMID: 9684841 [PubMed-indexed for MEDLINE] No Abstract.
Duszak, R., Jr., et al., "Dialysis graft declotting with very low dose urokinase: is it feasible to use 'less and wait?'" *J Vasc Interv Radiol*, 10(2 pt 1):123-128 (1999) PMID: 10082097 [PubMed-indexed for MEDLINE] Abstract.
Edelman, E.R., et al., "Effect of controlled adventitial heparin delivery on smooth muscle cell proliferation following endothelial injury," *Proc Natl Acad Sci USA*, 87(10):3773-3777 (May 1990) PMID: 2339120 [PubMed-indexed for MEDLINE] Abstract.

Edwards, N., "Molecule of the month-taxol" School of Chemistry University of Bristol, www.bris.ac.uk/Depts/Chemistry/MOTM/taxol.htm.
Eisenbud, D.E., et al., "Treatment of acute vascular occlusions with intra-arterial urokinase," *Am J Surg*, 160(2)160-164 (1990) PMID: 2382768 [PubMed-indexed for MEDLINE] Abstract.
Ejaz, A.A., et al., "Hemorrhagic bullae as a complication of urokinase therapy for hemodialysis catheter thrombosis," *Am J Nephrol*, 15(2):178-179 (1995) PMID: 7733160 [PubMed-indexed for MEDLINE] No Abstract.
El Sharouni, S.Y., et al., "Endovascular brachytherapy in arteriovenous grafts for haemodialysis does not prevent development of stenosis," *Radiother Oncol*, 49(2):199-200 (1998) PMID: 10052888 [PubMed-indexed for MEDLINE] No Abstract.
Enea, N.A., et al. "Hemodialysis graft declotting: 'lyse and wait' and watch," *J Vasc Interv Radiol*, 9(4):660-661 (1998) PMID: 9684842 [PubMed-indexed for MEDLINE] No Abstract.
Ettenson, D.S., el al., "Local drug delivery an emerging approach in the treatment of restenosis," *Vasc Med*, 5(2):97-102 (2000) PMID: 10943586 [PubMed-indexed for MEDLINE] Abstract.
Faggioli, G.L., et al., "Failure of thrombolytic therapy to improve long-term vascular patency," *J Vasc Surg*, 19(2):289-296 (1994) PMID: 8114190 [PubMed-indexed for MEDLINE] Abstract.
Falk, A., et al., "Thrombolysis of clotted hemodialysis grafts with tissue-type plasminogen activator," *J Vasc Interv Radiol*, 12(3):305-311 (2001) PMID: 11287506 [PubMed-indexed for MEDLINE] Abstract.
Farner, M.C., "Endovascular versus surgical treatment for thrombosed hemodialysis: a prospective, randomized study," *J Vasc Surg*, 32(5):1038-1039 (2000) PMID: 11054238 [Pub-Med-indexed for MEDLINE] No Abstract.
Feldman, H.I., et al., "Hemodialysis vascular access morbidity in the United States," *Kidney Int*., 3(43):1091-1096 (1993).
Ferron, G.M., et al., "Lipophilic benzamide and anilide derivatives as high-performance liquid chromatography internal standard: application to sirolimus (rapamycin) determination," *J Chroma B Biomed Sci Appl*, 703;243-251 (Dec. 1997) PMID: 9448082 [PubMed-indexed for MEDLINE] Abstract.
Frisch, N., et al., "Thrombectomy or thrombolysis in the treatment of proximal phlebitis. Functional long term results," *J Mal Vasc*, 14(4):294-298 (1989) PMID: 2584885 [PubMed-indexed for MEDLINE] Abstract.
Funaki, et al., "Wallstent deployment to salvage dialysis graft thrombolysis complicated by venous rupture: early and intermediate results," *AJR Am J Roentgenol*, 169(5):1435-1437 (Nov. 1997). PMID: 9353476 [PubMed-indexed for MEDLINE].
Galland, R.B., et al., "Patency following successful thrombolysis of occluded vascular grafts," *Eur J Vasc Endovasc Surg*,22(2):157-160 (2001) PMID: 11472050 [PubMed-indexed for MEDLINE] Abstract.
Gallo, R., et al., "Inhibition of intimal thickening alter balloon angioplasty in porcine coronary arteries by targeting regulators of the cell cycle," *Circulation*, 99:2164-2170 (1999) PMID: 10217658 [PubMed-indexed for MEDLINE] Abstract.
Gardiner, et al., "Thrombolysis of occluded femoropopliteal grafts,"*AJR Am J Roentgenol*.; 124(3):621-626 (Sep. 1986). PMID: 3488664 [PubMed-indexed for MEDLINE] Abstract.
Gardiner, G.A., Jr., et al., "Salvage of occluded arterial bypass grafts by means of thrombolysis," *J Vasc Surg*, 9(3):426-431 (1989) PMID: 2921792 [PubMed-indexed for MEDLINE] Abstract.
Gardiner, G.A., Jr., "Thrombolysis of occluded arterial bypass grafts," *Cardiovasc Intervent Radiol*, 11 Suppl:S58-9 (1988) PMID: 3131009 [PubMed-indexed for MEDLINE] Abstract.
Gaylord, G.M. et al., "Long-term hemodialysis access salvage: problems and challenges for nephrologists and interventional radiologists," *J Vasc Interv Radiol*, 4(1):103-107 (1993) PMID: 8425086 [PubMed-indexed for MEDLINE] No Abstract.
Gazitt, Y., "TRAIL is a potent inducer of apoptosis in myeloma cells derived from multiple myeloma patients and is not cytotoxic to hematopoietic stem cells" *Leukemia*, 13(11):1817-1824 (Nov. 1999) PMID: 9735415 [PubMed-indexed for MEDL1NE] Abstract.
Gazitt, Y., et al., "Bcl-2 overexpression is associated with resistance to paclitaxel, but not gemcitabine, in multiple myeloma cells," *Int J Oncol*, 13(4):839-848 (Oct. 1998) Abstract.

(56) References Cited

OTHER PUBLICATIONS

Gelbfish, G.A., "Surgery versus percutaneous treatment of thrombosed dialysis access grafts: is there a best method?" *J Vasc Interv Radiol*, 9(6):875-877 (1998) PMID: 9840030 [PubMed-indexed for MEDLINE] No Abstract.

Gelderblom, H. et al., "Disposition of [G-(3)H] paclitaxel and cremophor EL in a patient with severely impaired renal function," *Drug Metab Dispos*, 27(11):1300-1305 (Nov. 1999) PMID: 10534315 [PubMed-indexed for MEDLINE] Abstract.

Gherardini, G., et al., "Cell adhesion and short-term patency in human endothelium presceded 1.5-mm polytetratluoroethylene vascular grafts: an experimental study," *Plast Reconstr Surg*, 99(2):472-478 (Feb. 1997) PMID: 9030157 [PubMed-indexed for MEDLINE] Abstract.

Gillis, C., et al., "Secretion of prostacyclin, tissue plasminogen activator and its inhibitor by cultured adult human endothelial cells grown on different matrices," *Eur J Vasc Endovasc Surg*,11(2):127-133 (Feb. 1996) PMID: 8616641 [PubMed-indexed for MEDLINE] Abstract.

Gmelin E., Winterhoff, R., Rivast, E., "Insufficient hemodialysis access fistulas: late results of treatment with percutaneous hollow angioplasty," *Radiology*, 171:657-660 (1989) PMID: 2524085 [PubMed-indexed for MEDLINE] Abstract.

Goodwin, et al., "Dialysis access graft thrombolysis: randomized study of pulse-spray versus continuous urokinase infusion;" 21(2):135-137 (Mar.-Apr. 1998). PMID: 9502680 [PubMed-indexed for MEDLINE] Abstract.

Gordon, D.H., et al, "Treatment of stenotic lesions in dialysis access fistulas and shunts by PTA," *Radiology*; 143:53-58 (1982) PMID: 6461027 [PubMed-indexed for MEDLINE] No Abstract.

Gorriz, J.L., et al., "Endoluminal percutaneous thrombectomy as a treatment for acute vascular access thrombosis: long-term results of 123 procedures," *Nefrologia*, 21(2):182-190 (2001) PMID: 11464652 [PubMed-indexed for MEDLINE] Abstract.

Gouffrant, J.M., et al., "Ambulatory thrombectomy of a graft Transcutaneous clamping," *J Chir (Paris)*, 123(5):366-367 (1986) PMID: 3745325 [PubMed-indexed for MEDLINE] Abstract.

Gray, R., et al., "Use of Wallstents for hemodialysis access-related venous stenoses and occlusions untreatable with balloon angioplasty, " *Radiology*; 195:479-484 (1995) PMID: 7724770 [PubMed-indexed for MEDLINE] Abstract.

Gray, R., "Prospective randomized comparison of surgical versus endovascular management of thrombosed dialysis access grafts," *J Vasc Surg*, 27(2):392-393 (1998) PMID: 9510303 [PubMed-indexed for MEDLINE] No Abstract.

Gray, R.J., "Percutaneous intervention for permanent hemodialysis access: a review," *J Vasc Interv Radiol*, 8(3):313-327 (1997) PMID: 9152902 [PubMed-indexed for MEDLINE] No Abstract.

Gray, R.J.,. "Reporting standards for percutaneous interventions in dialysis access. Technology Assessment Committee," *J Vasc Interv Radiol*, 10(10):1405-1415 (1999) PMID: 10584659-indexed for MEDLINE] No Abstract.

Greenberg, R.K., et al., "Mechanical versus chemical thrombolysis: an in vitro differentiation of thrombolytic mechanisms,"*J Vasc Interv Radiol*, 22(2 Pt 1)199-205 (2000) PMID: 10716390 [PubMed-indexed for MEDLINE] Abstract.

Grube, E., et al., "Taxus I: prosepctive, randomized, double-blind comparison of NIRx™ stents coated with paclitaxel in a polymer carrier in de-novo coronary lesions compared with uncoated controls," *Circulation*, Suppl II; v104:17, abstract 2197 (Oct. 2001).

Gruss, J.D., et al., "Experiences with adjuvant prostaglandin therapy in vascular surgery interventions," *Vasa Suppl*, 33:353-354 (1991) PMID: 1788755 [PubMed-indexed for MEDLINE] Abstract.

Guenther, R.W., et al., "Aspiration catheter for percutaneous thrombectomy: clinical results," *Radiology*, 175(1):271-273 (1990) PMID: 2315493 [PubMed-indexed for MEDLINE] Abstract.

Gunther, R.W., "Thrombosed hemodialysis grafts," *Radiology*, 198(3):908-909 (Mar. 1996). PMID: 8628894 [PubMed-indexed for MEDLINE] No Abstract.

Haegerstrand, A., et al., "Serum proteins provide a matrix for cultured endothelial cells on expanded polytetrafluoroethylene vascular grafts," *Scand J Thorac Cardiovasc Surg*, 27(1):21-26 (1993) PMID: 8493492 [PubMed-indexed for MEDLINE] Abstract.

Hall, J.D., et al., "Effect of controlled local acetylsalicylic acid release on in vitro platelet adhesion to vascular grafts," *J Biomater Appl*, 8(4):361-384 (Apr. 1994) PMID: 8064590 [PubMed-indexed for MEDLINE] Abstract.

Hamdan, A.D., et al., "Evaluation of anastomotic hyperplasia progression using the cyclin specific antibody MIB-1," *Am J Surg*, 172(2):168-171 (Aug. 1996) PMID: 8795523 [PubMed-indexed for MEDLINE] Abstract.

Han, D.K., et al., "In vivo canine studies of a Sinkhole valve and vascular graft coated with biocompatible PU-PEO-SO3," *ASAIO J*, 39(3):M537-41 (Jul.-Sep. 1993) PMID: 8268593 [PubMed-indexed for MEDLINE] Abstract.

Hansen, A.K., et al., "Local intra-arterial thrombolysis. Results in arterial throboses and graft occlusions," *Ugeskr Laeger*, 159(130:1950-1953 (1997) PMID: 9123634 [PubMed-indexed for MEDLINE] Abstract.

Haque, M.I., et al., "Bioadsorption of chitosan adsorbable vascular template," *Curr Surg*, 51:77-80 (2001) PMID: 11226542 [PubMed-indexed for MEDLINE] Abstract.

Harpaz, D., et al., "Ultrasound accelerates urokinase-induced thrombolysis and reperfusion," *Am Heart J*, 127(5):1211-1219 (1994) PMID: 8172048 [PubMed-indexed for MEDLINE] Abstract.

Harrell, D.S., et al., "Admixtare of heparin with urokinase to decrease thrombolysis time and urokinase dose in polytetrafluoroethylene dialysis graft recanalization,"*J Vasc Interv Radiol*, 7(2):193-197 (1996) PMID: 9007797 [PubMed-indexed for MEDLINE] Abstract.

Hartmann, J.R., et al., "Prolonged infusion of urokinase for recanalization of chronically occluded aortocoronary bypass grafts," *Am J Cardiol*, 61(1):189-191 (1988) PMID: 3257348 [PubMed-indexed for MEDLINE] No Abstract.

Hartmann, J.R., "Urokinase recanalization of chronically occluded aortocoronary vein grafts," *Coron Artery Dis*, 7(9):641-648 (1996) PMID: 8950494 [PubMed-indexed for MEDLINE] Abstract.

Hathaway, P.B., et al., "The apex-puncture technique for mechanical thrombolysis of loop hemodialysis grafts," *J Vasc Interv Radiol*, 10(6):775-779 (1999) PMID: 10392946 [PubMed-indexed for MEDLINE] No Abstract.

Heldman, A.W., et al., "Paclitaxel stent coating inhibits neointimal hyperplasia at 4 weeks in a porcine model of coronary restenosis, " *Circulation*, 103(18):2289-2295 (May 2001) PMID: 11342479 [PubMed-indexed for MEDLINE] Abstract.

Herdeg, C., et al., "Paclitaxel: a chemotherapeutic agent for prevention of restenosis? Experimental studies in vitro and in vivo," *Z Kardiol*, 89(5):390-397 (2000) PMID: 10900668 [PubMed-indexed for MEDLINE] Abstract.

Herdeg, C. et al., "Visualization and comparison of drug effects after local paclitaxel delivery with different catheter types," *Basic Res Cardiol*, 94(6):454-463 (Dec. 1999) PMID: 10651157 [PubMed-indexed for MEDLINE] Abstract.

Herdeg, C. et al., "Local paclitaxel delivery for the prevention of restenosis: biological effects and efficacy in vivo," *J Am Coll Cardiol*, 35(7):1969-1976 (Jun. 2000) PMID: 10841250 [PubMed-indexed for MEDLINE] Abstract.

Herdeg, C., et al., "Antiproliferative stent coatings: Taxol and related compounds," *Semin Interv Cardiol*, 3(3-4):197-199 (Sep.-Dec. 1998) PMID: 10406693 [PubMed-indexed for MEDLINE] Abstract.

Hicks, M.E., et al., "Multilevel infusion catheter for use with thrombolytic agents," *J Vasc Interv Radiol*, 2(1):73-75 (1991) PMID: 1799751 [PubMed-indexed for MEDLINE] Abstract.

Higgins, J.N., "Technical report: the use of ultrasound in positioning a catheter for thrombolysis of an occluded prosthetic femoropopliteal graft," *Clin Radiol*, 49(5):351-353 (1994) PMID: 8013204 [PubMed-indexed for MEDLINE] Abstract.

Himmelfarb, J., et al., "Hemodialysis vascular access: emerging concepts," *Curr Opin Nephrol Hypertens*, 5(6):485-491 (Nov. 1996) PMID: 8978994 [PubMed-indexed for MEDLINE] Abstract.

(56) References Cited

OTHER PUBLICATIONS

Hofma, S.H., et al., "Recent developments in coated stents," *Curr Interv Cardiol*, 3(1):28-36 (Feb. 2001) PMID: 11177717 [PubMed-indexed for MEDLINE] Abstract.
Honda, Y., et al., "Novel drug-delivery stent intravascular ultrasound observations from the first human experience with the QP2-eluting polymer stent system," *Circulation*, 104(4):380-383 (Jul. 2001) PMID: 11468196 [PubMed-indexed for MEDLINE] Abstract.
Horstmann, R., et al., "Value of preoperative angioplasty in surgery of the hemodialysis shunt," *Langenbeck Arch Chir Suppl Kongressbd*, 114:440-442 (1997) PMID: 9574176 [PubMed-indexed for MEDLINE] Abstract.
Hsu, S., et al., "Comparative In vitro evaluation of two different preparations of small diameter polyurethane vascular grafts," *Artif Organs*, 24(2):119-128 (Feb. 2000) PMID: 10718765 [PubMed-indexed for MEDLINE] Abstract.
Huebsch, J.B., et al., "Photoreactive analog of peptide FN-C/H-V from the carboxy-terminal heparin-binding domains of fibronectin supports endothelial cell adhesion and spreading on biomaterial surfaces," *J Biomed Mater Res*, 31(4):555-567 (Aug. 1996) PMID: 8836853 [PubMed-indexed for MEDLINE] Abstract.
Hurlbert, S.N., et al., "Long-term patency rates, complications and cost-effectiveness of polytetrafluoroethylene (PTFE) grafts for hemodialysis access: a prospective study that compares Impra versus Cortex grafts," *Cardiovasc Surg*, 6(6):652-656 (1998) PMID: 10395270 [PubMed-indexed for MEDLINE] Abstract.
Hye, R.J;, et al., "Is thrombolysis of occluded popliteal and tibial bypass grafts worthwhile?" *J Vasc Surg*, 20(4):588-596 (1994) PMID: 7933260 [PudMed-.indexed for MEDLINE] Abstract.
Ikeda, Y., et al., "Thrombolysis of peripheral graft occlusion in patients with hyperpension," *Int Surg*, 80(2):185-188 (1995) PMID: 8530241 [PubMed-indexed for MEDLINE] Abstract.
Ikeda, Y., et al., "Thrombolysis therapy in patients with femoropepliteal synthetic graft occlusions," *Am J Surg*, 171(2):251-254 (1996) PMID: 8619462 [PubMed-indexed for MEDLINE] Abstract.
Ikeda, Y., et al., "Evaluation of multiple vascular reconstructive procedures with synthetic graft occlusion," *J Cardiovasc Surg*, 35(4):315-319 (1994) PMID: 7929543 [PubMed-indexed for MEDLINE] Abstract.
Ikeda, Y., et al., "Relationship of runoff vessels to results following thrombolysis and revascularization for synthetic grafts occlusions," *Am Surg*, 61(6):481-485 (1995) PMID: 7762894 [PubMed-indexed for MEDLINE] Abstract.
Imbert, E., et al., "Different growth behaviour of human umbilical vein endothelial cells and an endothelial cell line seeded on various polymer surfaces," *Biomaterials*, 19(24):2285-2290 (Dec. 1998) PMID: 9884041 [PubMed-indexed for MEDLINE] Abstract.
Jahn, C., et al., "In situ fibrinolysis of acute arteriovenous shunt obstructions during hemodialysis," *Nephrologie*, 15(2):145-150 (1994) PMID: 8047201 [PubMed-indexed for MEDLINE] Abstract.
Jakubiec, B., et al., "Measurement of CD11/CD18 integrin expression on the polymorphonuclear cell surface after incubation with synthetic vascular prostheses," *ASAIO J*, 40(3):M616-8 (Sep. 1994) PMID: 8555588 [Pub-Med-indexed for MEDLINE] Abstract.
Janosik, J.E., et al., "Therapeutic alternatives for subacute peripheral arterial occlusion. Comparison by outcome, length of stay, and hospital charges," *Invest Radiol*, 26(11):921-925 (Nov. 1991) PMID: 1743914 [PubMed-indexed for MEDLINE] Abstract.
Jensen, N. et al., "In vitro attachment of endothelial cells to different graft materials," *Eur Surg Res*, 28(1):49-54 (1996) PMID: 8682144 [PubMed-indexed for MEDLINE] Abstract.
Johnson, J.N., et al., "Mechanical graft thrombectomy: a new technique for unblocking long-standing graft thrombosis," *Br J Surg*, 81(1):50 (1994) PMID: 8313119 [PubMed-indexed for MEDLINE] No Abstract.
Kang, S.S., et al., "Selective stimulation of endothelial cell proliferation with inhibition of smooth muscle cell proliferation by fibroblast growth factor-1 plus heparin delivered from fibrin glue suspensions," *Surgery*, 118(2):280-286 (Aug. 1995) PMID: 7638745 [PubMed-indexed for MEDLINE] Abstract.
Kanterman, R.Y., et al., "Dialysis access grafts: anatomic location of venous stenosis and results of angioplasty," *Radiology*, 195(1):135-139 (Apr. 1995) PMID: 7892454 [PubMed-indexed for MEDLINE] Abstract.
Katz, S.G., et al., "The percutaneous treatment of angioaccess graft complications," *Am J Surg*, 170(3):238-242 (Sep. 1995) PMID: 7661289 [PubMed-indexed for MEDLINE] Abstract.
Kaufman, S.L., et al., "Urokinase thrombolysis using multiple side hole multilumen infusion catheter," *Cardiovasc Intervent Radiol*, 14(6):334-337 (1991) PMID: 1756548 [PubMed-indexed for MEDLINE] Abstract.
Kaufman, S.L., et al., "A prosptective comparison of two expanded polytetrafluoroethylene grafts for linear forearm hemodialysis access: does the manufacturer matter?" *J Am Coll Surg*, 185(1):74-79 (1997) PMID: 9208965 [PubMed-indexed for MEDLINE] Abstract.
Kerns, S.R., "Rigors with thrombolysis,"*J Vasc Interv Radiol*, 5(5):787 (1995) PMID: 8000132 [PubMed-indexed for MEDLINE] No Abstract.
Kinney, T.B., et al., "Pulmonary embolism from pulse-spray pharmacomechanical thrombolysis of clotted hemodialysis grafts: urokinase versus heparinized saline," *J Vasc Interv Radiol*, 11(9):1143-1152 (2000) PMID: 11041470 [PubMed-indexed for MEDLINE] Abstract.
Kipshidze, N., et al., "Perspectives on antisense therapy for the prevention of restenosis," *Current Opin in Molecular Therapeutic*, 3(3):265-277 (2001) PMID: 11497351 [PubMed-indexed for MEDLINE] Abstract.
Kipshidze, N., et al., Paclitaxel-coated stent is there a light at the end of the tunnel?, *J Am Coll Cardiol*, 38(1);292-3 (Jul. 2001) No Abstract.
Kito, H., et al., "Biocompatible coatings for luminal and outer surfaces of small-caliber artificial grafts," *J Biomed Mater Res*, 30(3)321-330 (Mar. 1996) PMID: 8698695 [PubMed-indexed for MEDLINE] Abstract.
Kito, H., et al., "Differentiated biocompatible design of luminal and outer graft surfaces. Photocurable extracellular matrices, fabrication, and cellular response," *ASAIO J*, 39(3):M506-11 (Jul.-Sep. 1993) PMID: 8268588 [PubMed-indexed for MEDLINE] Abstract.
Kohler, T.R., Kirkman, T.R., "Dialysis access failure: A sheep model of rapid stenosis," *J Vasc Surg*, 30(4):744-751 (Oct. 1999) PMID: 10514214 [PubMed-indexed for MEDLINE] Abstract.
Koyama, M., et al., "Surface coverage of vascular grafts with cultured human endothelial cells from subcutaneous fat tissue obtained with a biopsy needle," *Thromb Haemost*, 76(4):610-614 (Oct. 1996) PMID: 8903004 [PubMed-indexed for MEDLINE] Abstract.
Kroning, R., et al., "Taxol can induce phosphorylation of BCL-2 in multiple myeloma cells and potentiate dexamethasone-induced apoptosis," *Leuk Res*, 22(3):275-286 (Mar. 1998) PMID: 9619919 [PubMed-indexed for MEDLINE] Abstract.
Kumpe, D.A., "Prospective randomized comparison of surgical versus endovascular management of thrombosed dialysis access grafts," *J. Vasc Surg*, 28(2):386-387 (Aug. 1998). No abstract available. PMID: 9719343 [PubMed-indexed for MEDLINE] No Abstract.
Kurotobi, K. et al., "Ion implantation into collagen-coated surfaces for the development of small diameter artificial grafts," *Colloids Surg B Biointerfaces*, 19(3):227-235 (Dec. 2000) PMID: 10967496 [PubMed-indexed for MEDLINE] Abstract.
Kuwano, H., et al., "Patterns of pannus growth of the expanded polytetrafluoroethylene vascular graft with special attention to the intimal hyperplasia formation," *Am Surg*, 52(12):663-666 (Dec. 1986) PMID: 3789545 [PubMed-indexed for MEDLINE] Abstract.
Labs, J.D., et al., "Experimental treatment of thrombotic vascular occlusion," *Lasers Surg Med*, 11(4):363-371 (1991) PMID: 1895868 [PubMed-indexed for MEDLINE] Abstract.
Lacroix, H., et al., "Local thrombolysis for occluded arterial grafts: is the yield worth the effort?" *J Cardiovasc Surg*, 35(3):187-181 (1994) PMID: 8040165 [PubMed-indexed for MEDLINE] Abstract.

(56) References Cited

OTHER PUBLICATIONS

La Muraglia, G.M., et al., "Angioscopic evaluation of unilateral aortic graft limb thrombectomy: is it helpful?" *J Vasc Surg*, 17(6):1069-1074 (1993) PMID: 8505785 [PubMed-indexed for MEDLINE] Abstract.

Lazzaro, C.R., et al., "Modified use of the arrow-trerotola percutaneous thrombolytic device for the treatment of thrombosed menodialysis access grafts," *J Vasc Interv Radiol*, 10(8):1025-1031 (1999) PMID: 10496703 [PubMed-indexed for MEDLINE] Abstract.

Lee, D.E., et al., "Direct graft puncture with use of a crossed catheter technique for thrombolysis of peripheral bypsis grafts," *J Vasc Interv Radiol*, 11(4):445-452 (2000) PMID: 10787202 [PubMed-indexed for MEDLINE] Abstract.

Leon, M.B., et.al., "Localized intracoronary gamma-radiation therapy to inhibit the recurrence of restenosis after stenting," *N Engl J Med*, 25;344(4):250-256 (2001) PMID: 11172151 [PubMed-indexed for MEDLINE] Abstract.

Liistro, F., et al., "Late acute thrombosis after paclitaxel eluting stent implantation," *Heart*, 86(3):262-264 (Sep. 2001) PMID: 11514475 [PubMed-indexed for MEDLINE] Abstract.

Lovering, A.M., et al. "A comparative study of the rifampicin binding and elution characteristics for collagen- and albumin-sealed vascular grafts," *Eur J Vasc Endovasc Surg*, 17(4):347-350 (Apr. 1999) PMID: 10204059 [PubMed-indexed for MEDLINE] Abstract.

Lumsden, A.B., et al., "Nonporous silicone polymer coating of expanded polytetrafluoroethylene grafts reduces graft neointimal hyperplasia in dog and baboon models," *J Vasc Surg*, 24(5):825-833 (Nov. 1996) 8918330 Abstract.

Lumsden, A.B., et al., "Prophylactic balloon angioplasty fails to prolong the patency of expanded polytetrafluoroethylene arteriovenous grafts: results of a prospective randomized study," *J Vasc Surg*, 26(3):382-390 (1997) PMID: 9308584 [PubMed-indexed for MEDLINE] Abstract.

Lundell, A., et al., "Reduction in vascular lesion formation by hirudin secreted from retrovirus-transduced confluent endothelial cells on vascular grafts in baboons," *Circulation*, 100(19):2018-2024 (Nov. 1999) PMID: 10556229 [PubMed-indexed for MEDLINE] Abstract.

Magnan, P.E., et al., "Intra-arterial thrombolysis using re-PA for the treatment of occluded infra-inguinal bypasses," *J Mal Vasc*, 19(2):119-125 (1994) PMID: 8077860 [PubMed-indexed for MEDLINE] Abstract.

Mahon, B.R. "Ultrasound guidance to gain access for the 'lyse and wait' technique," *J Vasc Interv Radiol*, 10(6):833 (1999) PMID: 10392957 [PubMed-indexed for MEDLINE] No Abstract.

Marston, W.A., et al., "Re: Comparison of the AngioJet rheolytic catheter to surgical thrombectomy for the treatment of thrombosed hemodialysis grafts," *J Vasc Interv Radiol*,11(8):1095-1096 (2000) PMID: 10997477 [PubMed-indexed for MEDLINE] No Abstract.

Marston, W.A., et al., "Prospective randomized comparison of surgical versus endovascular management of thrombosed dialysis access grafts," *J Vasc Surg*, 26(3):373-380 (1997) PMID: 9308583 [PubMed-indexed for MEDLINE] Abstract.

Martin, L.G., et al., "Prophylactic angioplasty reduces thrombosis in virgin ePTFE arteriovenous dialysis grafts with greater then 50% stenosis: subset analysis of a prospectively randomized study," *J Vasc Interv Radiol*, 10(4):389-396 (Apr. 1999). PMID: 10229464 [PubMed-indexed for MEDLINE] Abstract.

Martino, M.A., et al., "Erythropoietin therapy improves graft patency with No increased incidence of thrombosis or thrombophlebitis," *J Am Coll Surg*, 187(6);616-619 (1998) PMID: 9849735 [PubMed-indexed for MEDLINE] Abstract.

Marx, S.O., et al., "Bench to bedside: the development of rapamycin and its application to stent restenosis," *Circulation*, 104:852-855 (2001) PMID: 11514367 [PubMed-indexed for MEDLINE] No Abstract.

Maskova, J., et al., "Surgical interventions in dialysis fistulae," *Rozhl Chir*, 78(11):562-568 (1999) PMID: 10746071 [PubMed-indexed for MEDLINE] Abstract.

Mathias, K., "Local trombolysis for salvage of occluded bypass grafts," *Semin Thromb Hemost*, 17(1):14-20 (1991) PMID: 1828623 [PubMed-indexed for MEDLINE] No Abstract.

Mattsson, E.J., et al., "Increased blood flow induces regression of intimal hyperplasia," *Arterioscler Thromb Vasc Biol*, 17(10):2245-2249 (Oct. 1997) PMID: 9351396 [PubMed-indexed for MEDLINE] Abstract.

Mc Keever, L., et al., "Prolonged selective urokinase infusion in totally occluded coronary arteries and bypass grafts: two case reports," *Cathet Cardiovasc Diagn*, 15(4):247-251 (1988) PMID: 3265895 [PubMed-indexed for MEDLINE] Abstract.

Mc Namara, T.O., et al., "Thrombolysis of peripheral arterial and graft occlusions: improved results using high-dose urokinase," *AJR Am J Roentgenol*, 144(4):769-775 (1985) PMID: 3872036 [PubMed-indexed for MEDLINE] Abstract.

Mc Namara, T.O., et al., "Factors affecting initial and 6 month patency rates after intraarterial thrombolysis with high dose urokinase," *Am J Surg*, 152(6):709-712 (Dec. 1986). PMID: 3789300 [PubMed-indexed for MEDLINE] Abstract.

Mc Namara, T.O., et al., "Intra-arterial urokinase as the initial therapy for acutely ischemic lower limbs," *Circulation*, 83(2 Suppl)I106-19 (1991) PMID: 1991392 [PubMed-indexed for MEDLINE] Abstract.

Meguro, T, et al., "Effect of external stenting and systemic hypertension on intimal hyperplasia in rat vein grafin," *Neurosurgery*, 46(4):963-970 (Apr. 2000) PMID: 10764272 [PubMed-indexed for MEDLINE] Abstract.

Mehta, S., et al., "Gentamicin distribution from a collagen carrier," *J Orthop Res*, 14:749-754 (1996) PMID: 8893768 [PubMed-indexed for MEDLINE] Abstract.

Middlebrook, M.R., et al., "Thrombosed hemodialysis grafts: percutaneous mechanical balloon declotting versus thrombolysis," *Radiology*, 196(1):P73-77 (1995) PMID: 7784593 [PubMed-indexed for MEDLINE] Abstract.

Miller, H.J., et al., "Paclitaxel as the initial treatment of multiple myeloma: an Eastern Cooperative Oncology Group Study (E1A93)," *Am J Clin Oncol*, 21(6):553-556 (Dec. 1998) PMID: 9856654 [PubMed-indexed for MEDLINE] Abstract.

Miller, B.V., et al., "Management of infrainguinal occluded vein bypasses with a combined approach of thrombolysis and surveillance. A prospective study," *Arch Surg*, 127(8):986-989 (1992) PMID: 1386507 [PubMed-indexed for MEDLINE] Abstract.

Mironov, S.L., et al., "Cytoskeleton mediates inhibition of the fast Na+ current in respiratory brainstem neurons during hyposia," *Eur J Neurosci*, 11(5):1831-1834 (May 1999) PMID: 10215936 [PubMed-indexed for MEDLINE] Abstract.

Miwa, H., et al., "Improved patency of an elastomeric vascular graft by hybridization," *ASAIO J*, 38(3):M512-5 (Jul.-Sep. 1992) PMID: 1457913 [PubMed-indexed for MEDLINE] Abstract.

Molina, J.E., "Need for emergency treatment in subclavian vein effort thrombosis," *J Am Coll Surg*, 181(5):414-420 (1995) PMID: 7582208 [PubMed-indexed for MEDLINE] Abstract.

Moneta, G.L., et al. "Repair and follow-up of leg arteries with vein grafts," *West J Med*, 159(6):683 (1993) PMID: 8128680 [PubMed-indexed for MEDLINE] No Abstract.

Morag, B., et al., "Intra-arterial thrombolytic therapy: a combined approach with angioplasty and/or minor surgery," *Isr J Med Sci*, 29(11):707-713, (1993) PMID: 8270403 [PubMed-indexed for MEDLINE] Abstract.

Morris, C.S., et al., "Treatment of acute aortorenal bypass graft thrombosis by means of primary stent replacement and adjunctive thrombolysis," *J Vasc Interv Radiol*, 9(6):1281-1282 (1999) No Abstract.

Morse, M.A., et al., "A comparative study of the generation of dendritic cells from mobilized peripheral blood progenitor cells of patients undergoing high-dose chemotherapy," *J Hematother Stem Cell Res*, 8(6):577-584 (Dec. 1999) PMID: 10645764 [PubMed-indexed for MEDLINE] Abstract.

Moses, J.W., et al., "The U.S. multicenter, randomized, double-blind study of the sirolimus-eluting stent in coronary lesions: early (30-day) safety results," *Circulation*, Suppl II; v104:17, abstract (Oct. 2001).

(56) References Cited

OTHER PUBLICATIONS

Nackman, G.B., et al., "Thrombolysis of occluded infrainguinal vein grafts: predictors of outcome," *J Vasc Surg*, 25(6):1023-1031 (1998) PMID: 9201163 [PubMed-indexed for MEDLINE] Abstract.
Nakagawa, Y., et al., "Clinical trial of new polyurethane vascular grafts for hemodialysis: compared with expanded polytetrafluoroethylene grafts," *Artif Organs*, 19(12):1227-1232 (Dec. 1995) PMID: 8967879 [PubMed-indexed for MEDLINE] Abstract.
Nathan, A., et al., "Tissue engineered perivascular endothelial cell implants regulate vascular injury,"*Proc. Natl. Acad. Sci. USA*, 92:8130-8134 (Aug. 1995) PMID: 7667257 [Pub/Med-indexed for MEDLINE] Abstract.
Newman, K.D., et al., "Quantification of vascular graft seeding by use of computer-assisted image analysis and genetically modified endothelial cells," *J Vasc Surg*, 14(2):140-146 (Aug. 1991) PMID: 1861324 [PubMed-indexed for MEDLINE] Abstract.
NIH Consensus Statement, "Morbidity and mortality of dialysis," 11:1-33. (1993). (Generic) Ref Type: Conference proceeding PMID: 8004133 [PubMed-indexed for MEDLINE] Abstract.
Nomori, H., et al., "Mixing collagen with fibrin glue to strengthen the sealing effect for pulmonary air leakage," *Ann Thorac Surg*, 70(5):1666-1670 (Nov. 2000) PMID: 11093507 [PubMed-indexed for MEDLINE] Abstract.
Novoa, D., et al., "Treatment with urokinase for thrombotic complications of the bio-carbon prosthesis for hemodialysis," *Clin Nephrol*, 24(6):315 (1985) PMID: 4075601 [PubMed-indexed for MEDLINE] No Abstract.
Oberhoff, M., et al., "Local delivery of paclitaxel using the double-balloon perfusion catheter before stenting in the porcine coronary artery," *Catheter Cardiovasc Interv*, 53(4):562-568 (Aug. 2001) PMID: 11515014 [PubMed-indexed for MEDLINE] Abstract.
Okada, T., et al., "Localized release of perivascular heparin inhibits intimal proliferation after endothelial injury without systemic anticoagulation," *Neurosurgery*, 25:6, 892-898 (1989) PMID: 2601819 [PubMed-indexed for MEDLINE] Abstract.
Okahara, K., et al., "Healing of polytetrafluoroethylene vascular grafts analyzed by anti-smooth muscle myosin heavy chain isoforms," *Pathobiology*, 63(3):160-167 (1995) PMID: 8821632 [PubMed-indexed for MEDLINE] Abstract.
Okoshi, T., et al., "Penetrating micropores increase patency and achieve extensive endothelialization in small diameter polymer skin coated vascular grafts," *ASAIO J*, 42(5):M398-401 (Sep.-Oct. 1996) PMID: 8944915 [PubMed-indexed for MEDLINE] Abstract.
Olszewski, W., "Clinical efficacy of micronized purified flavonoid fraction (MPFF) in edema," *Angiology*, 51(1):25-29 (Jan. 2000) PMID: 10667640 [PubMed-indexed for MEDLINE] Abstract.
Oltrona, L., et al., "Efficacy of local inhibition of procoagulant activity associated with small-diameter prosthetic vascular grafts," *J Vasc Surg*, 24(4):624-631 (Oct. 1996) PMID: 8911411 [PubMed-indexid for MEDLINE] Abstract.
Ono, I., et al., "Effects of a collagen matrix containing prostaglandin E(1) on wound contraction," *J Dermatol Sci*, 25(2):106-115 (Feb. 2001) PMID: 11164707 [PubMed-indexed for MEDLINE] Abstract.
Ortensia, A., et al., "Use of urokinase in the occlusion of the vascular access routes in chronic hemodialysis, 7 year's' experience," *Minerva Urol Nefrol*, 42(1):51-53 (1990) PMID: 2389223 [PubMed-indexed for MEDLINE] Abstract.
Ouriel, K., et al., "Differential mechanisms of failure of autogenous and non-autogenous bypass conduits: an assessment following successful graft thrombolysis," *Cardiovasc Surg.*; 3(5):469-473 (Oct. 1995). PMID: 8574527 [PubMed-indexed for MEDLINE].
Parent, F.N., 3rd, et al., "Outcome of intraarterial urokinase for acute vascular occlusion," *J Cardiovasc Surg*, 32(5):680-689 (1991) PMID: 1939333 [PubMed-indexed for MEDLINE] Abstract.
Parent, F.N.,3[rd], et al., "Angioscopic assessment of fibrinolysis for impending in situ saphenous vein graft thrombosis," *Ann Vasc Surg*, 5(5):473-476 (1991) PMID: 1958464 [PubMed-indexed for MEDLINE] Abstract.
Parikh S., Nori D, "External beam radiation for patients with arteriovenous dialysis," *Vascular Brachytherapy*, Ed: Waksman R.,
Funtra Publishing, Armonk, 417-434 (1999) PMID: 11272354 [PubMed-indexed for MEDLINE] Abstract.
Park, S.J., et al., "The clinical effectiveness of paclitaxel-coated coronary stents for the reduction of restenosis in the ASPECT trial," *Circulation*, Suppl II; v104:17, abstract 21299 (Oct. 2001) Abstract.
Parsson, H., et al., "The adhesion of labelled neutrophils on synthetic vascular grafts. An experimental porcine study," *Eur J Vasc Surg*, 7(3)257-262 (May 1993) PMID: 8513904 [PubMed-indexed for MEDLINE] Abstract.
Patel, R.I., et al., "Patency of Wallstents placed across the venous anastomosis of hemodialysis grafts after percutaneous recanalization," *Radiology*, 209(2):365-370 (Nov. 1998) PMID: 9807560 [PubMed-indexed for MEDLINE] Abstract.
Pattynama, P.M., et al., "Revascularization of occluded haemodialysis fistulae with the Hydrolyser thrombectomy catheter: description of the technique and report of six cases," *Nephrol Dial Transplant*, 10(7):1274-1727 (1995) PMID: 7478128 [PubMed-indexed for MEDLINE] Abstract.
Perler, B.A., et al., "Transgraft hemorrhage: a serious complication of low-dose thrombolytic therapy," *J Vasc Surg*, 3(6):936-938 (1986) PMID: 2940380 [PubMed-indexed for MEDLINE] Abstract.
Petronis, J.D., et al., "Ventilation-perfusion scintigraphic evaluation of pulmonary clot burden after percutaneous thrombolysis of clotted hemodialysis access grafts," *Am J Kidney Dis*, 34(2):207-211 (1999) PMID: 10430963 [PubMed-indexed for MEDLINE] Abstract.
Polak, J.F., et al., "Comparative efficacy of pulse-spray thrombolysis and angioplasty versus surgical salvage procedures for treatment of recurrent occlusion of PTFE dialysis access grafts," *Cardiovasc Intervent Radiol*, 21(4):314-318 (1998) PMID: 9688799 [PubMed-indexed for MEDLINE] Abstract.
Porter, K.E., "The development of an in vitro flow model of human saphenous vein graft intimal hyperplasia," *Cardiovasc Res*, 31(4):607-614 (Apr. 1996) PMID: 8689653 [PubMed-indexed for MEDLINE] Abstract.
Poulain, F., et al., "Local thrombolysis and thromboaspiration in the treatment of acutely thrombosed arteriovenous hemodialysis fistulas," *Cardiovasc Intervent Radiol*, 14(2):98-101 (1991) PMID: 1830241 [PubMed-indexed for MEDLINE] Abstract.
Pratesi, C. et al.; "Thrombolysis of acute ischemia of the extremities," *Vasa Suppl*, 27:303-307 (1989) PMID: 2623520 [PubMed-indexed for MEDLINE] No Abstract.
Price, C., et al., "Thrombolytic therapy in acute arterial thrombosis," *Am J Surg*, 156(6):488-491(1988) PMID: 3202261 [PubMed-indexed for MEDLINE] Abstract.
Pronk, A., et al., "Mesothelial cell adherence to vascular prostheses and their subsequent growth in vitro," *Cell Transplant*, 3(1):41-48 (Jan.-Feb. 1994) PMID: 8162292 [PubMed-indexed for MEDLINE]. Abstract.
Puckett, J.W., et al., "Midgraft curettage as a routine adjunct to salvage operations for thrombosed polytetrafluoroethylene hemodialysis access grafts," *Am J Surg*, 156(2):139-143 (1988) PMID: 3400814 [PubMed-indexed for MEDLINE] Abstract.
Rekbter, M.D. et al., "Cell proliferation in human arteriovenous fistulas used for hemodialysis," *Arterioscler Thromb*, 13:609-617 (1993).
Remy, M., et al., "In vitro and in situ intercellular adhesion molecule-1 (ICAM-1) expression by endothelial cells lining a polyester fabric," *Biomaterials*, 20(3):241-251 (Feb. 1999) PMID: 10030601 [PubMed-indexed for MEDLINE].Abstract.
Ricotta, J. "Intra-arterial thrombolysis. A surgical view," *Circulation*, 83(2 Suppl):1120-1121 (1991) PMID: 1991394 [PubMed-indexed for MEDLINE] No Abstract.
Rivitz, S.M., et al., "Percutaneous aspiration thrombectomy of an acutely occluded aortorenal bypass graft," *AJR Am J Roentgenol*, 164(2):455-458 (1995) PMID: 7839988 [PubMed-indexed for MEDLINE] No Abstract.
Roberts, A.C., et al., "Pulse-spray phannacomechanical thrombolysis for treatment of thrombosed dialysis access grafts," *Am J Surg*, 166(2):221-225 (1993) PMID: 8352419 [PubMed-indexed for MEDLINE] Abstract.

(56) References Cited

OTHER PUBLICATIONS

Robinson, K.A., et al., "Seeding of vascular grafts with an immortalized human dermal microvascular endothelial cell line," *Angiology*, 46(2):107-113 (Feb. 1995) PMID: 7702194 [PubMed-indexed for MEDLINE] Abstract.

Rocek, M., et al., "Mechanical thrombolysis of thrombosed hemodialysis native fistulas with use of the Arrow-Trerotola percutaneous thrombolytic device: our preliminary experience," *J Vasc Interv Radiol*, 11(9):1153-1158 (2000) PMID: 110414711 [PubMed-indexed for MEDLINE] Abstract.

Rousseau, H., et al., "Percutaneous recanalization of acutely thrombosed vessels by hydrodynamic thrombectomy (Hydrolyser)," *Eur Radiol*, 7(6):935-941 (1997) PMID: 9228112 [PubMed-indexed for MEDLINE] Abstract.

Roy-Chaudbury P., et al., "Venous neointimal hyperplasia in polytetrafluoroethylene dialysis grafts," *Kidney International*, 59:2325-2334 (2001) Abstract.

Rubens, F.D., et al., "Platelet accumulation on fibrin-coated polyethylene: role of platelet activation and factor XIII," *Thromb Haemost*, 73(5):850-856 (May 1995) PMID: 7482415 [PubMed-indexed for MEDLINE] Abstract.

Rubens, F.D., et al., "The effect of antidvombin III-independent thrombin inhibitors and heparin on fibrin accretion onto fibrin-coated polyethylene," *Thromb Haemost*, 96(2):130-134 (Feb. 1993) PMID: 8456425 [PubMed-indexed for MEDLINE] Abstract.

Saeed M., et al., "Stenoses in dialysis fistulas: treatment with percutaneous angioplasty," *Radiology*, 164(3):693-697 (Sep. 1987) PMID: 2956626 [PubMed-indexed for MEDLINE] Abstract.

San Roman, J., et al., "Experimental study of the antithrombogenic behavior of Dacron vascular grafts coated with hydrophilic acrylic copolymers bearing salicylic acid residues," *J Biomed Matter Res*, 32(1):19-27 (Sep. 1996) PMID: 8864869 [Pub-Med-indexed for MEDLINE] Abstract.

San Roman, J., et al., "Application of new coatings for vascular grafts based on polyacrylic systems with antiaggregating activity," *Biomaterials*, 15(10):759-765 (Aug. 1994) PMID: 7986939 [PubMed-indexed for MEDLINE] Abstract.

Sandhu, J.S., et al., "Use of a stone basket to treat lysis-resistant clot after pulse-spray thrombolysis of an occluded hemodialysis graft," *AJR Am J Roentgenol*, 163(4):957-959 (1994) PMID: 8092042 [PubMed-indexed for MEDLINE] No Abstract.

Sands, J.J., et al., "Pharmacomechanical thrombolysis with urokinase for treatment of thrombosed hemodialysis access grafts. A comparison," *ASAIO J*, 40(3):M886-8 (1994) PMID: 8555639 [PubMed-indexed for MEDLINE] Abstract.

Sank, A., et al., "New evidence and new hope concerning endothelial seeding of vascular grafts," *Am J Surg*, 164(3):199-204 (Sep. 1992) PMID: 1415914 [PubMed-indexed for MEDLINE] Abstract.

Sano, C., et al., "Thrombolytic therapy before reconstructive vascular procedure for acute or subacute graft occlusions," *Int Surg*, 78(1):50-53 (1993) PMID: 8473085 [PubMed-indexed for MEDLINE] Abstract.

Sapienza, P., et al., "High-porosity and normal-porosity prostheses. Differences in growth factor release," *Minerva Cardioangiol*, 46(5):141-148 (May 1998) PMID: 9842196 [PubMed-indexed for MEDLINE] Abstract.

Sapienza, P., et al., "Release of PDGF-BB and bFGF by human endothelial cells seeded on expanded polytetrafluoroethylene vascular grafts," *J Surg Res*, 75(1):24-29 (Feb. 1998) PMID: 9842196 [PubMed-indexed for MEDLINE] Abstract.

Sapoval M., et al., "Cragg covered stents in hemodialysis access: initial and mid-term results," *J Vasc Interven Radiol*, 7:335-342 (1996) PMID: 8761808 [PubMed-indexed for MEDLINE] Abstract.

Schilling, J.J., et al., "The role of thrombolysis in hemodialysis," *Am J Kidney Dis*, 10(2):92-97 (1987) PMID: 3605094 [PubMed-indexed for MEDLINE] Abstract.

Schilling, J.D., et al., "Catheter-directed urokinase thrombolysis: and adjunct to PTA/surgery for management of lower extremity throboembolic disease," *Angiology*, 45(10):851-860 (1994) PMID: 7943936 [PubMed-indexed for MEDLINE] Abstract.

Schneider, A., et al., "Naturally produced extracellular matrix is an excellent substrate for canine endothelial cell proliferation and resistance to shear stress on PTFE vascular grafts," *Thromb Haemost*, 78(5):1392-1398 (Nov. 1997) PMID: 9408025 [PubMed-indexed for MEDLINE] Abstract.

Schneider, A., et al., "An improved method of endothelial seeding on small caliber prosthetic vascular grafts coated with natural extracellular matrix," *Clin Mater*, 13(1-4):51-55 (1993) PMID: 10146243 [PubMed-indexed for MEDLINE] Abstract.

Schneider, A., et al., "An improved method for endothelial cell seeding on polytetrafluoroethylene small caliber vascular grafts," *J Vasc Surg*, 15(4):649-656 (Apr. 1992) PMID: 1560554 [PubMed-indexed for MEDLINE] Abstract.

Schon, D. et al., "Salvage of occluded autologous arteriovenous fistulae," *Am J Kidney Dis*, 36(4):804-810 (2000) PMID: 11007684 [PubMed-indexed for MEDLINE] Abstract.

Schuman, E.S., et al., "Reinforced versus nonreinforced polytetrafluoroethylene grafts for hemodialysis access;" *Am J Surg*, 173(5):407-410 (May 1997) PMID: 9168077 [PubMed-indexed for MEDLINE] Abstract.

Schuman, E., et al., "Thrombolysis versus thrombectomy for occluded hemodialysis grafts,"*Am J Surg*, 167(5):473-476 (1994) PMID: 8185029 [PubMed-indexed for MEDLINE] Abstract.

Schwab, S.J., "Hemodialysis vascular access: an ounce of prevention" *Kidney Int.*, 1997 Declaration;52(6):1704-5. No abstract available. PMID: 9407521 [PubMed-indexed for MEDLINE] No Abstract.

Schwartz, C.I. et al., "Thrombosed dialysis grafts: comparison of treatment with transluminal angioplasty and surgical revision," *Radiology*, 194(2):337-374 PMID: 7824708 [PubMed-indexed for MEDLINE] Abstract.

Seabrook, G.R., et al., "Percutaneous intraarterial thrombolysis in the treatment of thrombosis of lower extremity arterial reconstructions," *J Vasc Surg*, 13(5):646-651 (1991) PMID: 1827505 [PubMed-indexed for MEDLINE] Abstract.

Seifert, S.A., et al., "Accidental, intravenous infusion of a peanut oil-based medication,"*J Toxicol Clin Toxicol*, 36(7):733-736 (1998) PMID: 9865244 [PubMed-indexed for MEDLINE] Abstract.

Sekine, T., et al., "A new type of surgical adhesive made from porcine collagen and polyglutamic acid," *J Biomed Mater Res*, 54(2):305-310 (Feb. 2001) 11093191 Abstract.

Self, S.B., et al., "Rotational atherectomy for treatment of occluded prosthetic grafts" *J Surg Res*, 56(2):134-140 (1994) PMID: 8121169 [PubMed-indexed for MEDLINE] Abstract.

Selye H, Berezy I., "The present status of calciphylaxis and calcergy," *Clin Orthop*, 69:28-54 (1970) c No Abstract.

Semb, K.A., et al., "Capillary protein leak syndrome appears to explain fluid retention in cancer patients who receive docetaxel treatment," *J Clin Oncol*, 16(10):3426-3432 (Oct. 1998) PMID: 9779722 [PubMed-indexed for MEDLINE] Abstract.

Semba, C.P. et al., "Iliofemoral deep venous thrombosis: aggressive therapy with catheter-directed thrombolysis," *Radiology*, 19(2);487-494 (1994) PMID: 8153327 [PubMed-indexed for MEDLINE] Abstract.

Sharafuddin, M.J., et al., "Percutaneous balloon-assisted aspiration thrombectomy o fclotted hemodialysis access grafts," *J Vasc Interv Radiol*, 7(2):177-183 (1996) PMID: 9007795 [PubMed-indexed for MEDLINE] Abstract.

Sharafuddin, M.J., et al., "Current status of percutaneous mechanical thrombectomy. Part III. Present and future applications," *J Vasc Interv Radiol*, 9(2):209-224 (1998) PMID: 9540903 [PubMed-indexed for MEDLINE] No Abstract.

Shayani, V., "Optimization of recombinant t-PA secretion from seeded vascular grafts," *J Surg Res*, 57(4):495-504 (Oct. 1994) PMID: 7934027 [PubMed-indexed for MEDLINE] Abstract.

Sheppard, R., et al., "Intracoronary radiotherapy for restenosis," *N Engl J Med*, 344(4):295-297 (2001) PMID: 11172158 [PubMed-indexed for MEDLINE] No Abstract.

Shi, C., et al., "Plasminogen is not required for neointima formation in a mouse model of vein graft stenosis," *Circ Res*, 84(8):883-890 (Apr. 1999) PMID: 10222334 [PubMed-indexed for MEDLINE] Abstract.

(56) References Cited

OTHER PUBLICATIONS

Shi, Q., et al., "Proof of fallout endothelialization of impervious Dacron grafts in the aorta and inferior vena cava of the dog," *J Vasc Surg*, 20(4):546-557 (Oct. 1994) PMID: 7933256 [PubMed-indexed for MEDLINE] Abstract.
Shortell, C.K., et al., "Thrombolysis in acute peripheral arterial occlusion: predictors of immediate success," *Ann Vasc Surg*, 8(1):59-65 (1994) PMID: 8193001 [PubMed-indexed for MEDLINE] Abstract.
Sierra, D., et al., "Surgical-adhesives and sealants," *Current Tech. and Appl*, Technomic Publ Co Inc, Lancaster-Basel, p. 247 (1996).
Signore, et al., "Complete inhibition of intimal hyperplasia by perivascular delivery of paclitaxel in balloon-injured rat carotid arteries" *J Vasc Interv Radiol*, 2001; 12:79-88 PMID: 11200358 [PubMed-indexed for MEDLINE] Abstract.
Silva, J.A., et al., "Rheolytic thrombectomy in the treatment of acute limb-threatening ischemia: immediate results and six-month follow-up of the multicenter AngioJet registry. Possis Peripheral AngioJet Study AngioJet Investigators," *Cathet Cardiovasc Diagn*, 45(4):394-395 (1998) Abstract.
Sipehia, R., et al., "Transplantation of human endothelial cell monolayer on artificial vascular prosthesis: the effect of growth-support surface chemistry, cell seeding density, ECM protein coating, and growth factors," *Artif Cells Blood Substit Immobil Biotechnol*, 24(1):51-63 (Jan. 1996) PMID: 8714719 [PubMed-indexed for MEDLINE] Abstract.
Skobel, E., et al., "Relation between enzyme release and irreversible cell injury of the heart under the influence of cytoskeleton modulating agents," *Biochim Biophys Acta*, 1362(2-3):128-134 (Dec. 1997) PMID: 9540843 [PubMed-indexed for MEDLINE] Abstract.
Sladen, J.G., et al., "Thrombolysis for occluded vein bypass grafts through surgical access," *J Vasc Surg*, 18(6):1071-1072 (1993) PMID: 8264039 [PubMed-indexed for MEDLINE] Abstract.
Smith, D.C., et al., "Guide wire traversal test: retrospective study of results with fibrinolytic therapy," *J Vasc Interv Radiol*, 2(3):339-342 (1991) PMID: 1799778 [PubMed-indexed for MEDLINE] Abstract.
Sofocleous, C.T., et al., "Retrospective comparison of the Amplatz thrombectomy device with modified pulse-spray pharmacomechanical thrombolysis in the treatment of thrombosed hemodialysis access grafts," *Radiology*, 213(2):561-567 (1999) PMID: 10551242 [PubMed-indexed for MEDLINE] Abstract.
Solimando, D.A., "Paclitaxel package insert," *Cancer Invest*, 15(5):503 (1997) PMID: 9340126 [PubMed-indexed for MEDLINE] Abstract.
Sollott, S.J., "Taxol inhibits neointimal smooth muscle cell accumulation after angioplasty in the rat," *J Clin Invest*, 95(4):1869-1876 (Apr. 1995) PMID: 7706494 [PubMed-indexed for MEDLINE] Abstract.
Song, J. et al., "Effects of collagen gel configuration on behavior of vascular smooth muscle cells in vitro: association with vascular morphogenesis," *In Vitro Cell Dev Biol Anim*, 36(9):600-610 (Oct. 2000) PMID: 11212145 [PubMed-indexed for MEDLINE] Abstract.
Sousa, J.E., et al., "Lack of neointimal proliferation after implantation of sirolimus-coated stents in human coronary arteries: a quantitative coronary angiography and three-dimensional intravascular ultrasound study," *Circulation*, 103(2):192-195 (2001) PMID: 11208675 [PubMed-indexed for MEDLINE] Abstract.
Sousa, J., et al., "Sustained suppression of neointimal proliferation by sirolimus-eluting stouts," *Circulation*, 104:2007 (2001) PMID: 11673337 [PubMed-indexed for MEDLINE] Abstract.
Sousa, J.E., et al., "The RAVEL study: a randomized study with the sirolimus coated BX velocity balloon-expandable stent in the treatment of patients with de novo native coronary artery lesions," *Circulation*, Oct Suppl II:v1014:17, Abstract 2198 (2001).
Spence, L.D., et al., "Thrombolysis of infrapopliteal bypass grafts: efficacy and underlying angiographic pathology," *AJR Am J Roentgenol*, 169(3):717-721 (1997) PMID: 9275885 [PubMed-indexed for MEDLINE] Abstract.
Sreedhara, R., et al., "Anti-platelet therapy in graft thrombosis: results of a prospective, randomized, double-blind study," *Kidney Int*, 45(5):1477-1483 (1994) PMID: 8072261 [PubMed-indexed for MEDLINE] Abstract.
Sriram, V., et al., "Cell cycle in vasculoproliferative diseases-potential interventions and routes of delivery," *Circulation*, 1013:2414-2419 (2001) PMID: 11352893 [PubMed-indexed for MEDLINE] Abstract.
Standage, B.A., et al., "Single limb patency of polytetrafluoroethylene dialysis loop grafts maintained by traumatic fistulization," *Ann Vasc Surg*, 12(4):364-369 (Jul. 1998) PMID: 9676934 [PubMed-indexed for MEDLINE] Abstract.
Stanley J.C., et al., "Vascular surgery in the United States: workforce issues. Report of the Society for Vascular Surgery and the International Society for Cardiovascular Surgery, North American Chapter, Committee on Workforce Issues," *J Vasc Surg*, 23:172-81 (1996) PMID: 8558735 [PubMed-indexed for MEDLINE] Abstract.
Strauss, E.B., et al. "A rapid low-cost uncrossed sheath method for clearing thrombosed hemodialysis grafts," *AJR Am J Roentgenol*, 177(2):317-318 (2001) PMID: 11461852 [PubMed-indexed for MEDLINE] No Abstract.
Stroughton, J., et al., "Plasminogen acceleration of urokinase thrombolysis," *J Vasc Surg*, 19(2):298-3030 (1994) PMID: 8114191 [PubMed-indexed for MEDLINE] Abstract.
Stryga, W., "Methods and results of treating late thrombosis of vascular grafts caused by fibromuscular lesions of vascular anastomosis," *Pol Tyg Lek*, 49(16-17):366-368 (1994) PMID: 7708554 [PubMed-indexed for MEDLINE] Abstract.
Sugawara, Y., et al., "Adenovirus-mediated transfer of tissue-type plasminogen activator gene to human endothelial cells," *Surgery*, 122(1):91-100 (Jul. 1997) PMID: 9225920 [PubMed-indexed for MEDLINE] Abstract.
Suggs, W.D., et al., "Vein cuff interposition prevents juxta-anastomotic neointimal hyperplasia," *Ann Surg*, 207(6):717-723 (Jun. 1988) PMID: 3389940 [PubMed-indexed for MEDLINE] Abstract.
Suh, H., et al., "Regulation of smooth muscle cell proliferation using paclitaxel-loaded poly(ethylene oxide)-poly(lactide/glycolide) nanospheres," *J Biomed Mater Res*, 42(2):331-338 (Nov. 1998).
Sullivan, K.L., et al., "Efficacy of thrombolysis in infrainguinal bypass grafts," *Circulation*, 83(2 Suppl):I99-I105 (1991) PMID: 1991406 [PubMed-indexed for MEDLINE] Abstract.
Sullivan, K.L., et al., "Acceleration of thrombolysis with a high-dose transduombus bolus technique," *Radiology*, 173(3):805-8011 (1989) PMID: 2813789 [PubMed-indexed for MEDLINE] Abstract.
Sullivan, K.L., et al., "Hemodynamic screening and early percutaneous intervention reduce hemodialysis access thrombosis and increase graft longevity," *J Vasc Interv Radiol*, 8(2):163-170 (1997) PMID: 9083978 [PubMed-indexed for MEDLINE] No Abstract.
Summers, S., "Urokinase therapy for thrombosed hemodialysis access grafts," *Surg Gynecol Obstet*, 176(6):534-538 (1993) PMID: 8322124 [PubMed-indexed for MEDLINE] Abstract.
Suzuki, T., et al., "Stent-based delivery of sirolimus reduces neointimal formation in a porcine coronary model," *Circulation*, 104(1):1188-1193 (Sep. 4, 2001) PMID: 11535578 [PubMed-indexed for MEDLINE] Abstract.
Swan, T.L., et al.; "Pulmonary embolism following hemodialysis access thrombolysis/thrombectomy," *J Vasc Interv Radiol*, 6(5):683-683 ) PMID: 8541667 [PubMed-indexed for MEDLINE] Abstract.
Swedberg, S.H., et al., "Intimal fibromuscular hyperplasia at the venous anastomosis of PTFE grafts in hemodialysis patients. Clinical, immunocytochemical, light and electron microscopic assessment," *Circulation*, 80(6):1726-1736 (Dec. 1989) PMID: 2688974 [PubMed-indexed for MEDLINE Abstract.
Szymski, G.X., et al., "Manual thromboaspiration and dilation of thrombosed dialysis access grafts: Mid-term results of a symple concept," *J Vasc Interv Radiol*, 9(3):517-519 (1998) No Abstract.
Tabata, Y., et al., "Controlled release of vascular endothelial growth factor by use of collagen hydrogels," *J Biomater Sci Polym Ed*, 11(9):915-930 (2000) PMID: 11211086 [PubMed-indexed for MEDLINE] Abstract.
Tachibana, K., et al., "Albumin microbubble echo-contrast material as an enhancer for ultrasound accelerated thrombolysis," *Circulation*, 92(5):1148-1150 (1995) PMID: 7648659 [PubMed-indexed for MEDLINE] Abstract.

(56) References Cited

OTHER PUBLICATIONS

Tadavarthy, S.M., et al., "Mechanical thrombectomy with the Amplatz device: human experience," *J Vasc Interv Radiol*, 5(5):715-724 (1994) PMID: 8000120 [PubMed-indexed for MEDLINE] Abstract.
Tautenhabn, J. et al., "Arteriovenous fistulas for hemodialysis—patency rates and complications—a retrospective study," *Zentralbl Chir*, 119(7):506-510 (1994) PMID: 7941799 [PubMed-indexed for MEDLINE] Abstract.
Taylor, M.A., et al., "Intracerebral hemorrhage complicating urokinase infusion into an occluded aortocoronary bypass graft," *Cathet Cardiovasc Diagn*, 31(3):306-210 (1994) PMID: 8025938 [PubMed-indexed for MEDLINE] Abstract.
Teebken, O.E., et al., "A new concept for substitutes in vascular surgery," *Langenbecks Arch Chir Suppl Kongressbd*, 115:1256-1259 (1998) PMID: 9931852 [PubMed-indexed for MEDLINE] Abstract.
Teirstein, P.S., et al., "New frontiers in interventional cardiology: intravascular radiation to prevent restenosis," *Circulation*,104(21):2620-2626 (Nov. 2001) PMID: 11714660 [PubMed-indexed for MEDLINE] No Abstract.
Terada, S., et al., "Experimental study of ectopic-free tissue transfer of rabbit epigastric flap using small-caliber vascular grafts," *J Biomed Mater Res*, 45(1):28-35 (Apr. 1999) PMID: 10397954 [PubMed-indexed for MEDLINE] Abstract.
Terada, S., et al., "Anti-thrombogenic effects of 2-hydroxyethylmethacrylate-styrene block copolymer and argatroban in synthetic small-caliber vascular grafts in a rabbit inferior vena cava model," *J Reconstr Micrasurg*, 13(1):9-16 (Jan. 1997) PMID: 9120844 [PubMed-indexed for MEDLINE] Abstract.
Tordoir, J.H., et al., "Early experience with stretch polytetrafluoroetbylene grafts for haemodialysis access surgery: results of a prospective randomised study," *Eur J Vasc Endovasc Surg*, 9(3):305-309 (Apr. 1995) PMID: 7620956 [PubMed-indexed for MEDLINE] Abstract.
Trerotola, S.O., et al., "Treatment of thrombosed hemodialysis access grafts: Arrow-Trerotola percutaneous thrombolytic device versus pulse-spray thrombolyssis. Arro-Trerotola Percutaneous Thrombolytic Device Clinical Trial," *Radiology*, 206(2):403-414 (1998) PMID: 9457193 [PubMed-indexed for MEDLINE] Abstract.
Trerotola, S.O., et al., "Thrombosed dialysis access grafts: percutaneous mechanical declotting without urokinase," *Radiology*, 191(3):721-726 (19940 PMID: 8184052 [PubMed-indexed for MEDLINE] Abstract.
Trerotola, S.O., et al., "Pulmonary emboli from pulse-spray and mechanical thrombolysis: evaluation with an animal dialysis-graft model," *Radiology*, 200(1):169-176 (1996) Abstract.
Tseng, D.Y., et al., "Effects of amide and amine plasma-treated ePTFE vascular grafts on endothelial cell lining in an artificial circulatory system," *J Biomed Mater Res*, 42(2):188-198 (Nov. 1998) PMID: 9773815 [PubMed-indexed for MEDLINE] Abstract.
Tsuchida, H., et al., "Healing mechanisms of high-porosity PTFE grafts: significance of transmural structure," *J Surg Res*, 71(2):187-195 (Aug. 1997) Abstract.
Turmel-Rodrigues, L.A., "Hemodialysis graft declotting with the 'lyse and wait' technique: a new name for an old recipe," *J. Vasc Interv Radiol*, 10(1):96-98, (1999) PMID: 10872497 [PubMed-indexed for MEDLINE] No Abstract.
Turmel-Rodriguez L., et al., "Insufficient dialysis shunts: improved long-term patency rates with close hemodynamic monitoring, repeated percutaneous balloon angioplasty, and stent placement," *Radiology*, 187(1):273-278 (1993) PMID: 8451428 [PubMed-indexed for MEDLINE] Abstract.
Turmel-Rodrigues L., et al., "Manual catheter-directed aspiration and other thrombectomy techniques for declotting native fistulas for hemodialysis," *J Vasc Interv Radiol*, 12:1365-1371 (2001) PMID: 11742008 [PubMed-indexed for MEDLINE] Abstract.
Turmel-Rodrigues, L., et al., "Prospective randomized comparison of surgical versus endovascular management of thrombosed dialysis access grafts," *J Vasc Surg*, 28(2):384-386 (1998) PMID: 9719342 [PubMed-indexed for MEDLINE] No Abstract.

Twardowski, Z.J., "Urokinase and dialysis therapy," *Kidney Int*, 57(1):345 (2000) PMID: 10712113 [PubMed-indexed for MEDLINE] No Abstract.
Twardowski, Z.J., "High dose intradialytic urokinase to restore the patency of permanent central vein hemodialysis catheters," *Am J Kidney Dis*, 31(5):841-847 (1998) PMID: 9590195 [PubMed-indexed for MEDLINE] Abstract.
Uflacker, R., et al., "Treatment of thrombosed dialysis access grafts: randomized trial of surgical thrombectomy versus mechanical thrombectomy with the Amplatz device," *J Vasc Interv Radiol*, 7(2):185-192 (1996) PMID: 9007796 [PubMed-indexed for MEDLINE] Abstract.
Valji, K., et al., "Transcatheter treatment of thrombosed hemodialysis access grafts," *AJR Am J Roentgenol*, 164(4):823-829 (1995) PMID: 7726032 [PubMed-indexed for MEDLINE] Abstract.
Valji, K., et al., "Pulse-spray pharmacomechanical thrombolysis of thrombosed hemodialysis access grafts: long-term experience and comparison of original and current techniques," *AJR Am J Roentgenol*, 164(6):1495-1500 (1995) PMID: 7754901 [PubMed-indexed for MEDLINE] Abstract.
Valji, K., et al., "Pharmacomechanical thrombolysis and angiolplasty in the management of clotted hemodialysis grafts: early and late clinical results," *Radiology*, 178(1):243-247 (1991) PMID: 1824582 [PubMed-indexed for MEDLINE] Abstract.
Valji, K., et al., "Pulsed-spray thrombolysis of arterial and bypass graft occlusions," *AJR Am J Roentgenol*, 156(3):617-621 (1991) PMID: 1825256 [PubMed-indexed for MEDLINE] Abstract.
Van Damme, H., et al., "Thrombolysis of occluded infrainguinal bypass grafts," 97(4):177-183 (1997) PMID: 9381900 [PubMed-indexed for MEDLINE] Abstract.
Vassilomanolakis, M. et al., "Long lasting, grade IV, orthostatic hypotension after a single cycle combination chemtherapy with paclitaxel and cisplatin," *Eur J Cancer*, 34(8):1295 (Jul. 1998) PMID: 9849495 [PubMed-indexed for MEDLINE] No Abstract.
Verhagen, H.J., et al., "In vivo experiments with mesothelial cell seeded ePTFE vascular grafts," *Eur J Vasc Endovasc Surg*, 15(6):489-496 (Jun. 1998) PMID: 9659883 [PubMed-indexed for MEDLINE] Abstract.
Vesely, T.M., et al., "Thrombolysis versus surgical thrombectomy for the treatment of dialysis graft thrombosis: pilot study comparing costs," *J. Vasc Interv Radiol*, Jul.-Aug. 1996;7(4):507-512. PMID: 8855526 [PubMed-indexed for MEDLINE] Abstract.
Vesely, T.M., et al., "Use of a purse string suture of close a percutaneous access site after hemodialysis graft intervention," *J Vasc Interv Radiol*, 9(3):447-450 (1998) PMID: 9618104 [PubMed-indexed for MEDLINE] No Abstract.
Vesely, T.M., et al., "Comparison of the angiojet rheolytic catheter to surgical thrombectomy for the treatment of thrombosed hemodialysis grafts. Peripheral AngioJet Clinical Trial," *J Vasc Interv Radiol*, 10(9):1195-1205 (1999) PMID: 10527197 [PubMed-indexed for MEDLINE] Abstract.
Viron, B., et al., "Urokinase in patients dialyzed with Hemasite," *Clin Nephrol*, 25(6):314) PMID: 3731546 [PubMed-indexed for MEDLINE] No Abstract.
Vogel, P.M., et al., "Thrombosed hemodialysis grafts: lyse and wait with tissue plasminogen activator or urokinase compared to mechanical thrombolysis with the Arrow-Trerotola Percutaneous Thrombolytic Device," *J Vasc Interv Radiol*, 12(10):1157-1165 (2001) PMID: 11585881 [PubMed-indexed for MEDLINE] Abstract.
Vorwerk, D., et al., "Hydrodynamic thrombectomy of hemodialysis fistulas: first clinical results," *J Vasc Interv Radiol*, 5(6):813-821 (1994) PMID: 7873857 [PubMed-indexed for MEDLINE] Abstract.
Vorwerk, D., et al., "Percutaneous treatment possibilities in thrombotic occlusion of Brescia-Cimino dialysis shunts," *Rofo Fortschr Geb Rontgenstr Neuen Bildgeb Ferfahr*, 162(3):326-240 (1995) PMID: 7718780 [PubMed-indexed for MEDLINE] Abstract.
Voskerician, G., et al., "High molecular weight kininogen inhibition of endothelial cell function on biomaterials," *J Biomed Mater Res*, 51(1):1-9 (Jul. 2000) PMID: 10813738 [PubMed-indexed for MEDLINE] Abstract.
Wachol-Drewek, Z., et al., "Comparative investigation of drug delivery of collagen implants saturated in antibiotic solutions and

(56) References Cited

OTHER PUBLICATIONS sponge containing gentamycin," *Biomaterials*, 17:1733-1738 (1996) PMID: 8866036 [PubMed-indexed for MEDLINE] Abstract.

Walluscheck, K.P., et al., "Improved endothelial cell attachment on ePTFE vascular grafts pretreated with synthetic RGD-containing peptides," *Eur J Vasc Endovasc Surg*, 12(3)321-330 (Oct. 1996) PMID: 8896475 [PubMed-indexed for MEDLINE] Abstract.

Walpoth, B.H., et al., "Improvement of patency rate in heparin-coated small synthetic vascular grafts," *Circulation*, 98(19 Suppl):II319-23: discussion II324 (Nov. 1998) PMID: 9852921 [PubMed-indexed for MEDLINE] Abstract.

Wengrovitz, M., et al,. "Thrombolytic therapy and balloon catheter thrombectomy in experimental femoral artery thrombosis: effect on arterial wall morphology," *J Vasc Interv Radiol*, 6(2):205-210 (1995) PMID: 7787354 [PubMed-indexed for MEDLINE] Abstract.

Westerband, A., et al., "Immunocytochemical determination of cell type and proliferation rate in human vein graft stenoses," *J Vasc Surg*, 25(1):64-73 (Jan. 1997) PMID: 9013909 [PubMed-indexed for MEDLINE] Abstract.

Winkler, T.A., et al., "Study of thrombus from thrombosed hemodialysis access grafts," *Radiology*, 197(2):461-465 (1995) PMID: 7480694 [PubMed-indexed for MEDLINE] Abstract.

Wissink, M.J., et al., "Endothelial cell seeding on crosslinked collagen: effects of crosslinking on endothelial cell proliferation and functional parameters," *Thromb Haemost*, 84(2):325-331 (Aug. 2000) PMID: 10959708 [PubMed-indexed for MEDLINE] Abstract.

Wolfle, K.D., et al., "Value of interventional procedures in treatment of stenotic occluded infra-inguinal vascular bypasses," *Zentralbl Chir*, 119(2):115-123 (1994) PMID: 8165880 [PubMed-indexed for MEDLINE] Abstract.

Young, A.T., et al., "Thrombosed synthetic hemodialysis access fistulas: failure of fibrinolytic therapy," *Radiology*, 154(3):639-642 (1985) PMID: 3969465 [PubMed-indexed for MEDLINE] Abstract.

Zaleski, G.X., et al., "Angioplasty and bolus urokinase infusion for the restoration of function in thrombosed Brescia-Cimino dialysis fistulas," *J Vasc Interv Radiol*, 10(2 Pt 1):129-136 (1999) Abstract.

Zdanowski, Z., et al., "Influence of some plasma proteins on in vitro bacterial adherence to PTFE and Dacron vascular prostheses," *APMIS*, 101(12):926-932 (Dec. 1993) PMID: 8110449 [Pub-Med-indexed for MEDLINE]Abstract.

Zou, Y., et al., "Mouse model of venous bypass graft arteriosclerosis," *Am J Pathol*, 153(4):1301-1310 (Oct. 1998) PMID: 9777962 [PubMed-indexed for MEDLINE]Abstract.

Zwaan, M. et al., "Thrombotic and thromboembolic occlusions of leg arteries and bypass. Short-term versus long-term lysis," *Rofo Fortschr Geb Rontgenstr Neuen Bildgeb Verfahr*, 158(6):536-541 (1993) PMID: 8507844 [PubMed-indexed for MEDLINE] Abstract.

No Author listed, "Results of a prospective randomized trial evaluating surgery versus thrombolysis for ischemia of the lower extremity. The STILE trial," *Ann Surg*, 220(3):251-266 (1994) PMID: 8092895 [PubMed-indexed for MEDLINE] Abstract.

Almin, C., et al., "Antibiotic loaded chitosan bar. In vitro, in vivo study of a possible treatment for osteomyelitis," *Clin Orthop*, 239-247 (1999).

Hermann, S.M., et al., "Polymorphisms of the human matrix Gla-protein gene (MGP) vascular calcification and myocardial infarction," *Arterioscler Thromb Vasc Biol* 20:2836-2893 (2000) PMID: 11073842 [PubMed-indexed for MEDLINE] Abstract.

Price, P., et al., "Warfarin causes rapid calcification of the elastic lamellae in rat arteries and heart valves," *Atheroscler Thromb Vasc Biol*, 18 1400-1407 (1998) PMID: 9743228 [PubMed-indexed for MEDLINE] Abstract.

Yao, L., et al., "Troglitozone decreases collagen accumulation in prediabetic stage of a type II diabetic rat model," *Heart*, 84:209-210 (2000) PMID: 10908265 [Pub-Med-indexed for MEDLINE].

Pakkanen, T.M., et al. "Periadventitial lacZ gene transfer to pig carotid arteries using a biodegradable collagen collar or wrap of collagen sheet with adenoviruses and plasmid-liposome complexes." J. Gene. Med. Jan.-Feb. 2000; 2(1): 52-60.

Merce, R., et al. "Modulation of apoptosis, proliferation, and p27 expression in a porcine coronary angioplasty model." *Atherosclerosis*, vol. 153, Issue 2, Dec. 2000, pp. 315-322.

Poon, M., et al. "Rapamycin inhibits vascular smooth muscle cell migration." J. Clin. Invest. (1996); vol. 98, Issue 10, pp. 2277-2283.

Teomin, D. et al. "Perivascular delivery of heparin for the reduction of smooth muscle cell proliferation after endothelial injury." Journal of Controlled Release, vol. 60, Issue 1, Jun. 28, 1999, pp. 129-142.

Villa, A.E., et al. "Local delivery of dexamethasone for prevention of neointimal proliferation in a rat model of balloon angioplasty." J. Clin. Invest. vol. 92, Mar. 1994, pp. 1243-1249.

EP Search Report for EP App. No. 10176383.7 dated Mar. 24, 2011.

JP Office Action for JP App. No. 2008877246 dated Dec. 2011.

Lee, David P., M.D., Power-point slide presentation, Presented at the Stanford University Interventional Cardiology Drug-Eluting Stent Conference, Jan. 18, 2003, "ABT-578: A New Approach to Drug-Eluting Stents", published via Internet, available at http://cvmed.standford.edu/interventional.

Medtronic, Inc., Medtronic News Release, "Medtronic Announces Start of Endeavor Drug-Eluting Stent Trial", Jan. 7, 2003, published via Internet, available at http://www.medtronic.com/newsroom/news_20030107b_html.

Medtronic, Inc., Medtronic News Release, "Medtronic Announces Start of the Endeavor II Pivotal Clinical Trials for Its Drug-Eluting Stent", Jul. 17, 2003, published via internet, available at http://www.medtronic.com/newsroom/news_20030717a.html.

Medline copyright, 2003 MeSh Description of Neovascularization.

Pharmacotheraphy, A Pathophysiologic Approach, 2nd ed. Bauer at p. 15, 1st para, Elsevier, 1992.

Morris, RE, Cao W, Huang X, Gregory CR, Billingham ME, Rowan R, Shorthouse RA., Rapamycin (Sirolimus) inhibits vascular smooth muscle DNA synthesis in vitro and suppresses narrowing in arterial allografts and in balloon-injured carotide arteries: evidence that rapamycin antaganozes growth factor action on immune and nonimmune cells, Transplant Proc, Feb. 1995;27(1):430-1.

Neenan and Allcock, Poly (organophosphazene) bound drugs, Biomaterials 3:78-80(1982).

Okada et al., Localized Release of Perivascular Heparin Inhibits Intimal Proliferation after Endothelial Injury without Systemic Anticoagulation, Neurosurgery, 25:892-896 (1989).

Okada et al., Local Anticoagulation Without Systemic Effect Using a Polymer Heparin Delivery System, Stroke, 19:1470-1476 (1988).

Goodwin, et al., Intense Inflammatory Reaction to Heparin Polymer Coated Intravasular Palmaz Stents in Porcine Arteries Compared to Uncoated Palmaz Stents, CardioVascular and Interventional Radiology, DIO: 10.1007/s0020256200, Springer-Verlag New York, Inc. (2003).

Brara PS et al., Pilot trial of oral rapamycin for recalcitrant restenosis. Circulation, Apr. 8; 107(3): 1722-4 (2003).

Clowes et al., Suppression by Heparin of Smooth Muscle Proliferation in Injured Arteries, Nature, vol. 265:625-626 (1977).

Ferns, G., Am J. Path. 137:403 (1990).

Jonasson, L., Proc. Natl, Acad. Sci. 85:2303 (1988).

Langer R., et al., Polymers for the sustained release of proteins and other macromolecules, Nature 263:797-800 (1976).

Marx So, et al., Rapamycin-FKBP inhibits cell cycle regulators of proliferation in vascular smooth muscle cells, Circ Res, Mar;76(3);412-7 (1995).

Mayberg et al., Thrombus prevention without systemic Anticoagulation: Localized polymeric Drug Delivery of Heparin. Surgical Forum XXIX 49609 Presented Oct. 1988 at the 87th Clinical Congress of the American College of Surgeons (1988).

Miller PE, et al., Natural history of arteriovenous grafts in hemodialysis patients, Am J. Kidney Dis, Jul:36(1):68-74 (2000).

Edelman et al., Perivascular graft heparin delivery using biodegradable polymer wraps, Biomaterials 21 (2000) 2279-2286.

Hirigoyen et al., Periadventitial Delivery of Heparin in the Prevention of Microvenous Thrombosis, J Oral Maxillifac Surg 54:1097-1102 (1996).

Website informational bulletin, "Drug delivery technologies and markets", website location: http://www.marketresearch.com/pr.../display.asp?ProductID=27371 Apr. 23, 2001.

(56) References Cited

OTHER PUBLICATIONS

Website press release, "Boston Scientific reports zero restenosis through nine months in paclitacel-coated stent clinical" Angiotech Pharmaceuticals, Vancouver, B.C. Canada, Feb. 26, 2002.
Results of computer-based search under keywords: Taxal, Paclitaxel, and Rapamycin.
Vranderic, MO., "New graft for the surgical treatment of small vessel diseases", Am. J. Surg. 28(6): 711-4 (May 1994) PMID: 3499440 [PubMed-indexed for MEDLINE].
Russell, Joanna, Website article on rapamycin found under www.ch.ic.ac.uk/local/projects/russell. No date or other citation information given.
No arthur given, "Rapamycin (FRAP/mTOR/Inhibitor)", #9904 Data Sheet; Website article on rapamycin found at www.cellsignal.com/products/us/9904.html. No date or other citation information given.
No arthur given, "Sirolimus-Brand Name: Rapamune", #4046.2171, Website article on the drug sirolimus a/k/a rapamune found at http://my.webmd.com/drug_article/article/5056.2171?bn+Rapamune. No date or other citation information given.
Depart. of Chemical and Nuclear Engineering, U of NM, "Tissue reaction to intraperitoneally implanted catheter materials" J Biomed Eng, 13(2):173-5 (Mar. 1991). PMID: 2033954 [PubMed-indexed for MEDLINE].
The Canadian Multicenter Hemashield Study Group, "Immunologic response to collagen-impregnated vascular grafts: randomized prospective study", J Vasc Surgery 12(6): 741-6 (Dec. 1990). PMID: 2147043, UI: 91056629.
Schindhelm, James NL et al., "Endothelial cell seeding of small diameter vascular grafts", Centre for Biolmedical Engineering, U of South Wales, 14(5): 355-60 (Oct. 1999). PMID: 22411603, UI: 91053802.
Katz, John & Spera, Gabriel, "Biomaterials research focuses on developing new applications", Medical Device & Diagnosis Industry, 1998. Website link: www.devicelink.com/mddi/archive/98/04/005.html.
No author given, "Cohesion gets CE mark for coseal surgical sealant", Cohesion Technologies, Inc., 1999. Website www.findarticles.com/m0DHC/5_12/615658332/pl/article.mhtml04/23/01.
No author given, "How does suture material type impact needle hole bleeding when suturing PTFE vascular grafts?", Vascular Graft Technical Data, No. 1, Atrium Medical Corporation, Hudson, NJ, no date given.
No author given, "What can be done to help prevent and manage seromas with PEFE vascular grafts?", Vascular Grat Technical data, Atrium Medical Corporation, Hudson, NH, no date given.

\* cited by examiner

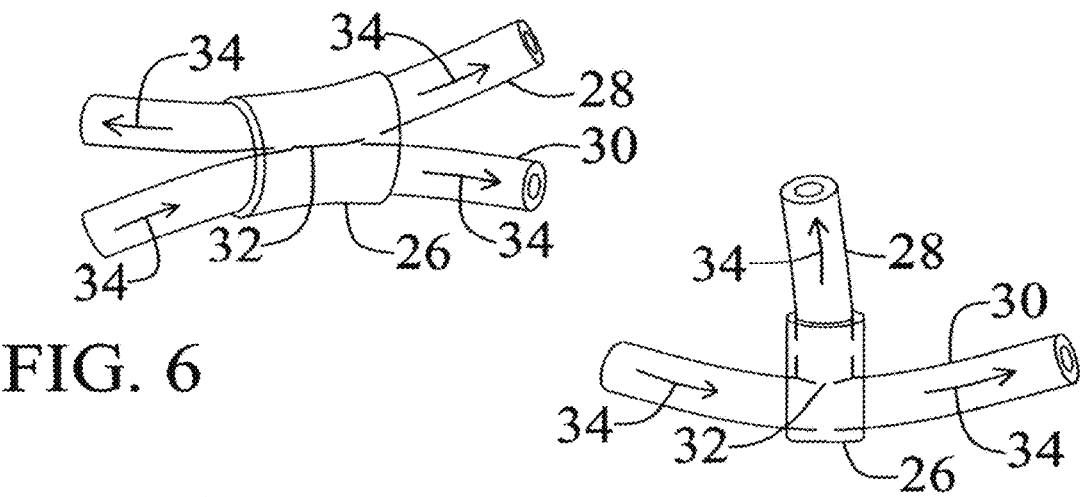
FIG. 6
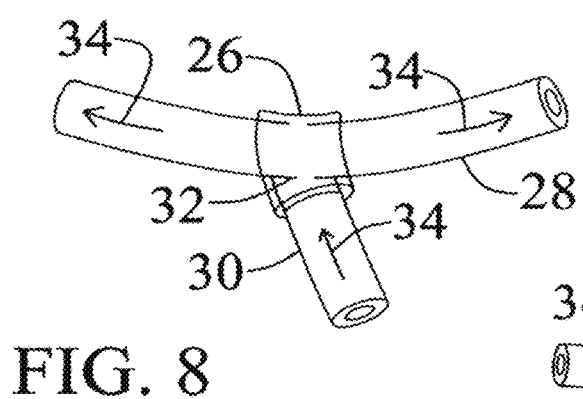
FIG. 7
FIG. 8
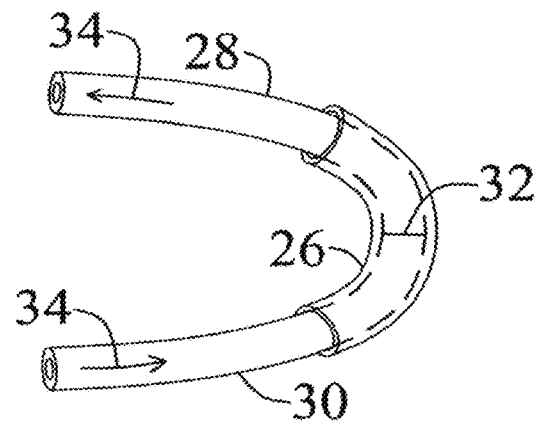
FIG. 9

FIG. 12
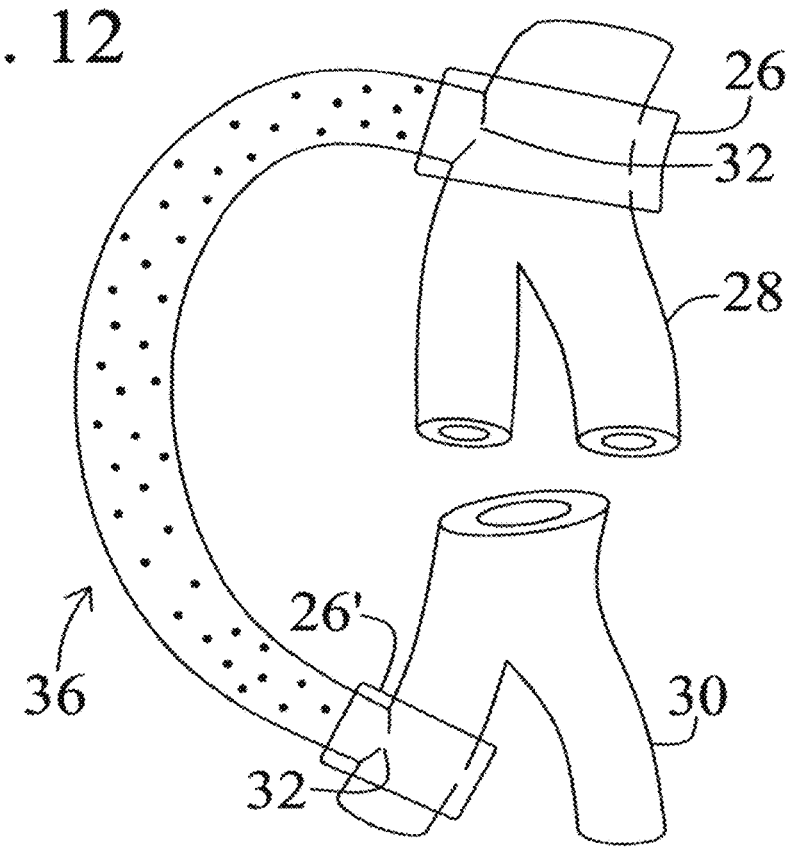
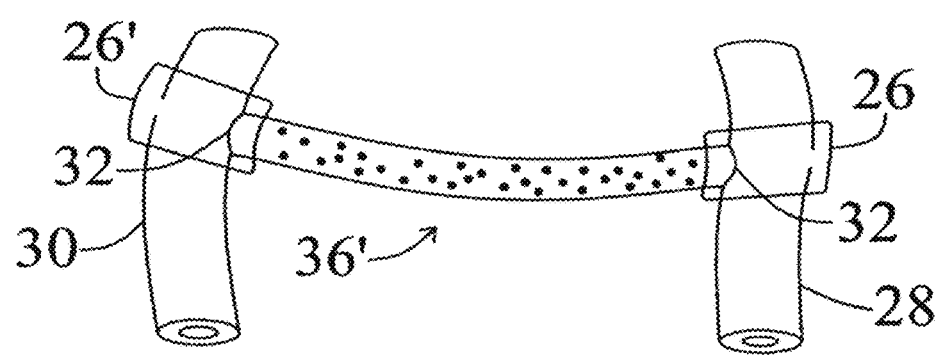
FIG. 13

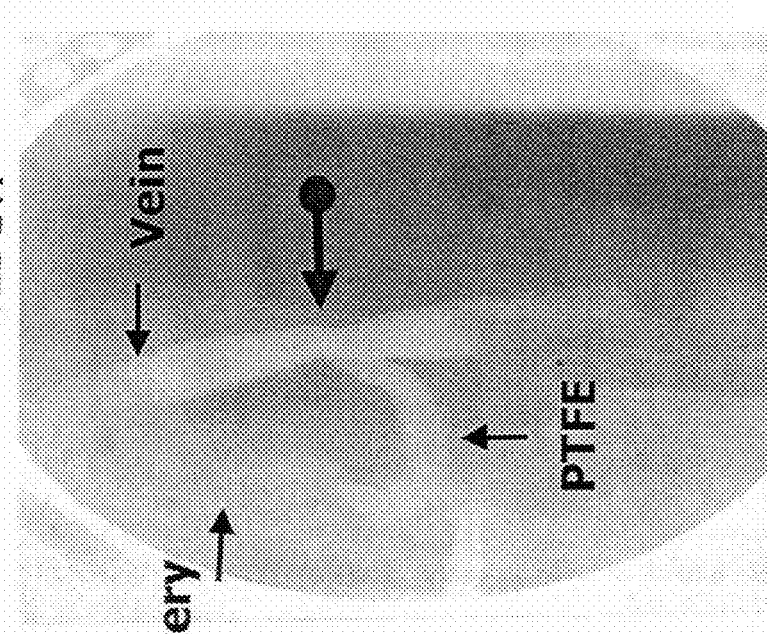
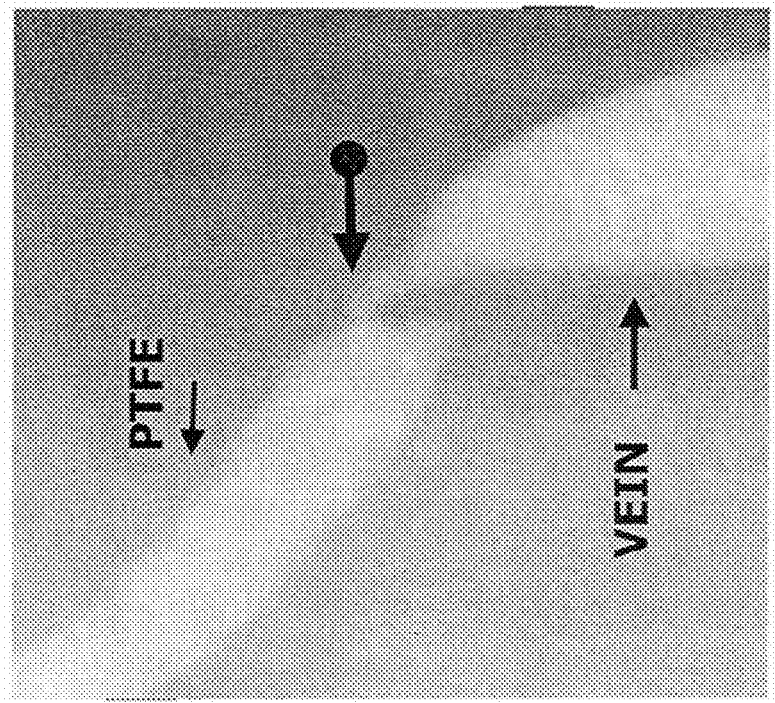
Fig 18A / Fig 18B
Four Week Follow Up Angiograms
Arrow with circle on tail indicate site of anastamosis

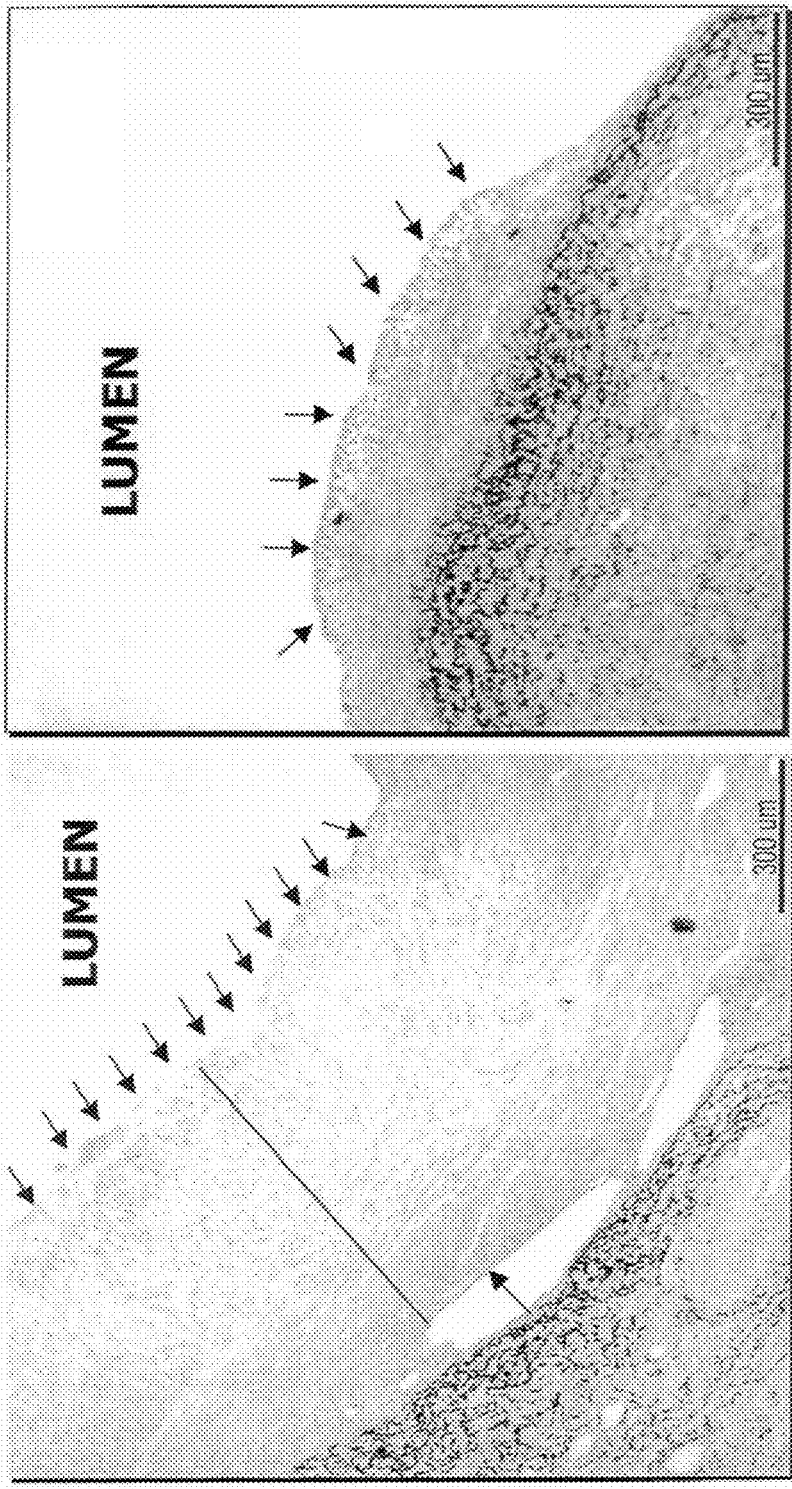

APPARATUS AND METHODS FOR PREVENTING OR TREATING FAILURE OF HEMODIALYSIS VASCULAR ACCESS AND OTHER VASCULAR GRAFTS

CROSS-REFERENCED TO RELATED APPLICATIONS

Not applicable

STATEMENT REGARDING FEDERALLY SPONSORED RESEARCH OR DEVELOPMENT

Not Applicable

BACKGROUND OF THE INVENTION

Failure of hemodialysis vascular access and other vascular grafts becomes evident as compromise of the lumen of the native vessel (vein or artery) or of the prosthetic conduit at o or away from the anastamotic site. Compromise of the lumen manifests as either stenosis or occlusion and is a result of either intraluminal thrombus and/or a vasculoproliferative response. The etiology of graft failures may be related to a variety of physical (e.g., shear stress causing hemodynamic disturbance), chemical and/or biological stimuli as well as infection and foreign body rejection which may explain why fistulae which do not involve a foreign body (in this case, for example, polytetrafluroethylene, PTFE) remain patent for a longer time compared to vascular access grafts that involve interposition of a PTFE graft.

The present invention relates generally to therapeutic implant, apparatus and methods useful for preventing, suppressing (inhibiting) or treating failure of hemodialysis vascular access and other vascular grafts.

Vascular access grafts, specifically, hemodialysis access grafts are well known to the art. Approximately 100,000 vascular access procedures are performed yearly in the United States. Hemodialysis vascular access can be constructed in one of several ways: as an arterio-venous fistula (e.g.; Brecisa-Cimino), or as a graft, interposing either prosthetic (e.g., PTFE) or biologic tissue (e.g., vein) between the artery and the vein. Such grafts are usually constructed using a tubular or cylindrical segment of suitably bio-compatible, substantially inert material such as polytetrafluoroethylene (PTFE). In fact, PTFE is the most common material used for prosthetic dialysis access. In one approach, a segment of PTFE is surgically interposed between an artery and a vein in the arm, forearm or thigh. The graft is then available for repeated vascular access for performing hemodialysis.

Subsequent to placement of the access graft the sutured sites in the artery and the vein undergo healing. Sixty percent of these grafts fail each year, usually because of narrowing (stenosis) at the venous end. Similar lesions develop in PTFE grafts placed in the arterial circulation, where there is a similar tendency for the distal end of the graft to be affected. Dysfunction or failure of veing grafts and/or other graft conduits used in coronary artery bypass graft surgery or in peripheral vascular surgery (e.g., aorta-iliac, femoral-femoral, femoral-popliteal, femoral tibial, etc.) are well known. Development of arterial access graft stenosis is not as rapid as development of access graft stenosis at the venous end. Proliferation and migration of smooth muscle cells resulting in intimal hyperplasia in the vein and the adjacent graft orifice has been described in human dialysis access stenosis. As the stenosis in the graft becomes progressively more severe, the graft becomes dysfunctional and hemodialysis is suboptimal. If the stenosis in the graft is not treated, it eventually leads to occlusion and to graft failure.

The reasons why the venous ends of access graft have such a marked propensity for narrowing are multifactorial. Features unique to this location include exposure to arterial pressures and arterial flow rates, dissipation of acoustic (vibratory) energy in the vessel wall and surrounding tissue, repeated puncture of the graft, and infusion of processed blood. In addition, the venous end of the graft may be bathed in mitogens released during passage of the blood through the dialysis tubing or during activation of platelets at the site of needle puncture.

Tissue samples collected from the graft-vein anastomosis site of stenotic PTFE grafts during surgical revision showed significant narrowing of the lumen and were characterized by the (i) presence of smooth muscle cells, (ii) accumulation of extra-cellular matrix, (iii) angiogenesis within the neointima and adventitia, and (iv) presence of an active macrophage cell layer lining the PTFE graft material. A large variety of cytokines and cell growth stimulating factors like platelet-derived growth factor (PDGF), basic fibroblast growth factor (bFGF), and vascular endothelial growth factor (VEGF) were expressed by smooth muscle cells/myofibroblasts within the venous neointima, by macrophages lining both sides of the PTFE graft, and by vessels within the neointima and adventitia. It has been suggested that macrophages, specific cytokines (bFGF, PDGF, and VEGF), and angiogenesis within the neointima and adventitia are likely to contribute to the pathogenesis of venous neointimal hyperplasia (VNH) a manifestation of the vasculoproliferative response in PTFE dialysis grafts.

Survival of patients with chronic renal failure depends on optimal regular performance of dialysis. If this is not possible (for example as a result of vascular access dysfunction or failure), it leads to rapid clinical deterioration and unless the situation is remedied, these patients will die. Vascular access dysfunction is the most important cause of morbidity and hospitalization in the hemodialysis population in the United States at an estimated cost of approximately one billion US dollars per annum. Venous neointimal hyperplasia characterized by stenosis and subsequent thrombosis accounts for the overwhelming majority of pathology resulting in PTFE dialysis graft failure. Despite the magnitude of the problem and the enormity of the cost, there are currently no effective therapies for the prevention or treatment of venous neointimal hyperplasia in PTFE dialysis grafts. Consequently, interventions aimed at the specific mediators and processes may be successful in reducing the very significant human and economic costs of vascular access dysfunction.

Once the stenosis has occurred, one of the current methods of treatment involves reduction or obliteration of the narrowing and restoration of blood flow through the graft (permitting the performance of adequate hemodialysis) by means of non-surgical, percutaneous catheter based treatments such as balloon angioplasty. Balloon angioplasty, in one aspect, involves deployment of a balloon catheter at the site of the blockage and inflating the balloon to increase the minimum luminal diameter (MLD) of the vessel by compressing the material causing the restriction against the interior of the vessel wall, thereby dilating the vessel. Depending upon the length and severity of the restriction, the procedure may be repeated several times (by inflating and deflating the balloon). When completed, the balloon catheter is withdrawn from the system.

Although balloon angioplasty can be used as a "stand alone" procedure, it is frequently accompanied by deployment of what is called a stent. A stent is an expandable scaffolding or support device which is placed within the vasculature to prevent mechanical recoil and reduce the chance of renarrowing (restenosis) at the site of the original restriction. Stents are either "balloon-expandable" or "self-expanding" and when deployed endovascularly, abut against the inner vessel wall. Whether or not a stent is placed, this form of treatment has a high risk of failure i.e., the risk of renarrowing (restenosis) at the treatment site is very high. Unless stenosis within the access graft can be effectively and permanently treated, graft failure tends to follow. In the event of graft failure, the patient has to undergo an endovascular procedure i.e., a non-surgical, catheter-based percutaneous procedure, repeat vascular surgery e.g., thrombectomy to "declot" the graft or to place another vascular access graft or a shunt (as it is sometimes referred to) at a different site, unless the patient receives a kidney transplant. Given the obvious problems of repeat surgery(ies) and the limited availability of transplants, there is a need for a treatment that is both effective and long lasting (durable) in the prevention and treatment of dialysis graft stenosis.

The vast majority of current approaches for reducing or preventing the vasculoproliferative response (believed to be the pathophysiological basis of restenosis), are based on treatment options that originate from within the vascular or graft lumen. One current, novel approach utilizes drug coated or drug impregnated stents which are then deployed within the lumen of the blood vessel. Examples of drugs used to coat stents include Rapamycin commercially available from the Wyeth Ayerst company (Sirolimus®), and Paclitaxel commercially available from the Bristol-Myers Squibb Company (Taxol®). In this stent-based approach, Rapamycin or Paclitaxel is gradually eluted from the stent and diffuses into the vessel wall from the intima (the innermost layer of the vessel wall) to the adventitia (the outermost layer of the vessel wall). Studies have shown that Rapamycin and Paclitaxel tend to inhibit smooth muscle cell proliferation.

Delivery from the perivascular or extravascular space through the arterial or vascular wall utilizing a synthetic matrix material (ethylene-vinyl acetate copolymer, EVA) together with an anticoagulant that also has antiproliferative properties e.g., heparin, has been suggested. There are two disadvantages of this approach: heparin is a soluble substance and rapidly disappears from the vascular wall and, ethylene-vinyl acetate copolymer is not biodegradable potentially raising concerns about long term effects, in vivo.

If a therapeutic agent is delivered locally using a matrix material-based system, the matrix material should preferably have the following characteristics:

1. The matrix material has to permit the loading of adequate quantity of the therapeutic agent.
2. The matrix material must elute the therapeutic agent at an appropriate, well defined rate.
3. The matrix material should preferably be implantable and biodegradable. Thus, physical removal of the matrix material from recipient's tissue following drug delivery would not be necessary and obviates concerns about the long term effects of the residual matrix.
4. Neither matrix material nor its biodegradation products should provoke a significant inflammatory or proliferative tissue response, nor should they alter or interfere with the recipient's natural defense systems or healing.
5. The device (comprising the matrix material and the drug) should be flexible enough to mould to the contours of the vasculature and
6. The device should be amenable to be fixed in place preventing its migration to an unintended location.

Polymer matrix materials used for drug delivery within the context of implantable devices can be either natural or synthetic. Examples include but are not limited to polymers composed of chemical substances like polyglycolic acid or polyhydroxybutyrate, EVA or natural polymers like collagen, fibrin or polysaccharides like chitosan. However, not all of these matrix materials are ideal; inappropriate features include poor mechanical characteristics, potential immunogenicity, and cost. In addition, some may produce toxic degradation products and induce inflammatory reactions or a proliferative response.

A well known biocompatible, biodegradable, resorbable matrix material for drug delivery is collagen. The use of collagen as a material for fabrication of biodegradable medical devices is and has undergone serious scrutiny. U.S. Pat. Nos. 6,323,184, 6,206,931; 4,164,559; 4,409,332; 6,162,247. One current focus involves delivery of pharmaceutical agents including antibiotics and physiologically active proteins and peptides such as growth factors.

Under scanning electron microscopy, the collagen matrix has a morphology of condensed laminated film with a textured surface and a range of pore sizes. It can be produced in a wide range of effective pore sizes from 0.001 microns to 100 microns or even larger. This internal pore network (porous material) creates a high surface area and serves as a microreservoir for storage and delivery of the therapeutic agent. Several features make collagen an excellent and ideal matrix material for drug delivery. Collagen exhibits a high degree of flexibility and mechanical durability, as well as intrinsic water wettability, semipermeability and consistent flow characteristics. More importantly, collagen, a naturally occurring substance is biodegradable and non-toxic. In addition, collagen has favorable biodegradation characteristics and time to complete degradation or resorption i.e., durability of the collagen matrix for drug delivery can be modified.

A second protein matrix suitable for drug delivery is fibrin. A fibrin matrix is comprised of cross-linked fibrin units that are a reticular network of thrombin-modified fibrinogen molecules. This matrix is similar to a natural blood clot. In contrast to natural clot, the size of pores in a fibrin matrix can be controlled and varies from 0.001 millimicrons to 0.004 millimicrons, so-called micropores. The differences in pore sizes between collagen and fibrin matrices permit the binding of therapeutic agents with distinct rates of drug release. The ability to control bleeding, to remain firmly fixed in place, and to be naturally biodegradable have all made fibrin a good matrix material for drug delivery and confers fibrin some advantages over synthetic matrices. Most of the early applications of fibrin as a matrix were for delivery of antibiotics and other biologics.

The fibrin matrices are prepared in a dry granular form. (cf., PCT/EP99/08128). This formulation, manufactured by HyQ Solvelopment, Buhlmhle, Germany, contains D-mannitol, D-Sorbit, fibrinogen-aqueous solution, and a thrombin-organic suspension. The formulation is manufactured by fluid bed granulation. The applications for dry fibrin are manifold: wound closure, promotion of healing, and homeostasis. However, application for drug delivery is limited since such a formulation does not allow for a target-oriented shaping of solid particles around the vessel wall and delivery of exact dosages is difficult. Porosity and capacity of dry fibrin particles are low, physical stability is poor.

Another group of potentially useful resorbable, natural polymer matrix material is chitosan. Chitosan has proven to be a useful biocompatible aminopolysaccharide and a matrix for controlled release of the agent for local delivery. Chitosan implants cause no systemic and local side effects or immunologic responses, and are suitably biodegradable. Chitosan can be prepared from the degradation of slow chitin (molecular weight $1 \times 10^6$) using high temperature sodium hydroxide hydrolysis to a molecular weight of $5 \times 10^5$. The inability to control porosity is a disadvantage of this matrix material.

BRIEF DESCRIPTION OF THE PRESENT INVENTION

The present invention is unique in at least two respects: 1) Whereas the majority of current methods of preventing suppressing or treating the vasculoproliferative response (smooth muscle cell hyperplasia, restenosis, vascular occlusion) do so from inside the vascular (i.e., vein and/or artery) or graft lumen, the present invention is a method of doing so extravascularly or perivascularly i.e., from outside the vascular or graft lumen and through the vascular wall. 2) All current treatment approaches are relevant only after the narrowing or stenosis has actually taken place. The current invention is, in one aspect, a method of preventing or suppressing vasculoproliferative disease, in contradistinction to curing it.

In a further embodiment, the present invention is an implantable prosthetic device placed on the outer surface of the vessel or graft which then elutes anti-vasculoproliferative drugs or agents such as Rapamycin, Paclitaxel, Tacrolimus, and other cell cycle inhibitor or similarly-functioning agents. In addition to a resorbable matrix material, e.g., protein, and an antiproliferative agent, this implantable device contains optionally, agents that inhibit collagen accumulation in the tunica media and adventitia of the vascular wall and pharmaceuticals that help reduce calcification of the vascular wall. This invention provides a method of preventing or treating neo intimal hyperplasia (an expression of the vasculoproliferative response) and calcification by extravascular delivery of an effective amount of an antiproliferative agent with low water solubility alone or in combination with adjuvants, and other antiproliferative agents. Rapamycin is a particularly preferred drug with antiproliferative properties for use with the present invention. A mixture of suitable drugs may be used. The Rapamycin diffuses from the outside and through the vessel and/or graft wall to the interior of the vein and/or artery and/or graft. Elution of Rapamycin (and other drugs with antiproliferative effect), into and through the vascular wall from the outside starts soon after the device is implanted and the drug will inhibit smooth muscle cell proliferation within the hemodialysis and other vascular grafts and/or at their anastamotic sites. Thus, in one aspect, the present invention is a method of inhibiting smooth muscle cell proliferation of a vascular access graft or shunt by the gradual elution or timed release of a drug from outside the vascular access site vessel wall to the vessel interior i.e., by extravascular or perivascular delivery.

In another aspect the present invention is a prosthetic device comprising a cylindrical, antiproliferative-imbibed, protein interior layer and, optionally, an exterior support or skeletal structure or layer. In one embodiment, the imbibed protein layer is collagen and the exterior skeletal support structure is a sheet of PTFE. The antiproliferative drug, in this embodiment, is preferably Rapamycin. Paclitaxel (or Taxol) is another antiproliferative drug or agent well-suited to the embodiment of the invention.

A third embodiment of the present invention is a method of inhibiting stenosis of hemodialysis access graft comprising the method of placing a prosthetic device (described above) over a graft or vascular structure and/or at the site of anastomosis and anchoring the prosthetic device at the desired site (e.g., by suturing).

A device of this invention may employ a biocompatible matrix material such as collagen, fibrin or chitosan. An important factor in the selection of a particular matrix material is the porosity of the material and a controllable rate of biodegradation. Use of a matrix material is important because it creates a delivery reservoir and controls the agent delivery kinetics.

A preferred device of this invention comprises a collagen matrix material imbibed with Rapamycin, which will be placed in position so as to extravascularly deliver the agent.

In a preferred embodiment, about 120 micrograms/$cm^2$ of Rapamycin (Range: 50 micrograms to 10 mg/$cm^2$) is combined with a collagen matrix material sheet with a thickness in the dry state between 0.3 and 2.0 mm sheet which is then implanted or wrapped upon the outside of the vascular or graft wall.

A further aspect of the present invention is "self fixation" of the device delivering the drug or agent to the outer surface of the vascular or graft wall. The collagen-device could be made more adhesive to the vascular wall if in the final stage collagen is combined with photoreactive groups such as FITS (fluorescein isothiocyanate) or Bengal Rose both from Sigma Chemicals, St Louis, Mo. Stimulation of the device with ultra violet light will activate these photoreactive groups and will increase adhesion. Fibrin sealant and acetylated collagen also have been found to increase adhesion of collagen matrix material to the outside vascular wall.

Early work showed a relationship between local vessel trauma and expedited calcification. Recently, a study in humans has shown that the matrix Gla-protein (protein γ-carboxylated vitamin K-dependent γ-carboxylase) is constitutively expressed by normal vascular smooth muscle cells and bone cells. High levels of Gla-protein mRNA and non-γ-carboxylated protein were found in atherosclerotic vessel tissues. This γ-carboxylated protein is necessary to prevent or postpone beginning of vascular calcification (Price, P. et al., "Warfarin causes rapid calcification of the elastic lamellae in rat arteries and heart valves," *Atheroscler Thromb Vasc Biol*, (1998) 18: 1400-1407). These data indicate that calcification caused by injury must be actively inhibited. Introduction of pharmaceuticals preventing calcium accumulation helps to postpone calcification and helps prevent, suppress or treat the vasculoproliferative processes. In one aspect of this invention, local delivery of Vitamin K counteracts the calcification effect associated with vessel injury by timely activation of γ-carboxylase (in this case Gla-protein) and ensures other calcium-binding proteins function properly and do not bind excess of calcium (Hermann, S. M. et al., "Polymorphisms of the human matrix Gla-protein gene (MGP) vascular calcification and myocardial infarction," *Arterioscler Thromb Vasc Biol*. (2000) 20:2836-2893. A mixture of Vitamin K and other antiproliferative drugs may be used.

The acute response, characterized by an inflammatory reaction, is an attempt to limit disturbances in the homeostasis. Hallmarks of this inflammatory reaction include leukocyte accumulation, increased fibrin deposition and release of cytokines. Addition of synthetic glucocorticoids like dexamethasone decreases this inflammatory response and may eventually decrease the vasculoproliferative process. Since the pharmacological mechanisms of action of the antiproliferative agents and synthetic glucocorticoids are different, agents with different "mechanisms of action" may be expected to act synergistically. It may be useful, therefore, to combine two or more of these agents.

This invention thus provides a method of preventing, suppressing, or treating neointimal hyperplasia by extravascular, (e.g., perivascular) local delivery of an effective amount of an anti-vasculoproliferative agent with low water solubility (e.g., Rapamycin) alone or in combination with other antiproliferative agents and adjuvants.

In one aspect, the present invention is a prosthetic device that consists of a resorbable protein matrix combined with a drug, placed on the outer surface of a blood vessel or graft. The device then elutes the drug which inhibits smooth muscle cell proliferation (anti-vasculoproliferative). Examples of such drugs include Rapamycin, Paclitaxel, Tacrolimus, other cell cycle inhibitors or similarly-functioning agents. A mixture of suitable drugs and/or additives may be used. In addition to a resorbable protein matrix and an antiproliferative agent, this implantable device contains optionally, agents that inhibit collagen accumulation in the vascular wall and pharmaceuticals that help reduce calcification of the vascular wall.

Rapamycin is a particularly preferred drug for use with the present invention. The Rapamycin [or other drug(s)] elutes from the outside and diffuses through the vessel and/or graft wall to the interior of the vein and/or artery and/or graft. Elution of Rapamycin (or a similarly acting drug or a drug having similar properties), into and through the vascular wall from the outside takes place during the healing phase of the anastamotic sites and the drug will prevent suppress/inhibit or treat smooth muscle cell proliferation that accompanies such healing. Thus, in one aspect, the present invention is a method of inhibiting the vasculoproliferative response at the anastamotic ends of a vascular access graft or shunt by the gradual elution or timed release of a drug from outside to the vessel interior i.e., by transvascular delivery using an extravascular source.

In another aspect the present invention is a prosthetic device comprising a antiproliferative-imbibed, protein interior layer and, optionally, an exterior support or skeletal structure or layer. In one embodiment, the imbibed protein layer is collagen and the exterior skeletal support material structure is a sheet of PTFE. The antiproliferative drug, in that embodiment, is preferably Rapamycin, or other similarly-functioning drugs.

Another embodiment of the present invention is a method of inhibiting stenosis of hemodialysis access graft comprising the method of placing the prosthetic device (described above) over a graft or vascular structure and/or at the site of anastomosis and anchoring the prosthetic device at the desired site (e.g., by suturing).

BRIEF DESCRIPTION OF FIGURES

FIGS. 2A and 2B illustrate another embodiment of the present invention in which an exterior support or skeletal structure are employed.

FIGS. 6-13 Illustrate various possible deployments of the drug-eluting sleeve of the present invention in view of various vessel reparative needs.

FIGS. 18A, 18B, 19A, 19B, and 20 illustrate some results obtained using the present invention.

DETAILED DESCRIPTION OF THE INVENTION

Figure 1A:
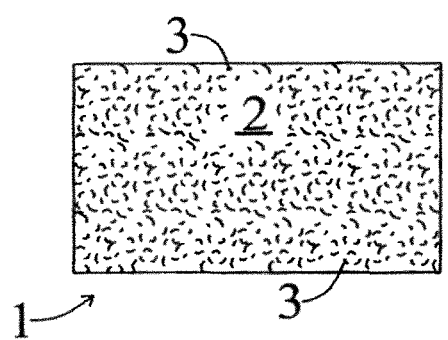
FIGS. 1A, 1B, 2A, and 2B illustrate preferred embodiments of the present invention.

In one aspect the present invention is a prosthetic device adapted for extravascular drug or agent delivery comprising a drug or agent-eluting matrix material combined with a drug(s) that can prevent, suppress or treat vasculoproliferation.

Matrix Materials: Material for the matrix may be from natural sources or may be synthetically manufactured or may be a combination of the two. A device of this invention may employ a biocompatible, biodegradable resorbable matrix material such as collagen, fibrin or chitosan. A suitably biocompatible, nonbiodegradable matrix may be also be used. Combination of degradable and nonbiodegradable or two or more biodegradable substances (e.g., collagen plus fibrin) or two or more nonbiodegradable substances may be selected for the matrix material. An important factor in the selection of a particular matrix material is the porosity of the material and where applicable, a controllable rate of biodegradation. The characteristics of the matrix material is important because the material creates a delivery depot or reservoir and control the kinetics of agent delivery. The characteristics with respect to thickness, porosity, rate of biodegradation etc. need not be identical throughout the matrix. It is also conceivable that by creating a polymer from the drug (for example, the antiproliferative), the matrix and the drug are one and the same, and, as the polymer degrades it releases the drug.

Collagen (Type I) is a preferred biocompatible biodegradable resorbable material for the matrix of the drug eluting sleeve of the present invention. The collagen source may be animal or human or may be produced using recombinant DNA techniques. Other types of collagen e.g., types II, III, V, XI singularly or in combination with Type I may be used. Although collagen matrix in the form of a sheet or membrane is the preferred embodiment of this invention, other forms of collagen e.g., gel, fibrilla, sponge, tubular etc., may also be used. As is well known, the rate at which resorption of the collagen occurs can be modified by cross-linking the protein.

Therapeutic Agents: In order to prevent suppress or treat the smooth muscle proliferative response that predominantly contributes to the neointimal hyperplasia, therapeutic agents that have significant antivasculoproliferative properties will be used in this invention. It is to be understood that as presently informed it is smooth muscle proliferation, which is believed to be primarily responsible for the stenosis and luminal compromise leading to graft failure. The present invention should not be interpreted to require that failure mechanism for its operation. Stated differently, applicants do not wish to be bound by any theory of graft failure, which would tend to narrow the scope of their invention. Examples of drugs with significant anti proliferative effects include but are not limited to Rapamycin, paclitaxel, other taxanes, tacrolimus, actinomycin D, angiopeptin, vassenoids, flavoperidol, hormones such as estrogen, halofuginone, matrix metalloprotienase inhibitors, ribosimes, interferons and antisense compounds. Analogues of the parent compound e.g., those of rapamycin, paclitaxel and tacrolimus may be used. Examples of other therapeutic agents include anti-inflammatory compounds, dexamethasone and other steroids, antiplatelet agents including aspirin, clopidogrel, IIBIIIA antagonists, antithrombins, anticoagulants including unfractionated and fractionated heparin, statins, calcium channel blockers, protease inhibitors, alcohol, botulin and genetic material. Vascular, bone marrow and stem cells may also be used These agents can be combined to the matrix singly or in combination. Depending on the therapeutic agent, the agent can be combined with the matrix using physical, chemical and/or biological methods. A combination of techniques can be used. It will also be appreciated that drug concentration need not be (and often will not be) the same throughout the entire matrix.

It is to be understood that the process of elution of drug from the matrix material (sleeve) to and through the vessel wall is merely illustrative of one possible drug delivery process. For example, a drug may be released by application of a stimulus or a trigger e.g., light, temperature variation, pressure, ultrasound-ionizing energy, electromagnetic or magnetic field. Also, the drug may reside in the matrix as a pro-drug or in an inactive form. Application of the stimulus referred to above triggers conversion to the active form of the drug which is then released. Illustrating this application, it is known that Porphyrins and Psoralens are activated and may be released from a matrix to which they are absorbed or bound, by application of visible or ultraviolet light. Application of light modifies the drug structure causing the association between the drug and the protein reservoir or source to be disrupted. Thus, the drug is released from its matrix or reservoir and elutes to and through the vessel wall and into the vessel lumen in accordance with this invention.

Adjuvants: A device of this invention optionally includes agents that accomplish other objectives e.g., that inhibit collagen accumulation and help reduce calcification of the vascular wall. Early work by Selye and colleagues showed a relationship between local vessel trauma and expedited calcification. Recently, a study in humans has shown that the matrix Gla-protein (protein γ-carboxylated vitamin K-dependent γ-carboxylase) is constitutively expressed by normal vascular smooth muscle cells and bone cells. High levels of Gla-protein mRNA and non-γ-carboxylated protein were found in atherosclerotic vessel tissues. This γ-carboxylated protein is necessary to prevent or postpone beginning of vascular calcification (Price P. et al., "Warfarin causes rapid calcification of the elastic lamellae in rat arteries and heart valves," *Atheroscler Thromb. Vasc. Biol.* (1998); 18:1400-1407). These data indicate that calcification caused by injury must be actively inhibited. Introduction of pharmaceuticals preventing calcium accumulation helps to postpone calcification and the restenotic processes. In this invention, local delivery of Vitamin K counteracts the calcification effect associated with vessel injury, by timely activation of γ-carboxylase (in this case Gla-protein) and ensures other calcium-binding proteins function properly and do not bind excess of calcium (Hermann S. M. et al., "Polymorphisms of the human matrix Gla-protein gene (MGP) vascular calcification and myocardial infarction, "*Arterioscler Thromb. Vase. Biol.* (2000); 20: 2836-93). A mixture of Vitamin K along with other anti-proliferative drugs may be used.

The acute response to any injury, (in this instance, surgical trauma) characterized by an inflammatory reaction, is an attempt to limit disturbances in the homeostasis. Hallmarks of this inflammatory reaction include leukocyte accumulation, increased fibrin deposition and release of cytokines. Addition of synthetic glucocorticoids like dexamethasone decreases this inflammatory response and may eventually decrease the restenotic process. Since the pharmacological mechanisms of action of the antiproliferative agents and synthetic glucocorticoids are different, agents with different "antirestenotic mechanisms" may be expected to act synergistically. It may be useful, therefore, to combine two or more of these agents.

Numerous other antiproliferative or anti-stenosis drugs and other suitable therapeutics and adjuvants will likely occur to one skilled in the art in light of the present disclosure.

Method of Making the Sleeve: In view of the above disclosure several potential processes for making the prosthetic device and for its application will occur to one skilled in the art.

Single or Uni Layer Device: In a preferred embodiment of this invention, the protein matrix is a sheet or membrane of Type I bovine collagen and the drug is Rapamycin. Collagen is a particularly preferred example for the matrix because it has the property of being biodegradable and reabsorbable. The durability of the matrix reflects the time to complete reabsorption of the collagen, the porosity influences the drug binding capacity of the collagen matrix, both of these features can be controlled and varied. As an example, a relatively flat sheet of collagen is impregnated, absorbed, saturated, dispersed or immobilized with Rapamycin. About 120 micrograms/cm$^2$ (Range: 50 micrograms-2 milligrams/cm$^2$) of Rapamycin is combined with the collagen matrix material which in the dry form is in the form of a sheet that is 0.3 to 2.0 mm thick. This drug combined collagen sheet (sleeve), modified into a tube (cylinder) or other geometrical shapes, is directly secured to the outside of the native vessel, at the site of graft anastamosis and/or over the vein, artery or graft itself. The device may be secured by sutures or staples. The suture material itself may be combined with an anti vasculoproliferative drug. In this aspect, the chosen antiproliferative agent permeates through the vessel wall the rate of drug elution from the membrane can be varied and can continue until the collagen matrix material is completely resorbed. Tacrolimus, paclitaxel, other taxanes, flavoperidol, antisense, analogues of Paclitaxel, Rapamycin and tacrolimus, and other adjuvants well known to one skilled in the art, may be used.

Double or Dual or Multi layer Device: In another aspect, the present invention is a dual layered prosthetic device comprising an antiproliferative-imbibed, inner matrix layer and, an external support skeletal structure or layer. In this embodiment, the inner matrix material is a sheet or membrane of type I collagen and the exterior skeletal support material structure is a sheet of PTFE. The antiproliferative drug, in this embodiment, is Rapamycin. The sheet of collagen will be attached to the PTFE sheet using a variety of techniques e.g., physically using sutures, adhesives, staples or the two may be chemically bonded. The two sheath composite would then be rolled to create either a tubular structure or geometrical variations thereof. The composite device or sleeve is then suitably trimmed so that it can be applied over the desired site(s): artery, vein, graft anastomotic site etc., and the free edges of the PTFE sleeve are attached to each other by adhesive, sutures, staples etc. This stabilizes the entire device on the outside of the vascular structure or graft. The drug then permeates through the vascular or prosthetic material wall and while in the wall the drug inhibits smooth cell proliferation, an integral part of the healing response that follows surgical construction of the graft.

Following placement on the outside of a vessel or prosthetic surface, after a period of time the body absorbs the collagen leaving its exterior support skeleton or structure intact. One skilled in the art will appreciate that the body-resorbable aspect of the protein layer chosen to imbibe the drug, is an optional preferred practice of the present invention. The PTFE not being bioabsorbable, tends to hold the resorbable protein layer in place for a length of time sufficient for the drug to permeate through the vascular or graft or prosthetic material wall. Besides its value in supporting the drug eluting inner membrane or matrix material there are other potential advantages of the external layer. Although the desired effect of the drugs is their ability to inhibit the smooth muscle cell proliferative response, it is this proliferative response that contributes to the formation of a good quality (firm) surgical scar. A weak scar at the site of surgical anastamosis can potentially lead to graft disruption or aneurysm formation. Having an external PTFE skeleton functions as an additional reinforcement layer and prophylactically addresses the treatment for problems related to a weak scar, graft disruption, and/or aneurysm formation. The external PTFE layer serves to keep the drug in close apposition with the outer aspect of the vessel or graft wall and limits its diffusion to the surrounding tissues and skin. It is also within the contemplation of the present invention that the exterior skeletal or support aspect of the prosthetic device could, itself, be biodegradable. Thus, a resorbable external skeletal structure combined with a resorbable internal drug eluting collagen layer, the two layers having the same or different rate of degradability and resorption, would generate a healed vascular or graft structure without the necessity of foreign material remaining after the procedure. One skilled in the art would understand in view of this disclosure that numerous other such materials are likely to be usable in this invention. For example, Dacron® polyester can also be a suitable material for the external support structure.

A further object of the present invention is device self-fixation to the outer surface of the vascular wall. The device could be made more adhesive to the vascular wall if in the final stage collagen is combined with photoreactive groups such as FITS (fluorescein isothiocyanate) or Bengal Rose both from Sigma Chemicals, St Louis, Mo., USA. Stimulation of the device with ultra violet light activates the photoreactive groups and will increase adhesion. Fibrin sealant and acetylated collagen have been found to increase adhesion of collagen matrix material to the outside vascular wall.

Another embodiment of the present invention is a method of inhibiting stenosis of hemodialysis access graft comprising the method of placing the prosthetic device (described above) over a graft or vascular structure and/or at the site of anastomosis and anchoring the prosthetic device at the desired site (e.g., by suturing).

Figure 1B:
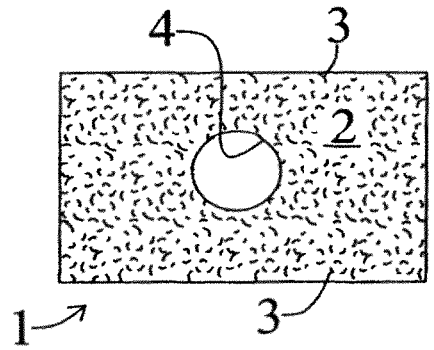

FIGS. 1A, 1B, 2A, and 2B illustrate preferred embodiments of the present invention 1. In FIG. 1A there is shown a rectangular sheet of a matrix material 2 having disbursed or distributed therein an agent 3 of the present invention (shown by stippling). FIG. 1B illustrates a further embodiment of the invention shown in FIG. 1A in which a hole 4 has been created in the drug-containing matrix material 3, 2. It will be understood by one skilled in the art that the diameter of hole 4 will be adjusted to accommodate the outside diameter of any vascular or graft structure passing therethrough. In one embodiment, the diameter of hole 4 is 6 millimeters.

Figure 2A:
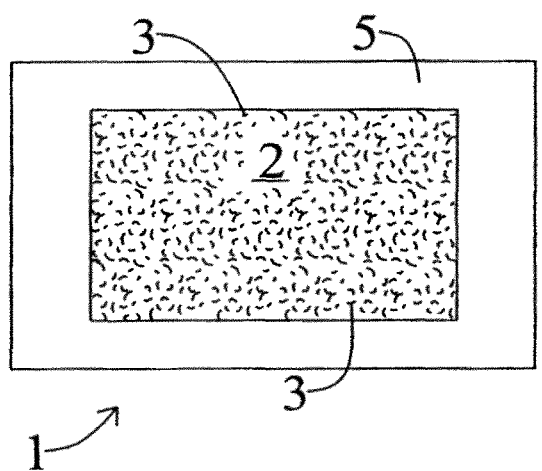
Figure 2B:
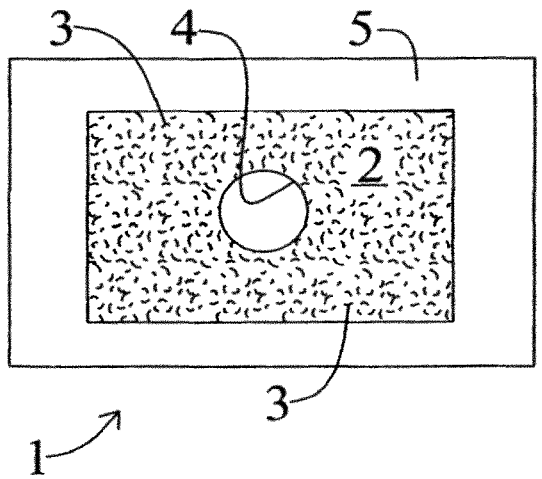

FIGS. 2A and 2B illustrate a further embodiment to the present invention in which an exterior support or skeletal structure or means 5 is employed. Support 5 is exterior to matrix material sheet 2 when sheet 2 is rolled or coiled into a cylindrical shape. Exterior skeletal means such as polytetrafluoro ethylene (PTFE) and dacron sheets are among the support materials presently contemplated. Many other such exterior skeletal support means will occur to one skilled in this art. As is shown, FIG. 2B illustrates an embodiment to the invention in which a hole 4 (which may vary in diameter) is employed.

Figure 3A:
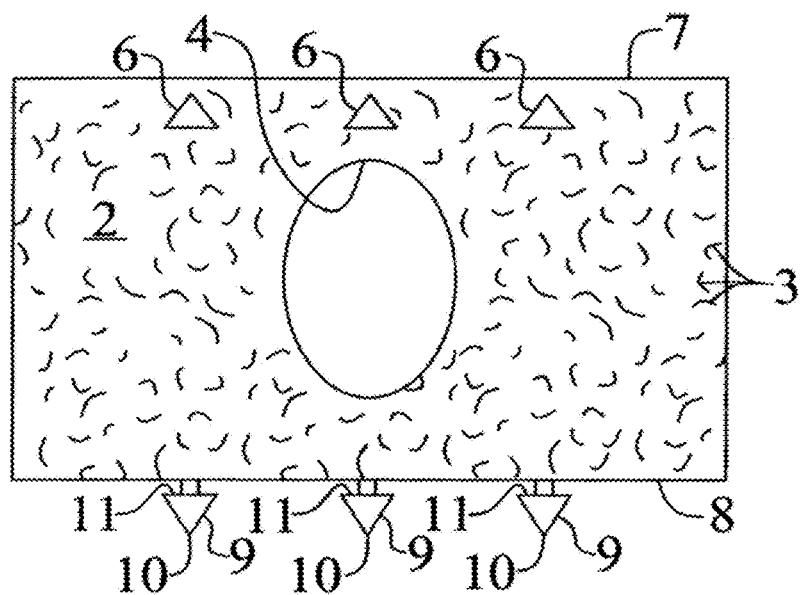
FIGS. 3A-3C illustrate a self-interlocking embodiment of this invention.
Figure 3B:
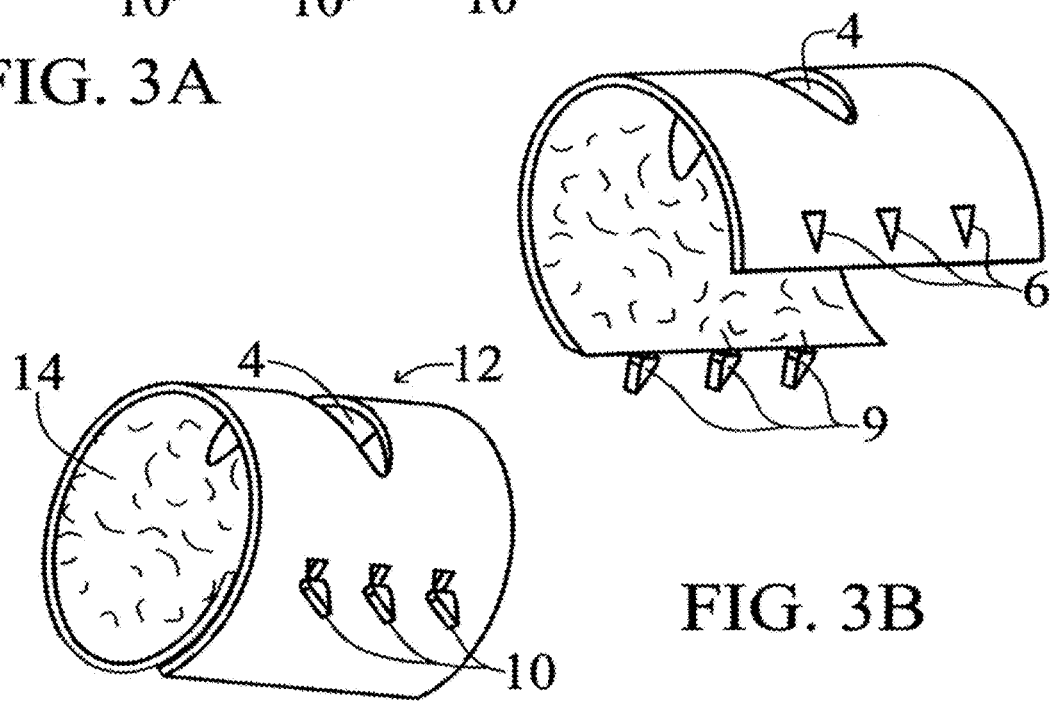
Figure 3C:

FIGS. 3A, 3B, and 3C illustrate an embodiment of the invention employing an interlocking design in which one edge of the rectangular agent-eluting sheet or matrix material interlocks adjacent the opposite edge. More specifically, FIG. 3A shows a rectangular matrix material 2 having agent 3 (shown in stippling) disposed or disbursed therein. Also shown on the sheet illustrated in FIG. 3A are a series of v-shaped notches 6 located approximately adjacent one edge 7 of the agent-containing matrix material. Cooperating with notches 6 on the opposite edge 8 are a series of projections 9. Projections 9 are arrow-head shaped. However, other combinations of projection 9 and slots 6 certainly are contemplated by this invention. Thus, assembly of a sleeve embodiment of the present invention involves rolling edge 8 toward edge 7 (shown in FIG. 3B) and inserting projections 9 into slots 6. As is shown in FIG. 3C projections 9 have been inserted into slots 6 from the inside of the tubular structure meaning that the points 10 of projections 9 project from the inside to the outside of the structure. As is shown, the following edges 11 of projections 9 cooperate with v-shaped slots 6 to lock the flat structure into a cylindrical vascular-dimensioned sleeve 12. Vascular sleeve 12 further then defines a lumen 14. Lumen 14 is of a vascular dimension such that the interior surface of sleeve 12 would be in contact with the exterior surface of a vascular structure to which sleeve 12 was attached. In this fashion, the drug or agent-eluting, vascular-dimension sleeve is deployed over and around the vascular structure with which this invention is to be used.

Figure 4A:
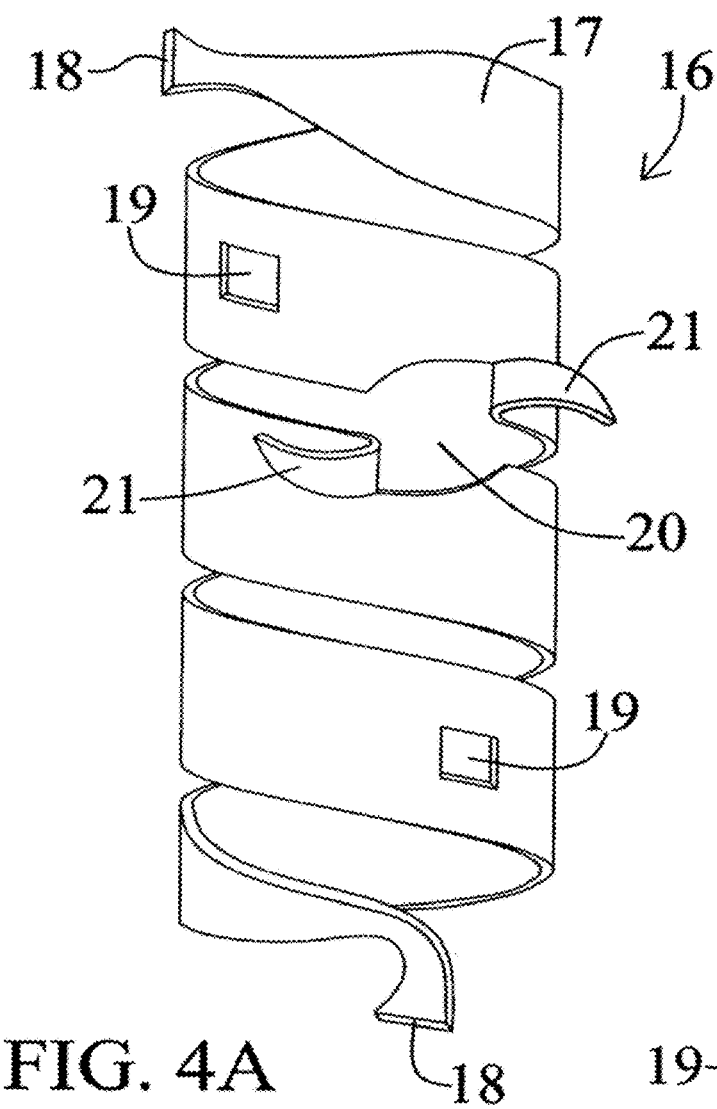
FIGS. 4A and 4B illustrate a second interlocking embodiment of the present invention.
Figure 4B:
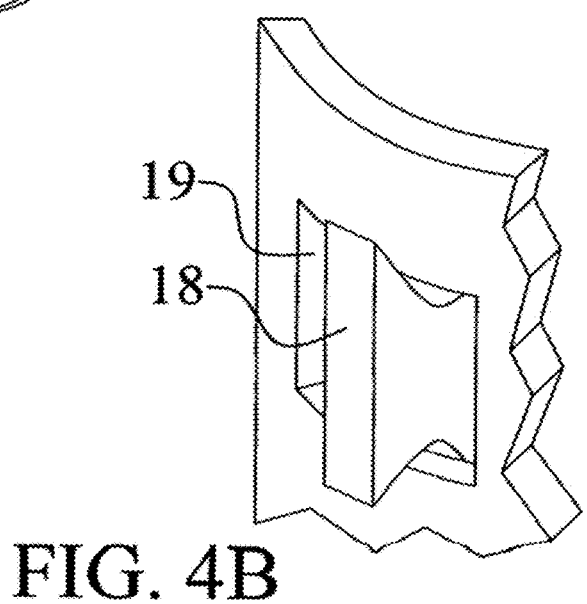

FIGS. 4A and 4B illustrate a second interlocking embodiment of the present invention. In embodiment, a strip-form of the present invention is utilized. Agent-eluting sleeve 16 comprises an elongate drug or agent-eluting matrix material 17 (alone or in conjunction with an external support means, not shown). Created in matrix material 17 are two locks 18 located on opposite ends thereof. Cooperating with lock 18 are windows 19 into which locks 18 are inserted such that sleeve 16 is deployed against and on the exterior of the operant vascular structure. As is shown on FIG. 4B, lock 18 may be inserted into window 19 from the inside toward the outside. In an alternative embodiment lock 18 may be inserted into window 19, from the outside toward the interior of the sleeve structure. Also shown in FIG. 4A is a representative shunt opening 20 including two shunt contact wings or flaps 21.

Figure 5:
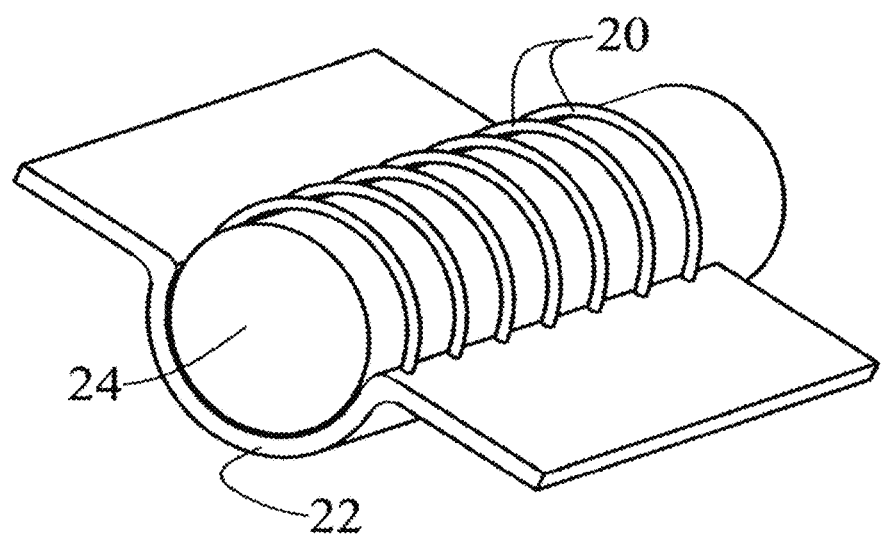
FIG. 5 Shows the basic device shown in FIGS. 1A-1B/2A-2B include an exterior wire support or framework, which assists retention of sleeve shape.
Figure 10:
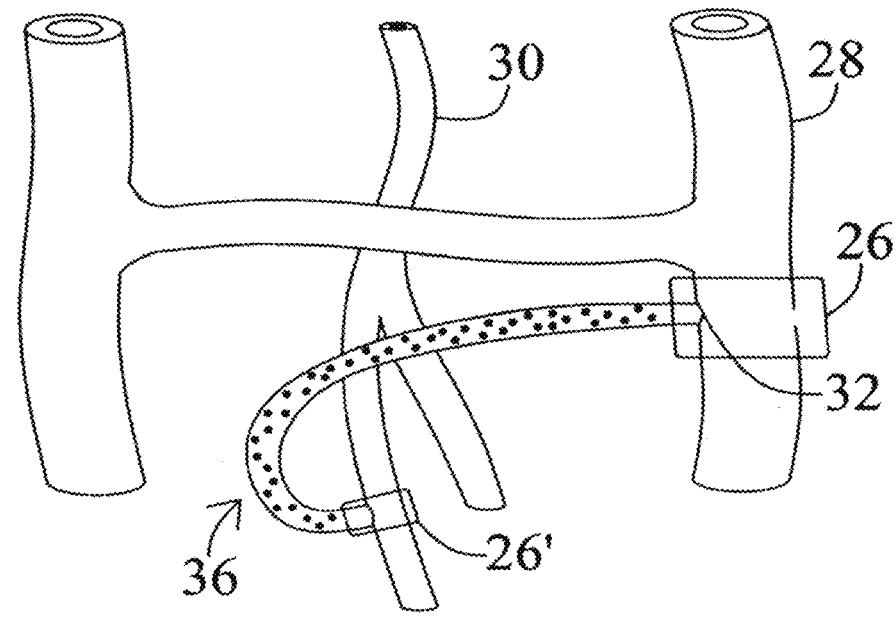
Figure 11:
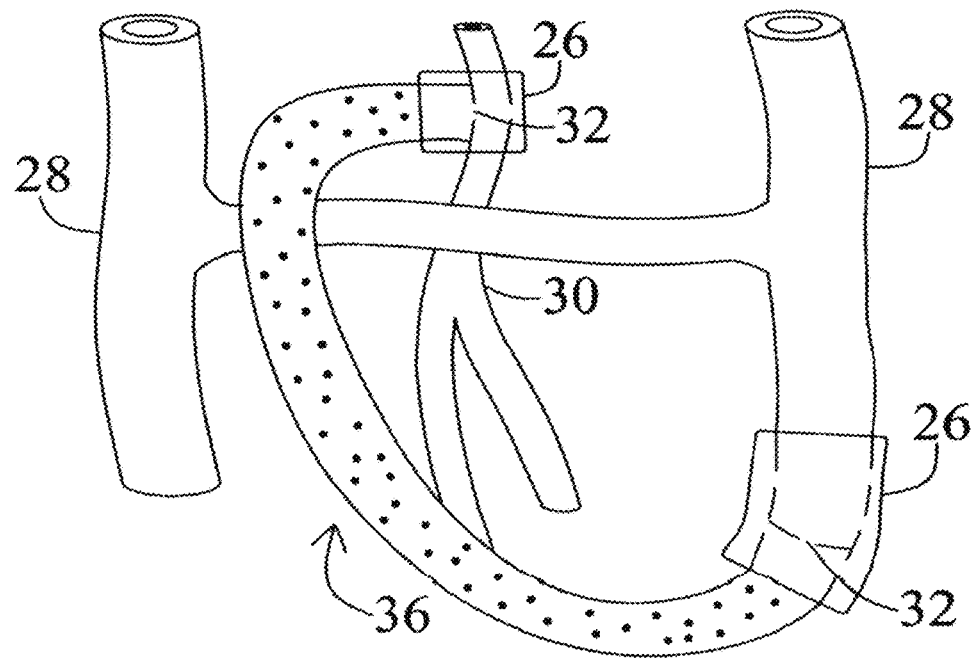

FIG. 5 illustrates another embodiment to the present invention in which an external wire support or framework means is employed. External wire framework 20 surrounds a preferred embodiment of the present invention i.e. a PTFE and drug-coated collagen matrix material 22 disposed around vessel 24.

FIGS. 6-13 illustrate various arterio-venous fistuale. A drug eluting sleeve or matrix material of the present invention 26 is shown to be implanted, wrapped or placed around the various fistulae 32 shown in the several figures. In each of these figures venous structures are designated 28 and arterial structures are designated 30. Arrows 34 illustrate the direction of blood flow.

FIGS. 10-13 illustrate a further embodiment of this invention in which a graft e.g., a PTFE graft, 36 is used in conjunction with the present invention. As is shown in FIG. 13, graft 36 may itself include a matrix material with a drug or agent 36 (shown in stippling) of this invention.

A further application of the present sleeve involves utilization of the interior drug-imbibing protein layer as a drug source or drug reservoir. In that application the drug selected may be replenished periodically, e.g., by puncturing the sleeve with a needle and delivering additional drug thereto or creating a reservoir for the drug within the sleeve from which it can be gradually eluted.

EXAMPLES

The following examples are set forth to illustrate the device and the method of preparing matrices for delivering antiproliferative drug(s) and other therapeutics. The examples are set forth for purpose of illustration and not intended in a limiting sense.

Example 1: Inhibitory Effect of Different Antiproliferative Agents

Prefabricated collagen matrices were placed in different antiproliferative drug solutions until complete saturation occurred. The antiproliferative drugs were chosen to represent the more active compounds capable of smooth muscle cell and fibroblast inhibition without inhibiting collagenase and elastase enzymes. (Collagenase and elastase enzymatically inhibit collagen accumulation—one cause of restenosis). The collagen matrices were saturated with these compounds at concentration of 25 µg/ml lyophilized, washed with 0.066 M phosphate buffer (pH 7.4) at 37° C. for 24 hours and cut in the shape of a disc with density of compound about 5 µg per cm$^2$. After washing, sterile discs, 15 mm in diameter were placed in 24-well culture plate and cells at a density of 5000 per cm$^2$ were seeded. Five days later cell number was measured and enzymatic activity was evaluated in the aliquots of media via chromogenic substrates hydrolysis and spectrophotometry. These data are presented in Table 1.

TABLE 1

Inhibitory effect of different antiproliferative agents

| Agent | SMC Inhibition % | Fibroblast Inhibition % | Collagenase Activity % | Elastase Activity % |
|---|---|---|---|---|
| Control, plain matrix | 0 | 0 | 100 | 100 |
| Paclitaxel | 88 ± 6 | 62 ± 11 | 98 ± 5 | 90 ± 4 |
| Rapamycin | 94 ± 5 | 90 ± 12 | 137 ± 8 | 142 ± 5 |
| Cyclosporin A | 61 ± 7 | 53 ± 7 | 104 ± 5 | 87 ± 7 |
| Tetracycline free base | 11 ± 8 | 13 ± 5 | 56 ± 8 | 81 ± 4 |
| Methotrexate | 32 ± 9 | 28 ± 6 | 23 ± 12 | 14 ± 3 |
| Actinomycin D | 44 ± 11 | 35 ± 8 | 55 ± 9 | 84 ± 11 |

In this comparative in vitro test, among tested agents, Paclitaxel and Rapamycin performed similarly.

Example 2: Capacity of Different Types of Matrices to Bind Rapamycin

In the next in vitro study, the ability of different matrices to bind Rapamycin was tested. A prefabricated (BioMend, Sulzer Calcitek, Inc or Biopatch, Ethicon Inc, containing collagen-alginate) collagen matrix with Rapamycin was prepared as described in Example 1 at initial Rapamycin concentration of 250 µg/ml. Prefabricated chitosan (using technique described in: Almin, C., Chunlin, H., Juliang, B. et al "Antibiotic loaded chitosan bar. In vitro, in vivo study of a possible treatment for osteomyelitis," Clin Orthop pp. 239247 (September 1999) and fibrin matrices (using technique mentioned in example 5) were also placed in of 250 µg/ml of rapamycin in DMSO solution until complete saturation occurred. After solvent evaporation, the matrices combined with drugs were washed with 0.066 M phosphate buffer (pH 7.4) at 3° C. for 24 hours.

To compare matrix capacity, fluorescent Rapamycin derivate loaded onto 1.88 cm$^2$ matrix surface of the same thickness was used. After incubation with 0.14 M NaCl solution, the residual rapamycin was extracted with dimethylsulfoxide (DMSO) and yield was measured using fluorescence spectroscopy. These data are presented in Table 2.

TABLE 2

Matrix Capacity for Rapamycin

| Matrix | Rapamycin capacity (µg per cm$^2$) |
|---|---|
| Collagen | 124.5 ± 14.3 |
| Collagen-alginate | 131.1 ± 12.3 |
| Chitosan | 78.7 ± 8.9 |
| Fibrin | 145.8 ± 12.7 |

As expected, capacity of protein matrices was found to be higher than the chitosan matrix, usefulness of fibrin or collagen as therapeutic matrix for antiproliferative drug delivery may depend on particular combination or additional components or requirements of longevity of the matrix.

Example 3: Delivery Systems Using Liposomes

Liposomes represent a form of drug delivery system, and offer controlled release of biologically active agents. They are used in pharmaceutical formulations especially for water insoluble drugs. Rapamycin is a typical example. Liposomal entrapment has been shown to have considerable effect on the pharmacokinetics and tissue distribution of administered drugs. The formulations tested included nonionic liposomal formulation composed of glyceryl dilaureate (Sigma Chemicals, St Louis, Mo.), cholesterol (Sigma Chemicals, St. Louis, Mo.), and polyoxylene-10-stearyl (Sigma Chemicals, St. Louis, Mo.) either at a weight ratio of 56:12:32 (Formulation 1) or nonionic 40% hydroalcoholic oil-in-water liposomal emulsion containing isopropyl myristate (Sigma Chemicals, St. Louis, Mo.) and mineral oil (Sigma Chemicals, St. Louis, Mo.) (Formulation 2). Rapamycin was entrapped into each formulation at a concentration of 250 µg/ml in dimethylsulfoxide or isopropanol and formed liposomes were applied on surface of prefabricated collagen sheets to create maximal surface density of Rapamycin. Samples were washed with 0.066 M phosphate buffer (pH 7.4) at 37° C. for 24 hours. To compare matrix capacity, liposomes loaded with fluorescent Rapamycin derivate placed onto 1.88 $cm^2$ disc was used. After incubation with 0.14 M NaCl solution, matrices with remaining Rapamycin were extracted with dimethylsulfoxide (DMSO) and fluorescent yield was measured.

TABLE 3

Liposomal Delivery System

| Liposome Type | Rapamycin Binding Capacity µg per $cm^2$ |
|---|---|
| Nonionic cholesterol liposomes (Formulation1) | 117.4 ± 10.9 |
| Nonionic oil-in-water emulsion (Formulation 2) | 89.6 ± 7.5 |
| Saturated collagen matrix (DMSO) | 124.5 ± 14.3 |
| Saturated collagen matrix (isopropanol) | 105.6 ± 9.7 |

Liposomal delivery systems do not have significant advantages over saturated collagen matrix in ability to bind Rapamycin. However the liposomal approach may be useful for other antiproliferative drugs.

Example 4: Preparation of a Laminated Collagen Film

In order to prepare a textured, surface neutralized, laminated collagen film an isotonic suspension of insoluble fibrillar collagen was obtained. Three liters of chilled collagen suspension at concentration of 5 to 18%, (preferred 12%) was swollen overnight in 0.3-0.6 M acetic acid, (preferred 0.52 M), at 4° C. The swollen suspension was dispersed with 3 liters of crushed ice for 10-20 min, (preferred 12 min.) in a blender and thereafter homogenized for 30 min in an Ultra-Turrax (Alfa, Sweden). The resulting slurry was filtered through a series of filters (Cellector, Bellco, UK) with pore sizes decreasing from 250 µm to 20 µm, mounted in filter holder (Millipore). After degasation at 0.04-0.09 mbar, preferred 0.06 mbar, the slurry was mixed with 2 liters of chilled 0.1-0.05 M NaOH, final pH adjusted to 7.4±0.3. The neutralized suspension can be stored at 4-6° C. only for several hours prior to matrix formation. This neutralized suspension serves as a foundation for preparation of a saturated or dispersed form of a matrix containing rapamycin. The neutralized slurry may be directly cast as a wet film with a thickness of 3 mm on a flat hydrophobic surface at room temperature. A dry film with a thickness of approximately 60-70 µm is formed. Three to five ml of slurry cover an area of 10 $cm^2$ area. On top of such a surface several layers may be formed. The layers will serve as a basis for preparation of saturated form of anti proliferative agent by immersing the collagen film into solutions of rapamycin, Taxol or combinations thereof. Simultaneous combination of neutralized slurry and rapamycin or other agents in suspension may be used for preparation of film with dispersed form of active ingredients.

An important factor in the preparation of the matrix material is the porosity of the protein carrier from which the device is to be formed. Porosity may be regulated by drying rate, temperature, and the characteristics of the initial collagen. Porosity is significant because it controls the kinetics of drug release. It is desirable for the matrix to be sufficiently porous to bind small molecules such as rapamycin (Molecular weight 914.2) and durable enough to maintain the shape of device. Samples of collagen matrix with effective pore size of 0.002 to 0.1 microns were tested. Higher binding capacity (to bind rapamycin in saturation experiments) was observed with the matrix having pore size of 0.004 microns. In addition, collagen matrices with bigger pore sizes are fragile. Since the binding capacity of the matrix to the antiproliferative agent is critical for this application, three different concentrations of rapamycin were used to prepare a rapamycin-collagen matrix combination from commercially available collagen prepared at optimal density of pores. The three different concentrations labeled high, medium and low, were 120±5 µg/$cm^2$, 60±4 µg/$cm^2$, and 30±3 µg/$cm^2$, respectively. None of these matrices were fragile or had non-uniform rapamycin distribution. Different densities permit regulating kinetics of drug release.

Example 5: Preparation of an Implantable Fibrin Matrix Device Combined with an Antiproliferative Agent In general, to make a device based on a fibrin matrix loaded with an antiproliferative agent, aqueous fibrinogen and thrombin solutions are prepared as described below. Commercial fibrinogen can be acquired from such vendors as Sigma, American Red Cross, or can be prepared from plasma by well-known techniques. Alternatively, fibrinogen prepared by recombinant methods is suitable for use. Commercial active thrombin can be acquired from Sigma or from Johnson and Johnson as thrombin, topical USP, Thrombogen. To make the fibrinogen and thrombin solutions used to prepare the matrix, the necessary components are measured, weighed and dissolved in about 900 ml of deionized water. Tables 4 and 5 disclose preferable compositions used to prepare fibrinogen and thrombin solutions to prefabricate matrix, respectively.

The glycerol in Table 4 used as a plasticizer. Other plasticizers would also be suitable for the present invention. TRIS buffer is used for pH adjustment. Suitable alternatives for TRIS include HEPES, Tricine and other buffers with a pKa between 6.8 and 8.3. Triton X-100 is a non-ionic detergent and stabilizer and may be substituted by other detergents and stabilizers. Caprylic acid may be substituted by other agents that provide protection from denaturation, for example, alginic acid.

TABLE 4

Fibrinogen Solution Composition

| Component | Composition Range g/liter | Composition Preferred g/liter |
|---|---|---|
| Fibrinogen | 50-120 | 76 |
| Glycerol | 20-80 | 40.5 |

TABLE 4-continued

Fibrinogen Solution Composition

| Component | Composition Range g/liter | Composition Preferred g/liter |
|---|---|---|
| TRIS buffer | 3-25 | 12.1 |
| Caprylic Acid | 10-35 | 18.7 |
| Triton X-100 | 2-8 | 5.4 |
| Heparin | 0.5-6 | 2.38 |

TABLE 5

Thrombin composition

| Component | Composition range (g/liter) | Composition preferred (g/liter) |
|---|---|---|
| Thrombin | 5,000-100,000 units | 8,000 units |
| Albumin | 1-100 | 50 |
| Factor XIII | 1,000-5,000 units | 2,500 units |
| CaCl2 | 50-250 mg/liter | 123 mg/liter |
| Troglitazone | 3-24 | 8 |

Fibrinogen converted to fibrin is the most critical reagent in the matrix because it controls the material properties of the matrix, such as flexibility, pore size and fiber mass density. These features determine how easily other molecules can diffuse within the matrix and how long the matrix may remain intact before it is resorbed.

In Table 5, albumin is a stabilizer of thrombin. Thrombin controls the rate of fibrin matrix formation. The presence of Factor XIII is preferred but not necessary. Factor XIII covalently cross-links fibrin, making the matrix more stable. Calcium ions are needed for activation of thrombin. Troglitozone (Sankyo, Japan) is a thiazollidione derivate, which decreases collagen accumulation in the vascular wall. (Yao L, Mizushige K, Murakami K et al. Troglitozone decreases collagen accumulation in prediabetic stage of a type II diabetic rat model. Heart 2000: 84: 209-210

It is preferable to completely dissolve each component before adding the next component. If necessary, after the last component is dissolved, the pH is adjusted to 7.0-7.4 and the solution volume is adjusted to 1 liter with water. The solutions are then degassed. Both solutions are dispensed by pump through mixture chamber onto a non-stick, preferably hydrophobic, surface to form a film approximately 2 mm thick. The film is then dried for about 3 to 6 hours at temperature in the range of about 20° C. to 60° C., at a pressure of about 30 Torr. Residual moisture of the film is about 10%, preferably less than 3%, of the total wet weight.

On this surface dry solid Rapamycin is added to create density in the range of 100 to 500 μg per cm² of film. A second layer of fibrin matrix is formed on top of this surface such that the drug is sandwiched between the two layers of fibrin.

In one embodiment of the present invention, one would add (and/or) an antiproliferative/anti restenotic agent like Rapamycin or Taxol, an anti rejection drug like Rapamycin or tacrolimus, an anti-inflammatory drug and/or an antisense oligonucleotide to enhance antirestenotic effects. These solid materials would be added to supplement the fibrin-Rapamycin sandwich complex described above.

Example 6: Method of Cross Linking Chitosan Matrix

In order to increase binding capacity of a chitosan matrix for antiproliferative drug, cross-linking of fiber is used. Fifty ml of chilled chitosan suspension at concentration from 10% to 25%, (preferred 12%) was gently and slowly mixed with 5 to 25 ml of acrylic acid chloranhydride for 30 min. to acetylate this polymer. After this time period, a solution of rapamycin in DMSO at concentration of 250 μg/ml was added, mixed vigorously, and poured onto the chitosan matrix surface for spontaneous cross-linking and formation of conjugated rapamycin. This approach, because of the microporous structure of the chitozan, allows increasing the binding capacity of the matrix from 15% to 45%.

Example 7: Incorporation of Rapamycin into Collagen Matrix by Dispersion, Immobilization and Immobilization-Dispersion Besides the technique of saturation, rapamycin was incorporated into the collagen matrix by three different methods: dispersion, immobilization, and immobilization-dispersion.

Dispersion technique: an aqueous slurry of water insoluble collagen was prepared using non-crosslinked dry, highly purified, lyophilized calfskin collagen obtained from Elastin Product Co., Inc. (Owensville, Mo.). This collagen and solubilizing buffer are chilled to a temperature of 2-8° C., preferred 4° C. and vigorously mixed to prepare collagen slurry containing 10-21%, (preferred 12%) of collagen protein. Such slurry includes 9% of plasticizer, glycerol 15% o rapamycin in DMSO at concentration of 250 μg/ml and water. The solution had a viscosity of 50,000 cps. Immediately after mixing with rapamycin, 8% glutaraldehyde is added to the slurry (100-350 ml per liter of slurry). The aqueous slurry must be homogenous and degassed, the pH is adjusted to 6.0-7.1. The solution is constantly vigorously mixed and dispersed by pump onto a non-stick surface to form a film approximately 2 mm thick. All procedures are carried out at a temperature of 4° C. The film is then dried for about 3-7 hours at temperatures in the vicinity of 45° C., and a pressure of 15 Torr until its residual moisture is less than about 10% of the total weight. The drug solution application and drying steps are repeated three more times.

II): Immobilization technique: The same collagen preparation from Elastin Product Co. is used. One volume of 12% collagen slurry is chilled and coupled with rapamycin via esterification of antiproliferative drug. Esterification is carried out with 0.9 M N-hydroxysuccynimide (Pierce Biochemical, Rockford, Ill.) in the presence of 0.9 M N-dicyclohexylocarbodimide (Pierce Biochemical, Rockford, Ill.) at 2-4° C. for 2 days. Conjugates are prepared by titration of active N-hydroxysuccynimide ester of rapamycin in DMSO under the surface of stirred collagen suspension, the pH of the reaction is maintained between 7.0 and 8.5, preferred 7.8. After drying, the films with conjugated rapamycin are washed with 0.15 M NaCl containing 0.02 M sodium bicarbonate at a pH of 7.4. HPLC reveals no free rapamycin in the matrix. Rapamycin ester reacts with amino- or hydroxyl-groups of aminoacid residues forming a covalent linkage with collagen. After such immobilization, Rapamycin is released as a result of in vivo or in vitro degradation-erosion of the matrix. Nakano et al make reference to collagen (SM-10500) degradation and resorption via natural metabolic process in Rhesus monkeys during 6 months Ref: Nakano M, Nakayama Y, Kohda A et al: Acute subcutaneous toxicity of SM-10500 in rats. Kisoto Rinsho (Clinical Report) 1995; 29: 1675-1699]

In order to study the rate of rapamycin release from the matrix, samples are washed with 0.066 M phosphate buffer (pH 7.4) at 37° C. for 24 hours and cut to give a shape of disc with area of 1.88 cm², and placed into 24 well culture plate containing 0.14 M NaCl, 0.05M Tris buffer, 0.5% of albumin, and 0.1 mg/ml collagenase, at pH 7.0. Collagenase is added to increase erosion of collagen matrix and facilitate release of rapamycin. Aliquots are collected at various time intervals from the wells.

A combination of dispersed and conjugated forms is also prepared. In all these forms, the content of rapamycin is 5.0 µg per cm$^2$. The samples are placed in wells and 1 ml of elution media containing serum are added. Aliquots are taken every hour.

Figure 14:
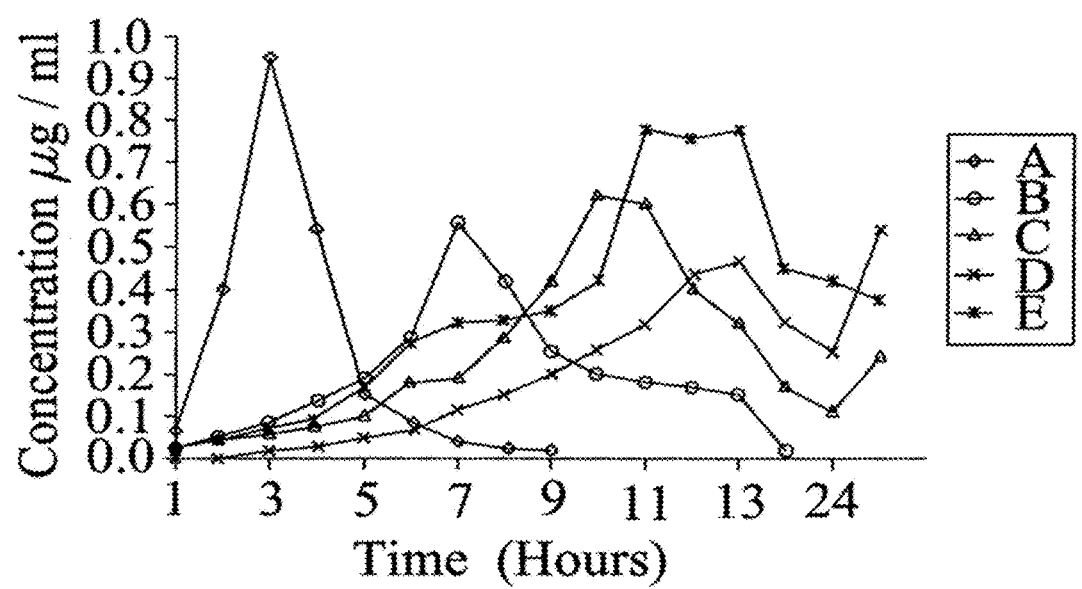
FIG. 14 Shows rates of release of collagen saturated with tetracycline and rapamycin. Rapamycin was combined with a collagen matrix material using four different formats. Numbers on y-axis shows concentration of drug in micrograms per ml. Legend: A=Collagen saturated with Tetracycline. B=Collagen Saturated with Rapamycin. C=Rapamycin Dispersed throughout collagen. D=Collagen conjugated with Rapamycin. E=Combination of dispersed and conjugated forms of Rapamycin.

The content of Rapamycin is measured according to the procedure of Ferron et al. (Ferron G M, Conway W D, and Jusko W J. Lipophilic benzamide and anilide derivatives as high-performance liquid chromatography internal standard: application to sirolimus (rapamycin) determination. J Chromatogr B Biomed Sci Appl 1997; December 703: 243-251.) These measurements are made using batch assay and, therefore, represent release rates at 0 ml/min flow rate. The results are tabulated in Table 6 and graphically illustrated in FIG. 14; concentrations of antiproliferative drug are in µg/ml.

These data show that different forms of drug imbedding and drugs with different solubility have distinct kinetics. In the case of comparatively soluble Tetracycline, after saturation of the collagen matrix with the free base, peak release occurs in a short period of time, whereas for less soluble rapamycin this peak is postponed for several hours. It has been shown in experiments in vitro, that collagen saturated with soluble antibiotics such as gentamicin, cefotaxin, tetracycline or clindamycin delivers these antibiotics at effective concentrations for 4 days. [Wachol-Drewek Z, Pfeifer M, Scholl E. "Comparative investigation of drug delivery of collagen implants saturated in antibiotic solutions and sponge containing gentamicin." (Biomaterials 1996; 17: 1733-1738)].

In other laboratories is also was shown in vivo, that, collagen saturated with gentamycin at concentration of 3 µg/g and implanted into muscle tissue is capable of delivering antibiotic into blood through day 28. However, concentration was less than optimal. (Mehta S, Humphrey J S, Schenkman D I, et al., "Gentamycin distribution from a collagen carver." J Orthop. Res., 1996; 14: 749-754.). It is theorized that knowing the low concentration of collagenase in perivascular space and the low flow of perivascular fluid (only a few milliliters per day) a matrix material, saturated with rapamycin might produce in vivo delivery kinetics, which will support effective local concentration of antiproliferative drug for a period of several weeks to prevent and combat progress of SMC proliferation. Inhibitory concentrations for SMC would be in the range of 0.001 to 0.005 µg/ml culture media. Such levels are met or exceeded in vitro for 3 weeks. Moreover, Rapamycin dispersed into collagen matrix may exhibit an antiproliferative effect for a month or longer. Finally, conjugated and combined forms may support treatment until complete matrix erosion.

Example 8: Biological Activity of Rapamycin in the Rapamycin-Collagen Matrix

Figure 15:
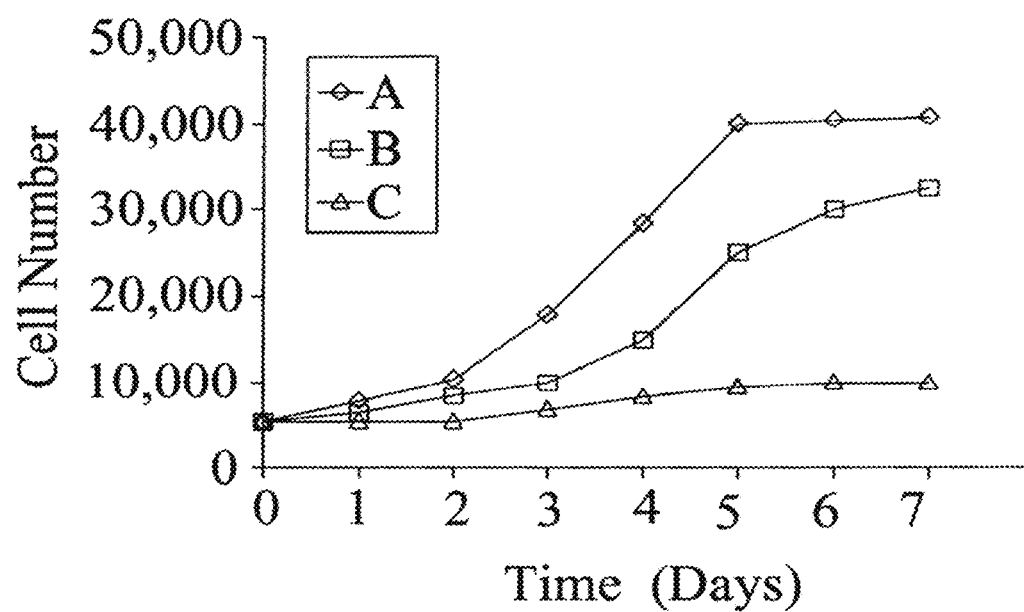
FIG. 15: Is a comparison of inhibition of growth of Smooth Muscle Cells using collagen matrices combined with different anti-proliferative agents. Numbers on y-axis denotes cell numbers. Legend: A=Control; B=Collagen+Actinomycin D; and C=Collagen+Rapamycin.

The most important parameter when assessing the combination of rapamycin and collagen is inhibition of smooth muscle cell (SMC) growth. To evaluate this parameter SMC's at density of 5,000 cells per cm$^2$ are seeded onto control tissue culture surface and testing matrices (Table 7). Cell growth curves are presented in FIG. 15.

Actinomycin D is quickly released from the drug matrix and suppresses cell growth for only a short period of time. A change of media removes soluble Actinomycin and after several washes no antibiotic is present in the media or in the matrix. As a result, cells start proliferating as usual. Because of a slow gradual release of rapamycin suppression of cell growth continued throughout the observation period.

TABLE 6

Rate of release of collagen saturated with Tetracycline and Rapamycin. Rapamycin was combined with collagen matrix using four different methods.

| Time (Hour) | Collagen Saturated With Tetracycline | Collagen Saturated With Rapamycin | Rapamycin Dispersed Throughout Collagen | Collagen Conjugated With Rapamycin | Combination of Dispersed and Conjugated Forms |
|---|---|---|---|---|---|
| 1 | 0.06 | 0.01 | 0.01 | 0 | 0.01 |
| 2 | 0.4 | 0.05 | 0.03 | 0 | 0.02 |
| 3 | 0.96 | 0.09 | 0.06 | 0.01 | 0.07 |
| 4 | 0.54 | 0.15 | 0.08 | 0.02 | 0.09 |
| 5 | 0.15 | 0.19 | 0.12 | 0.05 | 0.17 |
| 6 | 0.08 | 0.28 | 0.18 | 0.07 | 0.26 |
| 7 | 0.02 | 0.57 | 0.19 | 0.11 | 0.31 |
| 8 | 0.01 | 0.44 | 0.29 | 0.13 | 0.32 |
| 9 | 0.01 | 0.24 | 0.41 | 0.19 | 0.34 |
| 10 | — | 0.20 | 0.62 | 0.27 | 0.41 |
| 11 | — | 0.19 | 0.61 | 0.31 | 0.78 |
| 12 | — | 0.18 | 0.40 | 0.42 | 0.76 |
| 13 | — | 0.15 | 0.32 | 0.45 | 0.79 |
| 14 | — | 0.02 | 0.16 | 0.32 | 0.45 |
| 24 | — | — | 0.11 | 0.24 | 0.42 |
| Totally Dissolved matrix | 0 | 0.003 | 0.23 | 0.53 | 0.39 |

Cell Number

TABLE 7

Comparison of inhibition of growth of smooth muscle cells using collagen matrices saturated with Actinomycin D and Rapamycin

| Days in Culture | Control | Collagen + Axtinomycin D | Collagen + Rapamycin |
|---|---|---|---|
| 0 | 5000 | 5000 | 5000 |
| 1 | 6430 ± 20.4 | 5230 ± 16.8 | 4800 ± 9 |
| 2 | 10240 ± 27.1 | 7350 ± 19.5 | 5040 ± 11.2 |
| 3 | 16340 ± 30.12 | 9400 ± 13.2 | 6230 ± 13.4 |
| 4 | 27100 ± 25.4 | 14280 ± 17.6 | 7400 ± 15.1 |
| 5 | 38450 ± 22.6 | 23540 ± 17.8 | 8000 ± 17.8 |
| 6 | 40000 ± 20.7 | 29300 ± 19.4 | 8550 ± 13.9 |
| 7 | 40100 ± 20.5 | 32090 ± 32.1 | 8500 ± 14.4 |

Example 9

Two different types of matrices, collagen and fibrin combined with antiproliferative agents (singly or in combination) along with Vitamin K are added to the cell culture medium in different ratios. Cells are seeded at the same density, on day 5 numbers of viable cells are measured by Alamar blue assay. Data are presented in Table 8.

TABLE 8

Inhibition of cell growth (%)

| Matrix to Media Ratio | Collagen plus Rapamycin | Collagen Plus Rapamycin Plus Taxol | Collagen plus Rapamycin plus Vitamin K | Fibrin plus Rapamycin | Fibrin plus Rapamycin plus Taxol |
|---|---|---|---|---|---|
| 1:400 | 5 | 4 | 8 | 3 | 2 |
| 1:200 | 25 | 27 | 34 | 21 | 19 |
| 1:100 | 54 | 50 | 77 | 56 | 55 |
| 1:50 | 73 | 76 | 99 | 79 | 78 |
| 1:25 | 88 | 88 | 99 | 79 | 84 |
| 1:12.5 | 95 | 99 | 99 | 98 | 96 |
| 1:6.25 | 95 | 99 | 99 | 100 | 98 |

Example 10: Antiproliferative Effect of Combination of Rapamycin and Heparin Combined to a Collagen Matrix Antiproliferative effects of different components combined within a matrix may exhibit a synergy. A combination of dispersed Rapamycin, soluble and immobilized heparin are used. In order to immobilize heparin 5 ml of chilled heparin solution at concentration of 1 mg/ml to 10 mg/ml, (preferred 5 mg/ml) is mixed with 5 to 20 ml, (preferred 11.4 ml) of acrylic acid chloranhydride at the rate of approximately 1 µl per min, (preferred 2.5 µg per min). After addition, mixture is agitated for 30 minutes at a temperature of 4-8° C. The heparinized collagen is extensively washed with sodium phosphate buffered saline at pH 7.4. A colorimetric assay with Eosin A is used to determine the concentration of heparin immobilized on matrix. Using this method between 0.01 mg/cm² and 0.1 mg/cm² may be covalently linked to the matrix.

Such a formulation combined with Rapamycin has inhibitory effect on SMC growth in culture if added in the form of suspension into the media at ratio 1:100, whereas individual forms have lesser effects; ratio of 1:25 for heparin alone to 1:65 for dispersed rapamycin. Each of these drugs can inhibit restenosis via different mechanisms, hence it is reasonable to expect synergistic effect when used in combination. Heparin can also be used in matrix saturated form in combination with antiproliferatives.

Example 11

Sustained local delivery of Dexamethasone in combination with Rapamycin (or other antiproliferative agents) can be used to simultaneously inhibit restenosis as well as inflammatory reactions. Twenty percent (weight/weight) collagen slurry is prepared, to which is added a 2% (weight/weight) suspension of dexamethasone. This mixture is sprayed on to a plastic surface to form the film. The final thickness of the film ranged from 1.92 to 2.14 mm (mean 2 mm). This sheet is flexible and mechanically stable. The kinetics of dexamethasone elution from the c matrix (collagen plus rapamycin) were characterized in an in vitro system. Fifteen mm diameter sheets were placed in the wells and immersed in 2.5 ml of phosphate buffered solution. At time points ranging from 1 to seven days, concentration of dexamethasone in aliquots of elution buffer were measured by spectrophotometry. Chemical stability of the dexamethasone through the sheet formation, drying storage and elution process was confirmed by HPLC. Cumulative in vitro elution of dexamethasone is shown in Table 9.

More than 50% of the dexamethasone elution occurred within the first three days, with a leveling off of the elution curves after 6 days. Dexamethasone can prevent a severe inflammatory response, which is maximal during this time period and can act synergistically with rapamycin to reduce restenosis. In contrast to a dexamethasone eluting stent, perivascular delivery does not inhibit endothelial cell regeneration and acts directly on fibroblasts and smooth muscle cells.

TABLE 9

Cumulative in-vitro elution of dexamethasone from a collagen matrix.

| Eluted Dexamethasone Mass (micrograms) | Time (days) |
|---|---|
| 0 | 0 |
| 211 ± 23 | 1 |
| 489 ± 31 | 2 |
| 605 ± 42 | 3 |
| 672 ± 38 | 4 |
| 725 ± 21 | 5 |
| 733 ± 18 | 6 |
| 745 ± 13 | 7 |

Example 12

Combination of macro and micro porosity may increase capacity of the device. Collagen and fibrin matrices were mixed to obtain such a combination. In addition, good mechanical characteristics of collagen improved stability of fibrin. To prepare fibrin-Rapamycin loaded matrix, (Rapamycin density of 150 µg/cm$^2$) compositions disclosed in Tables 4 and 5 were used. 2. After formation of first dry layer of fibrin, second layer of collagen, rapamycin and heparin was formed as described in example 4 (Rapamycin density of 128 µg/cm$^2$, heparin density of 5000 U/cm$^2$). The collagen fibrin sheaths loaded with medicine (thickness 2 mm) were formed as tubular structures and externally crosslinked using high concentration of glutaraldehyde (25%) for one minute. After drying, spiral form of sleeve shown in FIG. 4 was prepared. This sleeve was made planar on ten occasions, the spiral shape was restored each time. The Rapamycin capacity of the final sleeve was 143 µg/cm$^2$. In vitro elution of heparin continues for 7 days.

Heparin concentration was measured as in example 10, buffer for the dilution was replenished each day. The data are shown in Table 10.

It is known that effective concentration of heparin to inhibit SMC proliferation is in the range of 100 µg/ml. In this example, heparin can significantly inhibit SMC proliferation for at least 4 days In addition diffusion of heparin form the sleeve can prevent thrombotic events on the inner surface of the shunt and damaged vessel wall for longer periods of time. Besides, concentration of soluble heparin can be increased up to 20,000 units/cm$^2$ without changing mechanical characteristics of the matrix. Therefore, anti smooth muscle cell proliferation as well as antithrombotic effect can be prolonged.

TABLE 10

Elution profile of heparin from a collagen matrix combined with rapamycin and heparin.

| Time (days) | Eluted Heparin Mass (U/ml) |
|---|---|
| 0 | 0 |
| 1 | 341 |
| 2 | 275 |
| 3 | 188 |
| 4 | 103 |
| 5 | 57 |
| 6 | 24 |

Examples 13 and 14: Comparison of in Vitro Effect of Rapamycin, Tacrolimus and Paclitaxel on Human Smooth Muscle and Endothelial Cells Human smooth muscle cells and endothelial cells (Clonetics, USA) were seeded (100,000 cells) in 24 well plates overnight. Both cell types were grown and maintained in OPTI-MEM (Gibco, Long Island, N.Y.) and 5% fetal bovine serum at 37° C. in a 5% carbon dioxide and 95% atmospheric air. Cells were exposed to a range of concentrations of Rapamycin (10-100 nM), Paclitaxel (0.1-10 mM) and Tacrolimus (10-100 nM). Each cell type was allowed to grow for 24 hours, last four hours in the presence of [$^3$H]-thymidine. Proliferation of cells was quantified as new DNA synthesis using $^3$H-thymidine uptake assay. After 72 hours of culture, cells were washed twice with cold phosphate buffered saline (PBS) and 1 ml of methanol was added to the contents of each well, the plates were kept at 4° C. for 60 minutes, cells were then washed once with cold PBS and 500 microliter of 0.2 m NaOH was added to each well and the plates were kept at 4° C. for 30 minutes. The contents of each well were transferred into scintillation vials and liquid scintillation fluid was added to quantify radioactivity using a liquid scintillation counter and results expressed as counts per minute.

Figure 16:
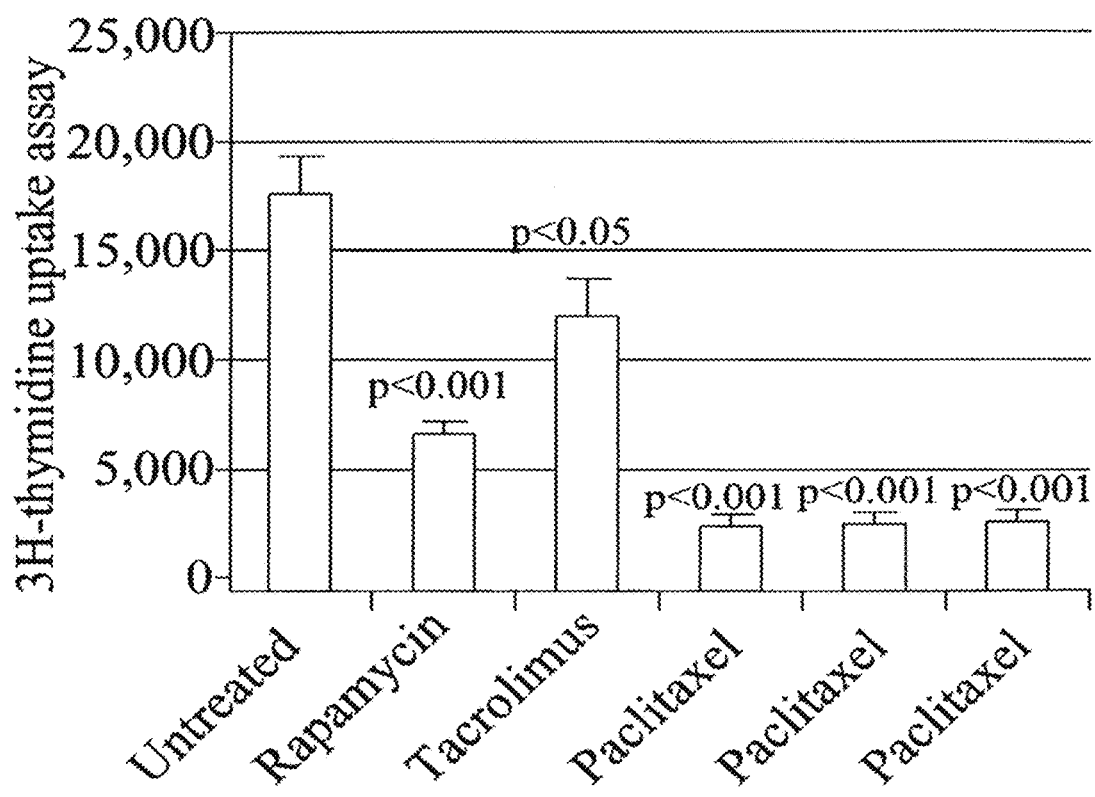
FIG. 16 Is a comparison of the effect of Rapamycin, Tacrolimus and Paclitaxel (3 doses) on Human Smooth Muscle Cells.
Figure 17:
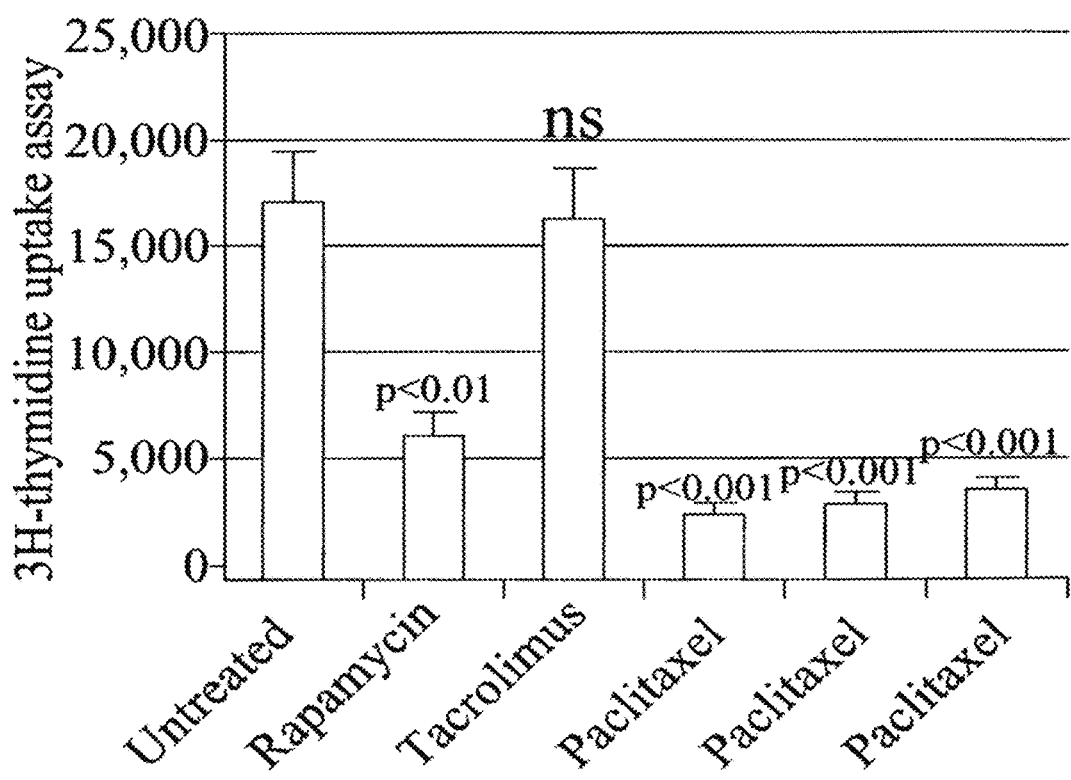
FIG. 17: Is a comparison of the effect of Rapamycin, Tacrolimus and Paclitaxel (3 doses) on Human Endothelial Cells.

Results are shown in Tables 11 and 12 and corresponding FIGS. 16 and 17 respectively. Rapamycin and Paclitaxel inhibit proliferation of both human smooth muscle and endothelial cells (new DNA synthesis). Tacrolimus appears to preferentially inhibit new DNA synthesis in human smooth muscle cells, sparing endothelial cells. This differential effect may be extremely important and can be beneficially exploited if Tacrolimus were to be used for inhibition of smooth muscle cell proliferation.

TABLE 11

Comparison of Effect of Rapamycin, Tacrolimus and Paclitaxel (3 doses) on Human Smooth Muscle Cells

| | [$^3$H]-thymidine uptake Assay Mean (±SD) | p |
|---|---|---|
| Untreated (Control) | 17434 (1822) | |
| Rapamycin | 6498 (245) | <0.01 |
| Tacrolimus | 11995 (1850) | <0.05 |
| Paclitaxel | 2421 (206) | <0.001 |
| Paclitaxel | 2527 (195) | <0.001 |
| Paclitaxel | 2710 (162) | <0.001 |

TABLE 12

Comparison of Effect of Rapamycin, Tacrolimus and Paclitaxel (3 doses) on Human Endothelial Cells

| | [$^3$H]-thymidine uptake Assay Mean (±SD) | p |
|---|---|---|
| Unttreated (Control) | 16342 (3039) | |
| Rapamycin | 5787 (1323) | <0.01 |
| Tacrolimus | 16073 (3008) | ns |
| Paclitaxel | 2222 (228) | <0.001 |
| Paclitaxel | 2648 (248) | <0.001 |
| Paclitaxel | 3459 (272) | <0.001 |

Animal Studies

A proof of principle study was performed using a porcine model. A total of 6 pigs were studied, 2 were used as controls and 4 were treated. A 6 mm PTFE vascular graft was anastomosed between the carotid artery on one side and the contralateral jugular vein, this created an arterio venous (AV) loop that is similar in construction to the human hemodialysis access loop. A collagen sleeve combined with a known dose of Rapamycin (approximately 500 µgm/cm$^2$) was placed around the distal end of the PTFE vascular graft just proximal to the venous anastomosis in the treated group.

After 30 days an angiogram was performed to demonstrate vessel and graft patency. The animals were euthanized and the relevant segments dissected. The inhibitory effect of Rapamycin on cell cycle progression, is believed to be via induction of cyclin inhibitors. Hence, expression of p21 will increase in tissues obtained from rapamycin treated animals but not from controls. In other words, the presence of p21 is confirmation that that the observed effect is attributable to Rapamycin. Tissues from treated and untreated animals were obtained, RNA was prepared and reverse transcribed to cDNA, which was amplified for house keeping gene, b-actin and p21 by PCR.

Results

Figure 20:
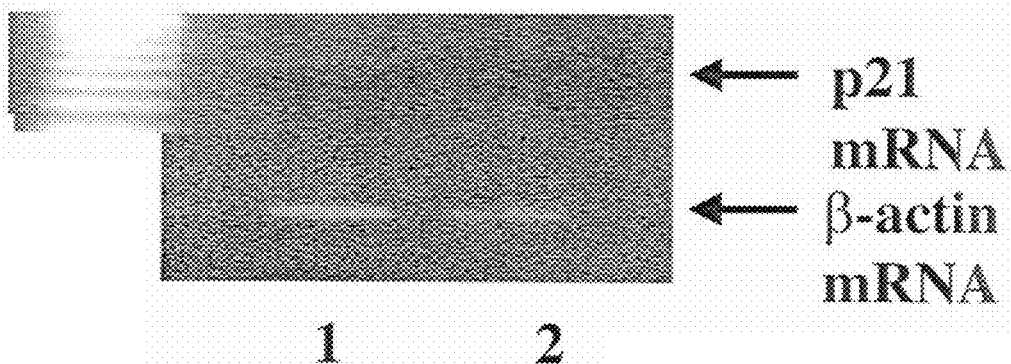

Both controls had luminal narrowing caused by severe neo-intimal hyperplasia at the site of venous anastomosis (FIGS. 18A and 19A). All 4 treated animals had significantly higher luminal patency of the vein and the graft, with minimal to absent neo intimal hyperplasia (FIGS. 18B and 19B). Expression of p21 mRNA was observed in venous tissue at the perianastamotic site obtained from rapamycin treated animals (FIG. 20) but not from controls. This demonstrates that the Rapamycin contained in the sleeve matrix was responsible for the reduction/virtual abolition of neo intimal hyperplasia (an expression of the vasculoproliferative response) an effect mediated through rapamycin induced inhibition of cellular proliferation.

The invention claimed is:

1. An implantable biocompatible, biodegradable matrix comprising material of sufficient flexibility to wrap to be wrapped around the exterior of a human vascular structure that includes an anastomosis from the formation of an arterio-venous fistula or an arterio-venous graft or an arterial-arterial graft and carrying an anti-vasculoproliferative drug which is rapamycin or an analogue of rapamycin with similar antiproliferative activity, wherein the anti-vasculoproliferative drug is both carried in a sufficient amount between about 50 micrograms and 2 milligrams per $cm^2$ and elutes from the material, when the material is in place around the vascular structure, at a rate sufficient to delay or prevent the occlusion of the vascular structure.

2. The matrix material of claim 1 wherein its thickness is between about 0.3 and 2.0 mm.

3. The matrix material of claim 2 wherein it has a pore size between about 0.001 and 100 microns.

4. The matrix material of claim 1 wherein the biocompatible matrix material is a polymer.

5. The matrix material of claim 4 wherein the biocompatible matrix material is a resorbable protein matrix.

6. The matrix material of claim 5 wherein the biocompatible matrix material comprises collagen.

7. The matrix material of claim 6 wherein it has a pore size between about 0.001 and 100 microns.

8. The matrix material of claim 7 wherein it has a pore size between about 0.002 and 0.1 microns.

9. The matrix material of claim 5 wherein the biocompatible matrix material comprises fibrin.

10. The matrix material of claim 4 wherein the biocompatible matrix material comprises chitosan.

* * * * *